US012751645B2

(12) United States Patent
Su et al.

(10) Patent No.: US 12,751,645 B2
(45) Date of Patent: Oct. 6, 2026

(54) METHODS AND DEVICES FOR MOTION MONITORING

(71) Applicant: SHENZHEN SHOKZ CO., LTD., Shenzhen (CN)

(72) Inventors: Lei Su, Shenzhen (CN); Meiqi Li, Shenzhen (CN); Xin Zhou, Shenzhen (CN); Fengyun Liao, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 383 days.

(21) Appl. No.: 18/182,373

(22) Filed: Mar. 13, 2023

(65) Prior Publication Data

US 2023/0210402 A1 Jul. 6, 2023

Related U.S. Application Data

(63) Continuation of application No. PCT/CN2022/081718, filed on Mar. 18, 2022.

(30) Foreign Application Priority Data

Mar. 19, 2021 (WO) ................ PCT/CN2021/081931
May 12, 2021 (WO) ................ PCT/CN2021/093302

(51) Int. Cl.

*A61B 5/11* (2006.01)
*A61B 5/00* (2006.01)
*A61B 5/389* (2021.01)

(52) U.S. Cl.

CPC ................ *A61B 5/11* (2013.01); *A61B 5/389* (2021.01); *A61B 5/486* (2013.01); *A61B 5/742* (2013.01)

(58) Field of Classification Search

CPC ........... A61B 5/11; A61B 5/389; A61B 5/486; A61B 5/742; A61B 5/7221; A61B 2560/0276; A61B 5/02438; A61B 5/296; A61B 5/4561; A61B 5/7455; A61B 2562/0219; A61B 5/4519; A61B 5/4866; A61B 5/1116; A61B 5/1121; A61B 5/397;
(Continued)

(56) References Cited

U.S. PATENT DOCUMENTS 5,679,004 A 10/1997 Mcgowan et al.
2004/0117212 A1 6/2004 Kong et al.
(Continued)

FOREIGN PATENT DOCUMENTS

CN 104706359 A 6/2015
CN 104720821 A 6/2015
(Continued)

OTHER PUBLICATIONS

International Search Report in PCT/CN2022/081718 mailed on Mar. 26, 2022, 7 pages.
(Continued)

*Primary Examiner* — Jeffrey G. Hoekstra
(74) *Attorney, Agent, or Firm* — METIS IP LLC

(57) ABSTRACT

The present disclosure discloses a method for displaying a motion monitoring interface. The method includes: obtaining a movement signal during a motion of a user from at least one sensor, wherein the movement signal at least includes an electromyographic signal or an attitude signal; determining information related to the motion of the user by processing the movement signal; and displaying the information related to the motion of the user.

20 Claims, 34 Drawing Sheets

2400

(58) Field of Classification Search
CPC ... A61B 5/6804; A61B 5/6823; A61B 5/7267; A61B 5/7405; A61B 5/7435; A61B 5/744; A61B 5/1123; A61B 2505/09; A61B 2560/0223; A61B 5/7475; G16H 20/30; G06F 9/451; G06F 3/011; G06F 3/015; G06F 3/017
See application file for complete search history.

(56) References Cited

U.S. PATENT DOCUMENTS

| | | | |
|---|---|---|---|
| 2009/0012381 | A1 | 1/2009 | Kuramori et al. |
| 2009/0319459 | A1 | 12/2009 | Breazeal et al. |
| 2011/0118621 | A1 | 5/2011 | Chu |
| 2012/0316453 | A1 | 12/2012 | Marcarian et al. |
| 2013/0116580 | A1 | 5/2013 | Liu et al. |
| 2013/0173764 | A1 | 7/2013 | Kami |
| 2014/0135960 | A1 | 5/2014 | Choi |
| 2014/0207017 | A1 | 7/2014 | Gilmore et al. |
| 2015/0045699 | A1 | 2/2015 | Mokaya et al. |
| 2015/0106025 | A1 | 4/2015 | Keller et al. |
| 2015/0272482 | A1 | 10/2015 | Houmanfar et al. |
| 2016/0027325 | A1 | 1/2016 | Malhotra |
| 2017/0025026 | A1 | 1/2017 | Ortiz Catalan |
| 2017/0076629 | A1 | 3/2017 | Kim et al. |
| 2017/0135640 | A1 | 5/2017 | Gunasekar et al. |
| 2017/0186335 | A1 | 6/2017 | Matsunaga |
| 2017/0224985 | A1 | 8/2017 | Debur et al. |
| 2017/0231521 | A1 | 8/2017 | Axelrod |
| 2017/0236442 | A1 | 8/2017 | Okada |
| 2018/0024635 | A1 | 1/2018 | Kaifosh et al. |
| 2018/0047157 | A1 | 2/2018 | Sinha et al. |
| 2018/0121713 | A1 | 5/2018 | Guo et al. |
| 2019/0046067 | A1 | 2/2019 | Du et al. |
| 2019/0343459 | A1 | 11/2019 | Korzinov et al. |
| 2020/0054931 | A1 | 2/2020 | Martin et al. |
| 2020/0155018 | A1 | 5/2020 | Igami |
| 2020/0302236 | A1 | 9/2020 | Gao et al. |
| 2020/0310541 | A1 | 10/2020 | Reisman et al. |
| 2021/0104213 | A1 | 4/2021 | Furuya et al. |
| 2023/0210402 | A1 | 7/2023 | Su et al. |

FOREIGN PATENT DOCUMENTS

| | | | |
|---|---|---|---|
| CN | 105268172 | A | 1/2016 |
| CN | 105635669 | A | 6/2016 |
| CN | 105705092 | A | 6/2016 |
| CN | 105796112 | A | 7/2016 |
| CN | 105797350 | A | 7/2016 |
| CN | 105997064 | A | 10/2016 |
| CN | 106073793 | A | 11/2016 |
| CN | 106955116 | A | 7/2017 |
| CN | 107115114 | A | 9/2017 |
| CN | 107320095 | A | 11/2017 |
| CN | 107349594 | A | 11/2017 |
| CN | 107361773 | A | 11/2017 |
| CN | 207071088 | U | 3/2018 |
| CN | 108211310 | A | 5/2018 |
| CN | 108143409 | A | 6/2018 |
| CN | 108209910 | A | 6/2018 |
| CN | 108211308 | A | 6/2018 |
| CN | 108211309 | A | 6/2018 |
| CN | 110109532 | A | 8/2018 |
| CN | 108566520 | A | 9/2018 |
| CN | 110478883 | A | 11/2018 |
| CN | 108960002 | A | 12/2018 |
| CN | 108983954 | A | 12/2018 |
| CN | 109068081 | A | 12/2018 |
| CN | 109191588 | A | 1/2019 |
| CN | 109330609 | A | 2/2019 |
| CN | 110327048 | A | 10/2019 |
| CN | 110443309 | A | 11/2019 |
| CN | 110472611 | A | 11/2019 |
| CN | 110569775 | A | 12/2019 |
| CN | 110609621 | A | 12/2019 |
| CN | 110638444 | A | 1/2020 |
| CN | 111028317 | A | 4/2020 |
| CN | 111317446 | A | 6/2020 |
| CN | 111803061 | A | 10/2020 |
| CN | 111938656 | A | 11/2020 |
| CN | 112120697 | A | 12/2020 |
| CN | 112214109 | A | 1/2021 |
| CN | 112336590 | A | 2/2021 |
| CN | 112472042 | A | 3/2021 |
| CN | 113192597 | A | 7/2021 |
| CN | 113230640 | A | 8/2021 |
| CN | 113749652 | A | 12/2021 |
| CN | 114081479 | A | 2/2022 |
| CN | 114298089 | A | 4/2022 |
| JP | 2003339908 | A | 12/2003 |
| JP | 2010246636 | A | 11/2010 |
| JP | 2011103914 | A | 6/2011 |
| JP | 2012024521 | A | 2/2012 |
| JP | 3181442 | U | 2/2013 |
| JP | 2014002655 | A | 1/2014 |
| JP | 2016150119 | A | 8/2016 |
| JP | 2017143911 | A | 8/2017 |
| JP | 2018083014 | A | 5/2018 |
| JP | 2019030520 | A | 2/2019 |
| JP | 2020103653 | A | 7/2020 |
| JP | 2020155961 | A | 9/2020 |
| KR | 20190044952 | A | 5/2019 |
| KR | 102000231 | B1 | 7/2019 |
| KR | 20200044323 | A | 4/2020 |
| WO | 2018214522 | A1 | 11/2018 |

OTHER PUBLICATIONS

Written Opinion in PCT/CN2022/081718 mailed on Mar. 26, 2022, 8 pages.

International Search Report in PCT/CN2021/061931 mailed on Dec. 22, 2021, 8 pages.

Written Opinion in PCT/CN2021/081931 mailed on Dec. 22, 2021, 6 pages.

International Search Report in PCT/CN2021/093302 mailed on Nov. 30, 2021, 7 pages.

Written Opinion in PCT/CN2021/093302 mailed on Nov. 30, 2021, 5 pages.

Notice of Preliminary Rejection in Korean Application No. 10-2023-7016947 mailed on Mar. 10, 2025, 16 pages.

Notice of Reasons for Rejection in Japanese Application No. 2023535549 mailed on Apr. 30, 2024, 10 pages.

The Extended European Search Report in European Application No. 22770633.0 mailed on Jun. 7, 2024, 9 pages.

The Extended European Search Report in European Application No. 21930919.2 mailed on Jan. 3, 2024, 10 pages.

First Office Action in Brazilian Application No. BR1120230067634 mailed on Oct. 2, 2025, 8 pages.

Notice of Preliminary Rejection in Korean Application No. 10-2023-7016055 mailed on Jul. 28, 2025, 14 pages.

João Lopes et al., Hand/arm gesture segmentation by motion using IMU and EMG sensing, 27th International Conference on Flexible Automation and Intelligent Manufacturing, 11: 107-113, 2017.

1200

1300

1400

2100

2500

Basic training information

Motion time: 1h20min
Interval time: 30min
Average heart rate: 110
Maximum heart rate: 145
Energy consumption: 500Kcal
Recovery time: 10h Exercise Counts

| | | | |
|---|---|---|---|
| Bench press | 50kg | 10/group | 3 groups |
| Biceps curl | 10kg | 10/group | 4 groups |
| High pulley | 10kg | 15/group | 3 groups |
| Butterfly machine reverse flying bird | 10kg | 15/group | 4 groups |

FIG. 25

METHODS AND DEVICES FOR MOTION MONITORING

CROSS-REFERENCE TO RELATED APPLICATIONS

The present disclosure is a continuation of International Application No. PCT/CN2022/081718, filed on Mar. 18, 2022, which claims priority of International Application No. PCT/CN2021/081931, filed on Mar. 19, 2021, and International Application No. PCT/CN2021/093302, filed on May 12, 2021, the content of each of which are hereby incorporated by reference.

TECHNICAL FIELD

The present disclosure relates to a technical field of wearable device, and in particular, to a motion monitoring method and device.

BACKGROUND

With people concerned about scientific exercise and physical health, motion monitoring devices are developing tremendously. At present, the motion monitoring devices mainly monitor some of the physiological parameter information (e.g., a heart rate, a body temperature, a step frequency, a blood oxygen, etc.) of a user during motion, display physiological data to the user, and give exercise suggestions based on the physiological data. In practical scenarios, motion monitoring devices often cannot display monitoring results of the motion to the user fully and accurately, resulting in the user can not know their own motion situation in time, or the physiological data given by the system is significantly different from the user's body feeling during motion, which may lead to a decline in the user's credibility of the motion monitoring devices.

Therefore, it is desired to provide a motion monitoring method and device to monitor and display motion data of a user during motion comprehensively and accurately.

SUMMARY

One aspect of the present disclosure may provide a method for displaying a motion monitoring interface. The method may include: obtaining a movement signal during a motion of a user from at least one sensor, wherein the movement signal at least includes an electromyographic signal or an attitude signal; determining information related to the motion of the user by processing the movement signal; and displaying the information related to the motion of the user.

In some embodiments, the determining information related to the motion of the user by processing the movement signal may include: determining an exertion strength of at least one muscle of the user based on the electromyographic signal.

In some embodiments, the displaying the information related to the motion the user may include: obtaining a user input regarding a target muscle; and displaying a status bar, wherein a color of the status bar is related to an exertion strength of the target muscle, or making a sound, wherein a volume of the sound is related to the exertion strength of the target muscle.

In some embodiments, the determining information related to the motion of the user by processing the movement signal may include: generating a user movement model representing a movement of the motion of the user based on the attitude signal.

In some embodiments, the displaying the information related to the motion of the user may include: obtaining a standard movement model; and displaying the user movement model and the standard movement model.

In some embodiments, the displaying the information related to the motion of the user may include: determining an exertion strength of at least one muscle of the user based on the electromyographic signal; and displaying the exertion strength of the at least one muscle on the user movement model.

In some embodiments, the determining information related to the motion of the user by processing the movement signal may include: segmenting the movement signal based on the electromyographic signal or the attitude signal; and determining a monitoring result by monitoring a movement of the motion of the user based on at least one segment of the movement signal.

In some embodiments, the method may further include: determining a movement feedback mode based on the monitoring result; and performing a movement feedback to the user according to the movement feedback mode.

In some embodiments, the at least one segment of the movement signal may be a movement signal of the user in at least one training process, and the monitoring result may include at least one of a movement type, a movement quantity, a movement quality, a movement time, physiological parameter information of the user, or a core stability of the user during the at least one training process.

In some embodiments, the monitoring result may include muscle information of the user corresponding to at least one time point, the muscle information of the user may include at least one of an energy consumption of at least one muscle, a fatigue degree of the at least one muscle, a balance of at least two muscles, or an ability of the at least one muscle, and the displaying the information related to the motion of the user may include: displaying at least one of the energy consumption of the at least one muscle, the fatigue degree of the at least one muscle, the balance of the at least two muscles, or the ability of the at least one muscle on at least one location in a user model, wherein the at least one location in the user model corresponds to a location of the at least one muscle in the user.

In some embodiments, energy consumptions of different muscles, fatigue levels of different muscles, training balances of different muscles, and/or abilities of different muscles may correspond to different display colors.

In some embodiments, the displaying the information related to the motion of the user may include: obtaining a user input regarding a target muscle; and displaying information of the target muscle.

In some embodiments, the displaying the information related to the motion of the user may include: displaying the monitoring result in at least one of a text, a chart, a sound, an image, or a video.

In some embodiments, the method may further include: calibrating the movement signal.

In some embodiments, the method may further include: determining whether a working state of the at least one sensor is normal based on the movement signal; and in response to determining that the working state of the at least one sensor is abnormal, displaying prompt information.

In some embodiments, the movement signal may include a signal related to a feature of the user, and the method may further include: determining body shape information and/or body composition information of the user based on the signal related to the feature of the user; and displaying the body shape information and/or body composition information of the user.

Some embodiments of the present disclosure may also provide an electronic device. The electronic device may include: a display device configured to display content; an input device configured to receive a user input; and at least one sensor configured to detect a movement signal during a motion of a user, wherein the movement signal may at least include an electromyographic signal or an attitude signal; and a processor connected to the display device, the input device, and the at least one sensor, wherein the processor is configured to: obtain the movement signal during the motion of the user from the at least one sensor; determine information related to the motion of the user by processing the movement signal; and control the display device to display the information related to the motion of the user.

BRIEF DESCRIPTION OF THE DRAWINGS

The present disclosure will be further described in the form of exemplary embodiments, which will be described in detail by the accompanying drawings. These embodiments are not limiting. In these embodiments, the same number represents the same structure, wherein:

FIG. 25 is a schematic diagram of a motion monitoring interface according to some embodiments of the present disclosure;

DETAILED DESCRIPTION

Figure 1:
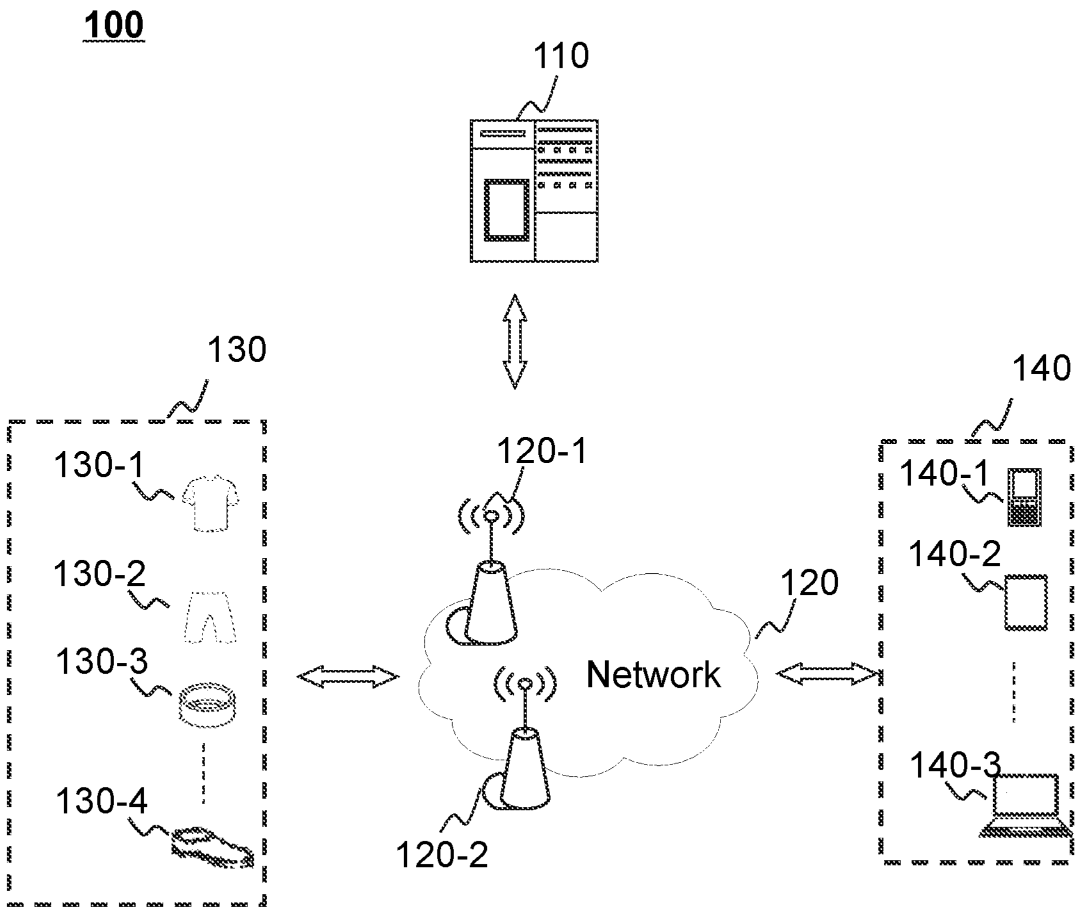
FIG. 1 is a schematic diagram of an application scenario of a motion monitoring system according to some embodiments of the present disclosure.

In order to more clearly explain the technical scheme of the embodiments of the present disclosure, the following will briefly introduce the drawings that need to be used in the description of the embodiments. Obviously, the drawings in the following description are only some examples or embodiments of the present disclosure. For those skilled in the art, the present disclosure may also be applied to other similar scenarios according to these drawings without creative work. Unless it is obvious from the language environment or otherwise stated, the same label in the figure represents the same structure or operation.

It will be understood that the term “system,” “device,” “unit,” and/or “module” used herein are one method to distinguish different components, elements, parts, sections or assemblies of different levels in ascending order. However, if other words may achieve the same purpose, the words may be replaced by other expressions.

As used in the disclosure and the appended claims, the singular forms “a,” “an,” and “the” include plural referents unless the content clearly dictates otherwise. Generally speaking, the terms “comprise,” “comprises,” and/or “comprising,” “include,” “includes,” and/or “including,” only imply that the clearly identified steps and elements are included, these steps and elements may not constitute an exclusive list, and the method or device may further include other steps or elements.

Flowcharts are used throughout the present disclosure to illustrate the operations performed by the system according to embodiments of the present disclosure. It should be understood that the preceding or following operations are not necessarily performed in precise order. Instead, the individual steps may be processed in reverse order or simultaneously. Other operations may be added to these processes or a step or steps of operations may be removed from these processes.

The present disclosure may provide a motion monitoring system. The system may obtain a movement signal of a user during motion. The movement signal may include at least an electromyographic signal, an attitude signal, an electrocardio graphic signal, a respiratory rate signal, and the like. The motion monitoring system may monitor a movement of the user during motion based at least on feature information corresponding to the electromyographic signal or the feature information corresponding to an attitude signal. For example, the system may determine the type of movement of the user, the number of movement, the movement quality, the movement time, or the information of physiological parameters of the user when performing the movement through frequency information and amplitude information corresponding to the electromyographic signal, an angular velocity, an angular velocity direction and an angular velocity value of the angular velocity, an angle, displacement information, and stress, etc., corresponding to the attitude signal. In some embodiments, the motion monitoring system may further generate feedback to a user’s fitness movement according to analysis results of the user’s fitness movement to provide guidance to user’s fitness. For example, when the user’s fitness movement is not standard, the motion monitoring system can send a prompt message to the user (e.g., a voice prompt, a vibration prompt, current stimulation, etc.). The motion monitoring system may be applied to a wearable device (e.g., clothing, a wrist guard, a helmet), a medical testing device (e.g., an electromyography tester), a fitness device, etc. The motion monitoring system may accurately monitor and provide feedback on a user’s movement by obtaining the movement signal of the user during motion without professional participation, which can improve the user’s fitness efficiency and reduce a cost of the user fitness.

FIG. 1 is a schematic diagram illustrating an application scenario of a motion monitoring system according to some embodiments of the present disclosure. As shown in FIG. 1, the motion monitoring system 100 may include a processing device 110, a network 120, a wearable device 130, and a mobile terminal device 140. The motion monitoring system 100 may obtain a movement signal (e.g., an electromyographic signal, an attitude signal, an electro-cardio signal, a respiratory rate signal, etc.) representing a movement of user motion, and may monitor and provide feedback on the movement of the user during motion according to a user’s movement signal.

For example, the motion monitoring system 100 may monitor and provide feedback on the movement of the user during fitness. When the user wears the wearable device 130 for fitness, the wearable device 130 may obtain the user’s movement signal. The processing device 110 or a mobile terminal device may receive and analyze the user’s movement signal to determine whether the user’s fitness movement is standard, thereby monitoring the user’s movement. Specifically, the monitoring of the user’s movement may include determining a type of movement, a count of movement, a quality of the movement, and a time of the movement, or information about the physiological parameters of the user at the time the movement is performed. Further, the motion monitoring system 100 may generate feedback on the user's fitness movement according to an analysis result of the user's fitness movement to provide guidance to the user.

Further, for example, the motion monitoring system 100 may monitor and provide feedback on the user's movement while running. For example, when the user wears the wearable device 130 for running exercise, the motion monitoring system 100 may monitor whether the user's running movement is standard and whether the running time meets a health standard. When a user's running time is too long or a running movement is incorrect, the fitness device may provide motion state to the user to prompt the user to adjust the running movement or the running time.

In some embodiments, the processing device 110 may be configured to process information and/or data related to the user's movement. For example, the processing device 110 may receive the movement signal of the user (e.g., an electromyographic signal, an attitude signal, an electrocardio signal, a respiratory rate signal, etc.) and further extract the feature information corresponding to the movement signal (e.g., the feature information corresponding to the electromyographic signal in the movement signal, the feature information corresponding to the attitude signal). In some embodiments, the processing device 110 may perform a specific signal processing, such as a signal segmentation, a signal pre-processing (e.g., a signal correction processing, a filtering processing, etc.), etc., on the electromyographic signal or the attitude signal obtained by the wearable device 130. In some embodiments, the processing device 110 may further determine whether the user movement is correct based on the user's movement signal. For example, the processing device 110 may determine whether the user movement is correct based on the feature information corresponding to the electromyographic signal (e.g., amplitude information, frequency information, etc.). As another example, the processing device 110 may determine whether the user movement is correct based on the feature information corresponding to the attitude signal (e.g., an angular velocity, a direction of angular velocity, an acceleration of angular velocity, an angle, displacement information, a stress, etc.). Further, for example, the processing device 110 may determine whether the user movement is correct based on the feature information corresponding to the electromyographic signal and the feature information corresponding to the attitude signal. In some embodiments, the processing device 110 may further determine whether information of physiological parameters of the user during motion meets the health standard. In some embodiments, the processing device 110 may further send a corresponding instruction configured to feed the user's movement back. For example, when the user is running and the motion monitoring system 100 monitors that the user's running time is too long, the processing device 110 may send the instruction to the mobile terminal device 140 to prompt the user to adjust the running time. It should be noted that the feature information corresponding to the attitude signal is not limited to above angular velocity, the direction of angular velocity, the acceleration of angular velocity, the angle, the displacement information, and the stress, etc., but can also be other feature information. For example, when an attitude sensor is a strain gauge sensor, a bending angle and a bending direction at a user's joint may be obtained by measuring the resistance in a strain gauge sensor that varies with a stretch length.

In some embodiments, the processing device 110 may be local or remote. For example, the processing device 110 may access information and/or materials stored in the wearable device 130 and/or the mobile terminal device 140 through the network 120. In some embodiments, the processing device 110 may be directly connected to the wearable device 130 and/or the mobile terminal device 140 to access the information and/or materials stored therein. For example, the processing device 110 may be located in the wearable device 130 and implement the information interact with the mobile terminal device 140 through the network 120. Further, for example, the processing device 110 may be located in the mobile terminal device 140 and implement the information interact with the wearable device 130 through a network. In some embodiments, the processing device 110 may be executed on a cloud platform. For example, the cloud platform may include one of a private cloud, a public cloud, a hybrid cloud, a community cloud, a decentralized cloud, an internal cloud, or any combination thereof.

In some embodiments, the processing device 110 may process data and/or information related to motion monitoring to perform one or more of functions described in the present disclosure. In some embodiments, the processing device 110 may obtain the movement signal collected by the wearable device 130 while the user is in motion. In some embodiments, the processing device may send a control instruction to the wearable device 130 or the mobile terminal device 140. The control instruction may control an on/off state of the wearable device 130 and its respective sensor, and also control the mobile terminal device 140 to send a prompt message. In some embodiments, processing device 110 may include one or more sub-processing devices (e.g., a single-core processing device or a multi-core processing device). Merely by way of example, the processing device 110 may include a central processing unit (CPU), an application-specific integrated circuit (ASIC), an application-specific instruction processor (ASIP), a graphic processing unit (GPU), a physics processing Unit (PPU), a digital signal processor (DSP), a field-programmable gate array (FPGA), an programmable logic device (PLD), a controller, a microcontroller unit reduced instruction set computer (RISC), and a microprocessor, or the like, or any combination of the above.

The network 120 may facilitate the exchange of data and/or information in the motion monitoring system 100. In some embodiments, one or more components of the motion monitoring system 100 (e.g., the processing device 110, the wearable device 130, the mobile terminal device 140) may send the data and/or the information to other components of the motion monitoring system 100 through network 120. For example, the movement signal collected by the wearable device 130 may be transmitted to the processing device 110 through the network 120. As another example, confirmation results regarding the movement signal in the processing device 110 may be transmitted to the mobile terminal device 140 through the network 120. In some embodiments, the network 120 may be any type of a wired or wireless network. For example, the network 120 may include a cable network, a wired network, a fiber optic network, a telecommunications network, an internal network, an inter-network, a regional network (LAN), a wide area network (WAN), a wireless regional network (WLAN), a metropolitan area network (MAN), a public switched telephone network (PSTN), a Bluetooth™ network, a ZigBee™ network, and a near field communication (NFC) network, or any combination of the above. In some embodiments, the network 120 may include one or more network entry and exit points. For example, network 120 may include wired or wireless network entry and exit points, such as a base station and/or inter-network exchange points 120-1, 120-2, . . . , through the entry and exit points, one or more components of motion monitoring system 100 may connect to the network 120 to exchange the data and/or the information.

The wearable device 130 may be a garment or a device that has a wearable function. In some embodiments, the wearable device 130 may include, but is not limited to, an upper garment device 130-1, a pant device 130-2, a wrist guard device 130-3, and a shoe 130-4, etc. In some embodiments, wearable device 130 may include a plurality of sensors. The sensors may obtain various movement signals (e.g., an electromyographic signal, an attitude signal, temperature information, a heart rate, an electro-cardio signal, etc.) from the user during motion. In some embodiments, the sensors may include, but are not limited to, one or more of an electromyographic sensor, an attitude sensor, a temperature sensor, a humidity sensor, an electro-cardio sensor, an oxygen saturation sensor, a Hall sensor, a Pico electric sensor, a rotation sensor, etc. For example, an electromyographic sensor may be provided at a human muscle location (e.g., biceps, triceps, latissimus dorsi, trapezius, etc.) in the upper garment device 130-1, and the electromyographic sensor may fit to user's skin and collect the electromyographic signal from the user during motion. For example, the upper garment device 130-1 may be provided with an electro-cardio sensor near the left pectoral muscle of the human body, and the electromyographic sensor may collect the electro-cardio signal of the user. Further, for example, the attitude sensor may be provided at a human body muscle location (e.g., gluteus maximus, lateral femoris, medial femoris, gastrocnemius, etc.) in the pant device 130-2, and the attitude sensor may collect a user's attitude signal. In some embodiments, the wearable device 130 may further provide feedback on the user's movement. For example, if the user's movement of a body part during motion does not meet the standard, the electromyographic sensor corresponding to that part may generate a stimulation signal (e.g., a current stimulation or a strike signal) to prompt the user.

It should be noted that the wearable device 130 is not limited to the upper garment device 130-1, the pant device 130-2, the wrist guard device 130-3, and the shoe device 130-4 shown in FIG. 1, but may further include a device that are applied to other devices that require motion monitoring, such as, for example, a helmet device, a knee pad, etc., which may not be limited herein, and any device that can use the motion monitoring method provided in the disclosure is within the scope of protection of the present disclosure.

In some embodiments, the mobile terminal device 140 may access information or data in the motion monitoring system 100. In some embodiments, the mobile terminal device 140 may receive motion data processed by the processing device 110, and feed motion records back based on processed motion data. Exemplary feedback manners may include, but are not limited to, a voice prompt, an image prompt, a video display, a text prompt, etc. In some embodiments, the user may obtain movement records during an own movement through the mobile terminal device 140. For example, the mobile terminal device 140 may be connected to the wearable device 130 through the network 120 (e.g., the wired connection, the wireless connection), and the user may obtain the movement records during the user's movement through the mobile terminal device 140, which may be transmitted to the processing device 110 through the mobile terminal device 140. In some embodiments, the mobile terminal device 140 may include a mobile device 140-1, a tablet 140-2, a laptop 140-3, or the like, or any combination thereof. In some embodiments, the mobile device 140-1 may include a cell phone, a smart home device, a smart mobility device, a virtual reality device, an augmented reality device, or the like, or any combination thereof. In some embodiments, the smart home device may include a control device of a smart appliance, a smart monitoring device, a smart TV, a smart camera, or the like, or any combination thereof. In some embodiments, the smart mobility device may include a smart phone, a personal digital assistant (PDA), a gaming device, a navigation device, a POS device, or the like, or any combination thereof. In some embodiments, a virtual reality device and/or an augmented reality device may include a virtual reality helmet, virtual reality glasses, a virtual reality eye-mask, an augmented reality helmet, an augmented reality glasses, and an augmented reality eye-mask, or the like, or any combination thereof.

In some embodiments, the motion monitoring system 100 may further include a database. The database may store the information (e.g., a threshold condition of an initially set, etc.) and/or the instruction (e.g., a feedback instruction). In some embodiments, the database may store the information obtained from the wearable device 130 and/or the mobile terminal device 140. In some embodiments, the database may store the information and/or the instruction configured for the processing device 110 to execute or use to perform the exemplary methods described in the present disclosure. In some embodiments, the database may include a mass storage, a removable memory, a volatile read-write memory (e.g., random access memory RAM), a read-only memory (ROM), or the like, or any combination thereof. In some embodiments, the database may be implemented on a cloud platform. For example, the cloud platform may include a private cloud, a public cloud, a hybrid cloud, a community cloud, a decentralized cloud, an internal cloud, or the like, or any combination thereof.

In some embodiments, the database may be connected to the network 120 to communicate with one or more components of the motion monitoring system 100 (e.g., the processing device 110, the wearable device 130, the mobile terminal device 140, etc.). The one or more components of the motion monitoring system 100 may access information or instruction stored in the database through the network 120. In some embodiments, the database may be directly connected or communicate with one or more components of the motion monitoring system 100 (e.g., the processing device 110, the wearable device 130, the mobile terminal device 140). In some embodiments, the database may be a part of the processing device 110

Figure 2:
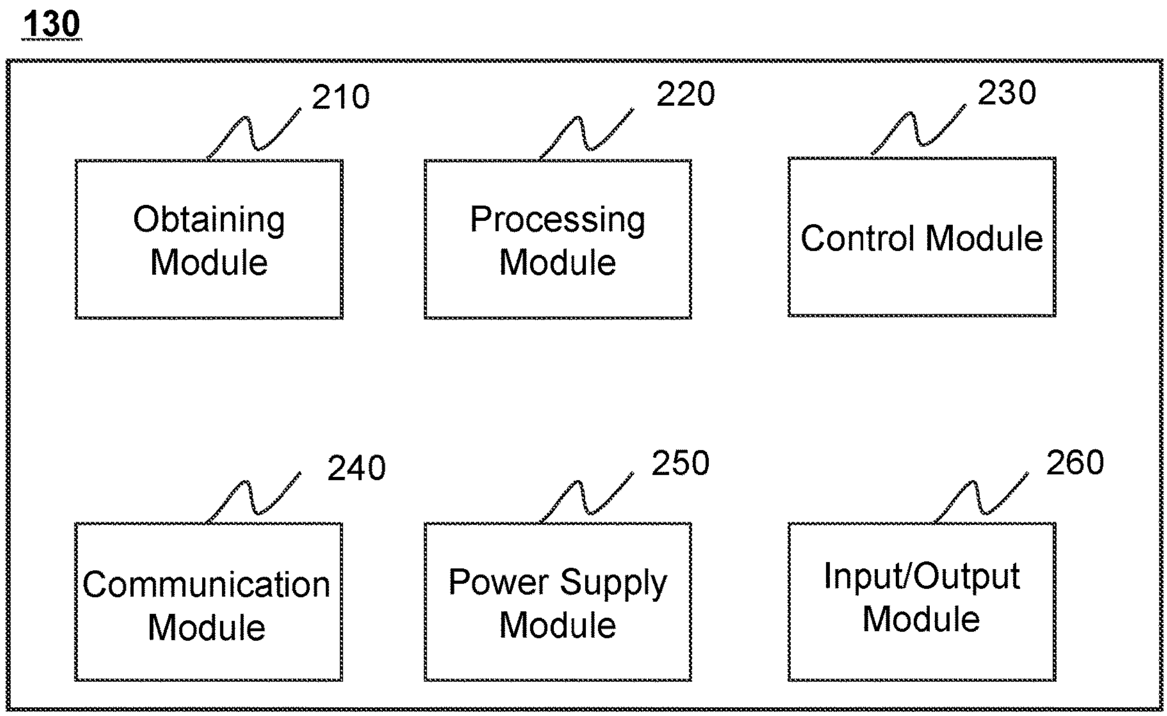
FIG. 2 is a schematic diagram of illustrating exemplary hardware and/or software of a wearable device according to some embodiments of the present disclosure.

FIG. 2 is a schematic diagram illustrating exemplary hardware and/or software of a wearable device according to some embodiments of the present disclosure. As shown in FIG. 2, the wearable device 130 may include an obtaining module 210, a processing module 220 (also referred to as a processor), a control module 230 (also referred to as a master, a MCU, a controller), a communication module 240, a power supply module 250, and an input/output module 260.

The obtaining module 210 may be configured to obtain a movement signal of a user during motion. In some embodiments, the obtaining module 210 may include a sensor unit. The sensor unit may be configured to obtain one or more movement signals while the user is in motion. In some embodiments, the sensor unit may include, but is not limited to, one or more electromyographic sensors, attitude sensors, cardiac sensors, respiration sensors, temperature sensors, humidity sensors, inertial sensors, blood oxygen saturation sensors, Hall sensors, piezoelectric sensors, rotation sensors, or the like. In some embodiments, the movement signal may include one or more electromyographic signals, attitude signals, cardiac signals, respiratory rates, temperature signals, humidity signals, etc. The sensor unit may be placed at different locations of the wearable device 130 according to a type of a movement signal to be obtained. For example, in some embodiments, the electromyographic sensor (also referred to as an electrode element) may be placed at a human muscle location, and the electromyographic sensor may be configured to collect the electromyographic signal of the user during motion. The electromyographic signal and its corresponding feature information (e.g., frequency information, amplitude information, etc.) may reflect a state of muscle during a user's movement. The attitude sensor may be provided at different locations on a human body (e.g., locations of the wearable device 130 corresponding to the torso, limbs, and joints), and the attitude sensor may be configured to capture the attitude signal of the user during the user's movement. The attitude signal and its corresponding feature information (e.g., an angular velocity direction, an angular velocity value, an acceleration value of an angular velocity, an angle, a displacement information, a stress, etc.) may reflect the attitude of the user's movement. The electromyographic sensor may be set at a location on the circumferential side of the human chest, and the electromyographic sensor may be configured to collect electro cardio data of the user during motion. The respiration sensor may be arranged on a circumferential side of the body's chest, and the respiration sensor may be configured to collect respiration data (e.g., a respiration rate, a respiration amplitude, etc.) from the user during motion. The temperature sensor may be configured to collect temperature data (e.g., a body surface temperature) of the user during motion. The humidity sensor may be configured to collect humidity data of an external environment of the user during motion.

The processing module 220 may process data from the obtaining module 210, the control module 230, the communication module 240, the power supply module 250, and/or the input/output module 260. For example, the processing module 220 may process the movement signal of the user during a process of motion from the obtaining module 210. In some embodiments, the processing module 220 may pre-process the movement signal (e.g., the electromyographic signal, the attitude signal) obtained by the obtaining module 210. For example, the processing module 220 may segment the electromyographic signal or the attitude signal of the user during motion. As another example, the processing module 220 may perform a pre-processing (e.g., a filtering processing, a signal correction processing) on the electromyographic signal of the user during motion to improve quality of the electromyographic signal. Further, for example, the processing module 220 may determine the feature information corresponding to the attitude signal based on a user's attitude signal during motion. In some embodiments, the processing module 220 may process an instruction or operation from an input/output module 260. In some embodiments, processed data may be stored in a memory or a hard disk. In some embodiments, the processing module 220 may transmit its processed data to one or more components in the motion monitoring system 100 through the communication module 240 or the network 120. For example, the processing module 220 may send monitoring results of the user during motion to the control module 230, which may execute subsequent operations or instructions according to motion determination results.

The control module 230 may be connected to other modules in the wearable device 130. In some embodiments, the control module 230 may control operation states of other modules (e.g., the communication module 240, the power supply module 250, the input/output module 260) in the wearable device 130. For example, the control module 230 may control a power supply state (e.g., a normal mode, a power saving mode), a power supply time, or the like, of the power supply module 250. When the remaining power of the power supply module 250 reaches a certain threshold (e.g., 10%) or less, the control module 230 may control the power supply module 250 to enter a power saving mode or send a prompt message about the replenishment of power. As another example, the control module 230 may control the input/output module 260 based on user's movement determination results, and further control the mobile terminal device 140 to send feedback results of the user's movement. When there is a problem with the user's movement (e.g., movement not meeting the standard), the control module 230 may control the input/output module 260 to control the mobile terminal device 140 to provide feedback to the user, allowing the user to understand own motion movement in real time and make some adjustments. In some embodiments, the control module 230 may also control one or more sensors or other modules in the obtaining module 210 to provide feedback to the human body. For example, when a muscle of the user is exercising too strong during motion, the control module 230 may control an electrode module at a location of the muscle to stimulate the user to prompt the user to adjust the movement in time.

In some embodiments, the communication module 240 may be configured for an exchange of information or data. In some embodiments, the communication module 240 may be configured for communication between components (e.g., the obtaining module 210, the processing module 220, the control module 230, the power supply module 250, the input/output module 260) within a wearable device 130. For example, the obtaining module 210 may send a movement signal (e.g., the electromyographic signal, the attitude signal, etc.) to the communication module 240, and the communication module 240 may send the movement signal to the processing module 220. For example, the communication module 240 may send state information (e.g., a switch state) of the wearable device 130 to the processing device 110, and the processing device 110 may monitor the wearable device 130 based on the state information. The communication module 240 may employ wired, wireless, and hybrid wired/wireless technologies. The wired technology may be based on one or more combinations of fiber optic cables such as metallic cables, hybrid cables, fiber optic cables, etc. The wireless technology may include a Bluetooth (Bluetooth™), a wireless network (Wi-Fi), a purple bee (ZigBee™) a near field communication (NFC), a radio frequency identification (RFID), a cellular network (including GSM, CDMA, 3G, 4G, 5G, etc.), a cellular-based narrow band internet of things (NBIoT), etc. In some embodiments, the communication module 240 may use one or more coding methods to encode transmitted information, for example, the coding methods may include a phase coding, a non-zeroing coding, a differential Manchester coding, or the like. In some embodiments, the communication module 240 may select different transmission and encoding methods according to a type of data or a type of network to be transmitted. In some embodiments, the communication module 240 may include one or more communication interfaces for different communication methods. In some embodiments, illustrated other modules of the motion monitoring system 100 may be dispersed on a plurality of devices, in this case, each of a plurality of other modules may each include one or more communication modules 240 for an inter-module information transmission. In some embodiments, the communication module 240 may include a receiver and a transmitter. In other embodiments, the communication module 240 may be a transceiver.

In some embodiments, the power supply module 250 may provide power to other components in the motion monitoring system 100 (e.g., the obtaining module 210, the processing module 220, the control module 230, the communication module 240, the input/output module 260). The power supply module 250 may receive the control signal from the processing module 220 to control a power output of the wearable device 130. For example, if the wearable device 130 does not receive any operation (e.g., no movement signal is detected by the obtaining module 210) for a certain period (e.g., 1 s, 2 s, 3 s, or 4 s), the power supply module 250 may supply power to the memory merely, putting the wearable device 130 into a standby mode. For example, if the wearable device 130 does not receive any operation (e.g., no movement signal is detected by the obtaining module 210) for a certain period (e.g., 1 s, 2 s, 3 s, or 4 s), the power supply module 250 may disconnect power to other components and the data in the motion monitoring system 100 may be transmitted to a hard disk, putting the wearable device 130 into the standby mode or a sleeping mode. In some embodiments, the power supply module 250 may include at least one battery. The battery may include one or more combinations of a dry cell, a lead battery, a lithium battery, a solar cell, a wind energy generation battery, a mechanical energy generation battery, a thermal energy generation battery, etc. Light energy may be converted into electrical energy by the solar battery and stored in the power supply module 250. Wind energy may be converted into the electrical energy by the wind power generation battery and stored in the power supply module 250. Mechanical energy may be converted into the electrical energy by the mechanical energy generation battery and stored in the power supply module 250. The solar cell may include a silicon solar cell, a thin film solar cell, a nanocrystalline chemical solar cell, a fuel sensitized solar cell, a plastic solar cell, etc. The solar cell may be distributed on the wearable device 130 in a form of panel. A user's body temperature may be converted into the electrical energy by the thermal power cell and stored in the power supply module 250. In some embodiments, the processing module 220 may send the control signal to the power supply module 250 when the power supply module 250 is less than a power threshold (e.g., 10% of the total power). The control signal may include information that the power supply module 250 is low on power. In some embodiments, the power supply module 250 may include a backup power source. In some embodiments, the power supply module 250 may further include a charging interface. For example, the power supply module 250 may be temporarily charged by using an electronic device (e.g., a cell phone, a tablet computer) or a rechargeable battery carried by the user to temporarily charge the power supply module 250 in an emergency (e.g., the power supply module 250 is at zero power and an external power system is out of power).

The input/output module 260 may obtain, transmit, and send a signal. The input/output module 260 may connect to or communicate with other components in the motion monitoring system 100. The other components in the motion monitoring system 100 may be connected or communicated through the input/output module 260. The input/output module 260 may be a wired USB interface, a serial communication interface, a parallel communication port, or a wireless Bluetooth, an infrared-frequency identification, a radio-frequency identification (RFID), a WLAN authentication and privacy infrastructure (WAPI), a general packet radio service (GPRS), a code division multiple access (CDMA), or any combination thereof. In some embodiments, the input/output module 260 may be connected to the network 120 and obtain the information through the network 120. For example, the input/output module 260 may obtain the movement signal from the obtaining module 210 of the user during motion and output user movement information through the network 120 or the communication module 240. In some embodiments, the input/output module 260 may include VCC, GND, RS-232, RS-485 (e.g., RS485-A, RS485-B), a universal network interface, or the like, or any combination thereof. In some embodiments, the input/output module 260 may transmit obtained user motion information to the obtaining module 210 through the network 120. The encoding methods may include a phase coding, a non-zeroing system encoding, a differential Manchester encoding, or the like, or any combination thereof.

It should be understood that the system and its modules shown in FIG. 2 may be implemented by using a plurality of methods. For example, in some embodiments, the system and its modules may be implemented by hardware, software, or a combination of software and hardware. In particular, a hardware portion may be implemented by using dedicated logic. A software portion may be stored in memory and executed by an appropriate instruction execution system, such as a microprocessor or dedicated design hardware. Those skilled in the art may understand that the above methods and the system can be implemented by using a computer executable instruction and/or contained in a processor control code, for example, such encoding provided on a carrier medium such as a disk, a CD or a DVD-ROM, a programmable memory such as a read-only memory (firmware), or a data carrier such as an optical or electronic signal carrier. The system and its modules in one or more embodiments of the present disclosure may be implemented by a hardware circuit, e.g., a ultra-large scale integrated circuit or a gate array, a semiconductor such as a logic chip, a transistor, etc., or a programmable hardcore device such as a field programmable gate array, a programmable logic device, etc., implemented by software executed by various types of processors, or implemented by a combination of above hardware circuit and software (e.g., firmware).

It should be noted that the above description of the motion monitoring system and its modules is merely for descriptive convenience and does not limit one or more embodiments of the present disclosure within the scope of the embodiments. Understandably, for those skilled in the art, after understanding a principle of the system, they may make any combination of the modules, or to form a sub-system to connect with other modules, or to omit one or more modules thereof, without departing from this principle. For example, the obtaining module 210 and the processing module 220 may be one module that may have a function of obtaining and processing the user movement signal. As another example, the processing module 220 may not be provided in the wearable device 130, but integrated in the processing device 110. Variations such as these are within the scope of protection of one or more embodiments of the present disclosure.

Figure 3:
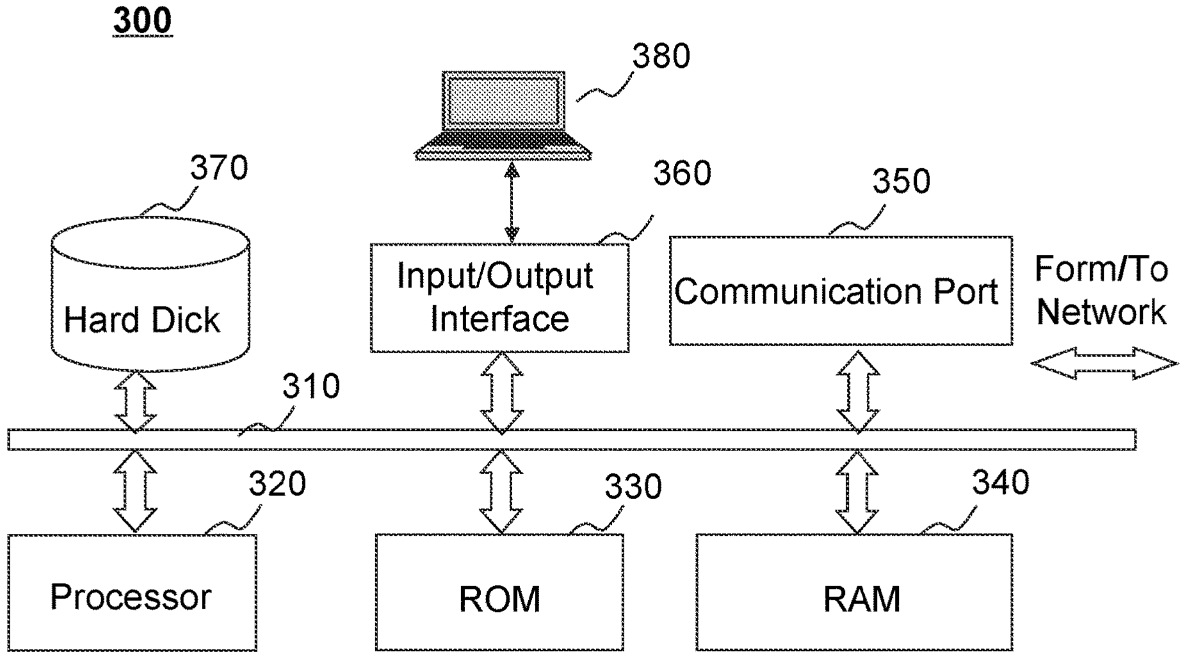
FIG. 3 is a schematic diagram illustrating exemplary hardware and/or software of a computing device according to some embodiments of the present disclosure.

FIG. 3 is a schematic diagram illustrating exemplary hardware and/or software of a computing device according to some embodiments of the present disclosure. In some embodiments, the processing device 110 and/or the mobile terminal device 140 may be implemented on a computing device 300. As shown in FIG. 3, the computing device 300 may include an internal communication bus 310, a processor 320, a read-only memory 330, a random memory 340, a communication port 350, an input/output interface 360, a hard disk 370, and a user interface 380.

The internal communication bus 310 may enable data communication between components in the computing device 300. For example, the processor 320 may send data to other hardware such as a memory or the input/output interface 360 through the internal communication bus 310. In some embodiments, the internal communication bus 310 may be an industry standard architecture (ISA) bus, an extended industry standard architecture (EISA) bus, a video electronics standard architecture (VESA) bus, a peripheral component interconnect (PCI) bus, etc. In some embodiments, the internal communication bus 310 may be configured to connect various modules (e.g., the obtaining module 210, the processing module 220, the control module 230, the communication module 240, the input and output module 260) of the motion monitoring system 100 shown in FIG. 1.

The processor 320 may execute a computing instruction (a program code) and perform functions of the motion monitoring system 100 described in the present disclosure. The computing instruction may include a program, an object, a component, a data structure, a process, a module, and a function (the function may refer to a specific function described in the present disclosure). For example, processor 320 may process the obtained movement signal (e.g., the electromyographic signal, the attitude signal) of a user during motion from the wearable device 130 or/and the mobile terminal device 140 of the motion monitoring system 100, and monitor the movement of the user during motion based on the movement signal during motion. In some embodiments, the processor 320 may include a microcontroller, a microprocessor, a reduced instruction set computer (RISC), an application-specific integrated circuit (ASIC), an application-specific instruction-set processor (ASIP), a central processing unit (CPU), a graphics processing unit (GPU), a physical processing unit (PPU), a microcontroller unit, a digital signal processor (DSP), a field Programmable Gate Array (FPGA), an advanced RISC machine (ARM), a programmable logic device, and any circuit and processor capable of performing one or more functions, or any combination thereof. For illustrative purposes only, the computing device 300 in FIG. 3 depicts only one processor, but it should be noted that the computing device 300 in the present disclosure may further include a plurality of processors.

A memory of the computing device 300 (e.g., a read-only memory (ROM) 330, a random access memory (RAM) 340, a hard disk 370, etc.) may store data/information obtained from any other components of the motion monitoring system 100. In some embodiments, the memory of the computing device 300 may be located in the wearable device 130 or the processing device 110. Exemplary ROM may include a mask ROM (MROM), a programmable ROM (PROM), an erasable programmable ROM (PEROM), an electrically erasable programmable ROM (EEPROM), a compact disk ROM (CD-ROM), a digital versatile disk ROM, etc. Exemplary RAM may include a dynamic RAM (DRAM), a double-rate synchronous dynamic RAM (DDR SDRAM), a static RAM (SRAM), a thyristor RAM (T-RAM), a zero-capacitor RAM (Z-RAM), etc.

The input/output interface 360 may input or output signals, data, or information. In some embodiments, the input/output interface 360 may enable a user to interact with the motion monitoring system 100. For example, the input/output interface 360 may include the communication module 240 to enable the communication function of the motion monitoring system 100. In some embodiments, the input/output interface 360 may include an input device and an output device. Exemplary input devices may include a keyboard, a mouse, a touch screen, a microphone, or the like, or any combination thereof. Exemplary output devices may include a display device, a loudspeaker, a printer, a projector, or the like, or any combination thereof. Example display devices may include a liquid crystal display (LCD), a light-emitting diode (LED)-based display, a flat panel display, a curved display, a television device, a cathode ray tubes (CRT), or the like, or any combination thereof. The communication port 350 may be connected to a network for data communication. Connection may be a wired connection, a wireless connection, or a combination thereof. The wired connection may include a cable, a fiber optic cable, a telephone line, or the like, or any combination thereof. The wireless connection may include Bluetooth™, Wi-Fi, WiMAX, WLAN, ZigBee™, a mobile network (e.g., 3G, 4G, or 5G, etc.), or the like, or any combination thereof. In some embodiments, the communication port 350 may be a standard port, such as RS232, RS485, etc. In some embodiments, the communication port 350 may be a specially designed port.

The hard disk 370 may be configured to store information and data generated by or received from the processing device 110. For example, the hard disk 370 may store confirmation information of a user. In some embodiments, the hard disk 370 may include a hard disk drive (HDD), a solid-state drive (SSD), or a hybrid hard disk (HHD), etc. In some embodiments, the hard disk 370 may be provided in the processing device 110 or in the wearable device 130. The user interface 380 may enable an interact and information exchange between the computing device 300 and the user. In some embodiments, the user interface 380 may be configured to present motion recordings generated by the motion monitoring system 100 to the user. In some embodiments, the user interface 380 may include a physical display such as a display with speakers, an LCD display, an LED display, an OLED display, an electronic ink display (E-Ink), etc.

Figure 4:
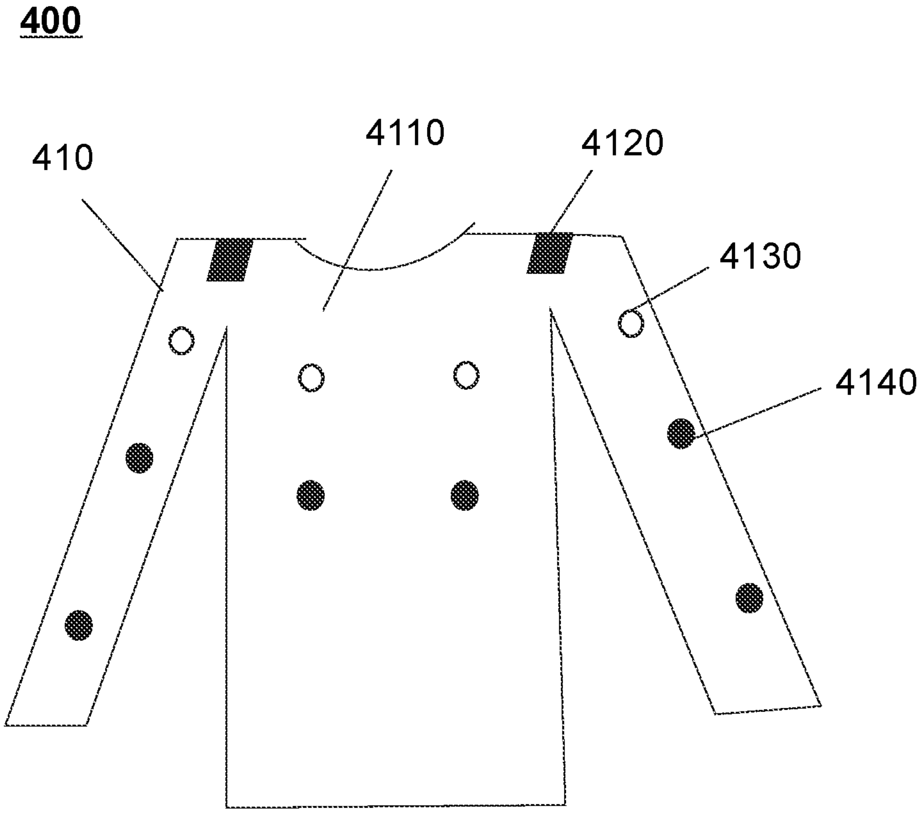
FIG. 4 is a structure diagram of an exemplary wearable device according to some embodiments of the present disclosure.

FIG. 4 is a structure diagram of an exemplary wearable device according to some embodiments of the present disclosure. To further describe the wearable device, an upper garment is illustrated as an example, as shown in FIG. 4. The wearable device 400 may include an upper garment 410. The upper garment 410 may include an upper garment substrate 4110, at least one upper garment processing module 4120, at least one upper garment feedback module 4130, at least one upper garment obtaining module 4140, etc. The upper garment substrate 4110 may refer to clothe worn on an upper body of a human body. In some embodiments, the upper garment substrate 4110 may include a short sleeve T-shirt, a long sleeve T-shirt, a shirt, a jacket, etc. The at least one upper garment processing module 4120, the at least one upper garment obtaining module 4140 may be located in areas of the upper garment substrate 4110 that fit to different parts of the human body. The at least one upper garment feedback module 4130 may be located at any location on the upper garment substrate 4110, and the at least one upper garment feedback module 4130 may be configured to provide feedback on information about a user's upper body movement state. Exemplary feedback manners may include, but are not limited to, a voice prompt, a text prompt, a pressure prompt, an electrical stimulation, etc. In some embodiments, the at least one upper garment obtaining module 4140 may include, but is not limited to, one or more of an attitude sensor, an electro-cardio sensor, an electromyographic sensor, a temperature sensor, a humidity sensor, an inertial sensor, an acid-base sensor, an acoustic transducer, etc. The sensor(s) in the upper garment obtaining module 4140 may be placed at different locations on user's body according to a signal to be measured. For example, when the attitude sensor is configured to obtain the attitude signal of a user during motion, the attitude sensor can be placed in the upper garment substrate 4110 at a location corresponding to the human torso, arms, and joints. As another example, when the electromyographic sensor is configured to obtain the electromyographic signal of the user during motion, the electromyographic sensor may be located near the muscles to be measured. In some embodiments, the attitude sensor may include, but is not limited to, an acceleration triaxial sensor, an angular velocity triaxial sensor, a magnetic sensor, or the like, or any combination thereof. For example, an attitude sensor may include an acceleration triaxial sensor, an angular velocity triaxial sensor. In some embodiments, an attitude sensor may further include a strain gauge sensor. A strain gauge sensor may be a sensor based on strain generated by deformation of an object to be measured caused by a force. In some embodiments, the strain gauge sensor may include, but is not limited to, one or more of a strain-gauge force sensor, a strain-gauge pressure sensor, a strain-gauge torque sensor, a strain-gauge displacement sensor, a strain-gauge acceleration sensor, etc. For example, the strain gauge sensor may be arranged at a joint location of the user, and a bending angle and a bending direction at the user's joint can be obtained based on the resistance in the strain gauge sensor that varies with a stretch length at the joint. It should be understood that the upper garment 410 may include other modules, such as a power supply module, a communication module, an input/output module, etc., in addition to the upper garment substrate 4110, the upper garment processing module 4120, the upper garment feedback module 4130, and the upper garment obtaining module 4140 described above. The upper garment processing module 4120 may be similar to the processing module 220 shown in FIG. 2, and the upper garment obtaining module 4140 may be similar to the obtaining module 210 shown in FIG. 2. Specific descriptions regarding various modules in the upper garment 410 may be found in FIG. 2 and its relevant descriptions of the present disclosure, which may not be repeated herein.

Figure 5:
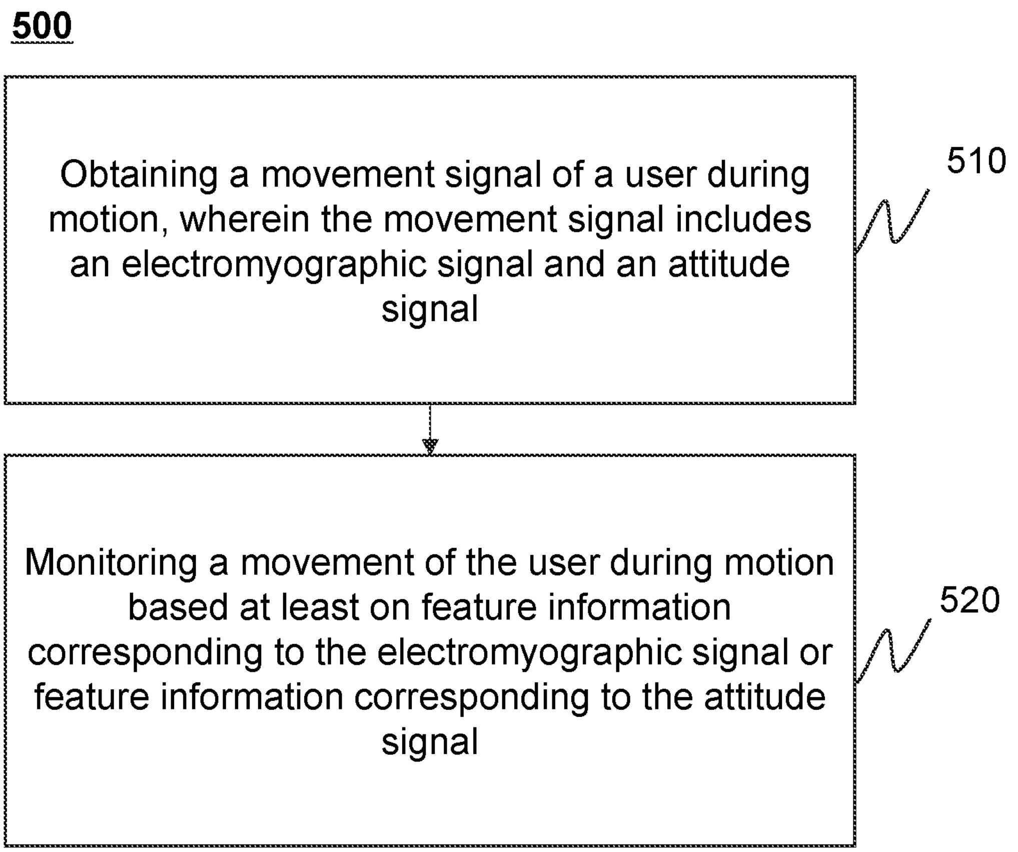
FIG. 5 is a flowchart illustrating an exemplary motion monitoring method according to some embodiments of the present disclosure.

FIG. 5 is a flowchart illustrating an exemplary motion monitoring method according to some embodiments of the present disclosure. As shown in FIG. 5, process 500 may include the following steps.

In step 510, a movement signal of a user during motion may be obtained.

In some embodiments, the step 510 may be performed by the obtaining module 210. The movement signal refers to human body parameter information of the user during motion. In some embodiments, the human body parameter information may include, but is not limited to, one or more of an electromyographic signal, an attitude signal, an electro-cardio signal, a temperature signal, a humidity signal, a blood oxygen concentration, a respiration rate, etc. In some embodiments, an electromyographic sensor in the obtaining module 210 may collect the electromyographic signal of the user during motion. For example, when the user performs a seated chest press, the electromyographic sensors in a wearable device corresponding to human pectoral muscles, latissimus dorsi, etc., may obtain the electromyographic signals of corresponding muscle positions of the user. As another example, when a user performs a deep squat, the electromyographic sensors in the wearable device corresponding to gluteus maximus and quadriceps may collect the electromyographic signals of the corresponding muscle positions. As another example, when the user is running, the electromyographic sensors in the wearable device corresponding to the gastrocnemius muscle and other positions may obtain the electromyographic signals of the corresponding muscle positions. In some embodiments, the attitude sensor in the obtaining module 210 may obtain an attitude signal of the user during motion. For example, when the user performs a barbell bench press, the attitude sensor in the wearable device corresponding to the human triceps, etc., may obtain the attitude signal of the triceps, etc. For example, when the user performs a dumbbell flyover, the attitude sensor set at a position such as a human deltoid muscle may obtain the attitude signal of the corresponding position. In some embodiments, a plurality of attitude sensors may obtain attitude signals of a plurality of portions of the user during motion, and the attitude signals of the plurality of portions may reflect a relative movement between different parts of the body. For example, an attitude signal at an arm and an attitude signal at a torso may reflect a movement condition of the arm relative to the torso. In some embodiments, the attitude signal may be associated with a type of the attitude sensor. For example, when the attitude sensor is an angular velocity tri-axis sensor, an obtained attitude signal may be angular velocity information. As another example, when the attitude sensor is the angular velocity tri-axis sensor and an acceleration tri-axis sensor, the obtained attitude signal may be the angular velocity information and acceleration information. For example, when the attitude sensor is a strain gauge sensor, the strain gauge sensor may be arranged at a user's joint position, by measuring the resistance in the strain gauge sensor that varies with the stretch length, the obtained attitude signal may be displacement information, stress, etc., and a bending angle and a bending direction at the user's joint may be represented through these attitude signals. It should be noted that the parameter information configured to reflect the relative motion of the user's body may be feature information corresponding to the attitude signal, which may be obtained by using different types of attitude sensors according to the type of the feature information.

In some embodiments, the movement signal may include the electromyographic signal and the attitude signal of a particular part of the user's body. The electromyographic signal and the attitude signal may reflect a movement state of the particular part of the user's body from different angles. In simple terms, the attitude signal of a specific part of the user's body may reflect a type of movement, a movement amplitude, a movement frequency, etc., of the specific part. The electromyographic signal may reflect a muscle state of the particular part during motion. In some embodiments, by measuring the electromyographic signal and/or the attitude signal of the same body part, whether the movement of that part is standard may be better assessed.

In step 520, a movement of the user during motion may be monitored based at least on feature information corresponding to the electromyographic signal or feature information corresponding to the attitude signal.

In some embodiments, the step 520 may be performed by the processing module 220 and/or the processing device 110. In some embodiments, the feature information corresponding to the electromyographic signal may include, but is not limited to, one or more of frequency information, amplitude information, etc. The feature information corresponding to the attitude signal may be parameter information configured to represent a relative motion of the user's body. In some embodiments, the feature information corresponding to the attitude signal may include, but is not limited to, one or more of an angular velocity direction, an angular velocity value, an acceleration value of angular velocity, etc. In some embodiments, the feature information corresponding to the attitude signal may further include an angle, displacement information (e.g., a stretch length in a strain gauge sensor), a stress, etc. For example, when the attitude sensor is a strain gauge sensor, the strain gauge sensor may be set at the user's joint position, and by measuring the resistance in the strain gauge sensor that varies with the stretch length, the obtained attitude signal may be the displacement information, the stress, etc., which may represent the bending angle and the bending direction at the user's joint. In some embodiments, the processing module 220 and/or the processing device 110 may extract the feature information corresponding to the electromyographic signal (e.g., frequency information, amplitude information) or the feature information corresponding to the attitude signal (e.g., the angular velocity direction, the angular velocity value, the acceleration value of angular velocity, the angle, the displacement information, the stress, etc.), and monitor the movement of the user during motion based on the feature information corresponding to the electromyographic signal or the feature information corresponding to the attitude signal. The monitoring of the movement during motion may include user's movement-related information. In some embodiments, movement-related information may include one or more of a movement type, a movement quantity, a movement quality (e.g., whether the movement meets a standard), a movement time, etc. The movement type may be a fitness movement performed by the user during motion. In some embodiments, the movement type may include, but is not limited to, one or more of seated chest presses, deep squats, hard pulls, plank supports, running, swimming, etc. The movement quantity may refer to the number of times the user performs the movement during motion. For example, if the user performs 10 seated chest clamps during motion, 10 may be the movement quantity. The movement quality may refer to the standard degree of the fitness movement performed by the user related to a standard fitness movement. For example, when the user performs a deep squat movement, the processing device 110 may determine a movement type of the user based on the feature information corresponding to the movement signal (the electromyographic signal and the attitude signal) of a particular specific muscle location (gluteus maximus, quadriceps, etc.), and determine the movement quality of the user during performing the deep squat movement based on the movement signal. The movement time may be the time corresponding to one or more movement types of the user or the total time of the movement process. Detailed descriptions for monitoring the movement of the user during motion based on the feature information corresponding to the electromyographic signal and/or the feature information corresponding to the attitude signal may be found in FIG. 6 and its relevant descriptions of the present disclosure.

In some embodiments, the processing device 110 may use one or more movement recognition models to recognize and monitor the movement of the user during motion. For example, the processing device 110 may input the feature information corresponding to the electromyographic signal and/or the feature information corresponding to the attitude signal into the movement recognition model, and the movement recognition model may output information related to the user's movement. In some embodiments, the movement recognition model may include different types of movement recognition models, for example, a model configured to recognize the movement type of the user, or a model configured to identify the movement quality of the user, etc.

It should be noted that the above description regarding process 500 is for exemplary and illustrative purpose only, and does not limit the scope of application of the present disclosure. For those skilled in the art, various amendments and changes can be made to the process 500 under the guidance of the present disclosure. However, these amendments and changes are still within the scope of the present disclosure. For example, the extraction of the feature information corresponding to the electromyographic signal or the feature information corresponding to the attitude signal in step 520 may be performed by the processing device 110, or in some embodiments, by the processing module 220. As another example, the user's movement signal may not be limited to the above electromyographic signal, the attitude signal, the electro-cardio signal, the temperature signal, the humidity signal, the blood oxygen concentration, the respiration rate, but may also include other human physiological parameter signals. The physiological parameter signals involved in human movement may be all considered as the movement signal in the embodiments of the present disclosure.

Figure 6:
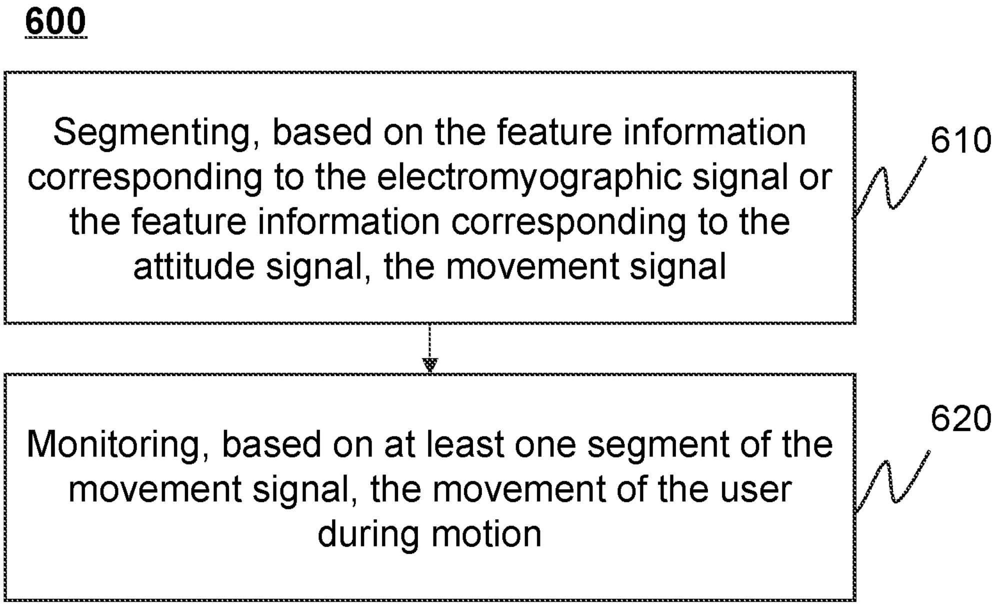
FIG. 6 is a flowchart of an exemplary process for monitoring a movement of a motion of a user according to some embodiments of the present disclosure.

FIG. 6 is a flowchart of an exemplary process for monitoring a movement of a user during motion according to some embodiments of the present disclosure. As shown in FIG. 6, process 600 may include the following steps.

In step 610, the movement signal may be segmented based on the feature information corresponding to the electromyographic signal or the feature information corresponding to the attitude signal.

In some embodiments, the step may be performed by the processing module 220 and/or the processing device 110. The process of obtaining the movement signal (e.g., the electromyographic signal, the attitude signal) of the user during motion may be continuous, and a movement of the user during motion may be a combination of a plurality of sets of movement or a combination of different movement types. To analyze each movement of the user during motion, the processing module 220 may segment the movement signal of the user based on the feature information corresponding to the electromyographic signal or the feature information corresponding to the attitude signal. The segmenting the movement signal of the user herein may refer to dividing the movement signal into signal segments having same or different durations, or extracting one or more signal segments having a specific duration from the movement signal. In some embodiments, each segment of the movement signal may correspond to one or more complete movement of the user. For example, when a user performs a deep squat, the user's movement from a standing position to a squat position and then getting up to return to the standing position may be considered as completing the deep squat, and the movement signal collected by the obtaining module 210 during this process may be considered as one segment (or one cycle) of the movement signal, after which the movement signal collected by the obtaining module 210 from the next deep squat completed by the user may be considered as another segment of the movement signal. In some embodiments, each movement signal may also correspond to a portion of the user's movement, and the portion of the movement may be understood as a portion of a complete movement. For example, when a user performs a deep squat, the user's movement from a standing position to a squat position may be considered as one segment of the movement, and getting up to return to the standing position may be considered as another segment of the movement. A change in each movement of the user during motion may cause the electromyographic signal and the attitude signal of a corresponding body part to change. For example, when the user performs a squat, the electromyographic signal and the attitude signal of the muscles in the corresponding parts of the user's body (e.g., arms, legs, hips, abdomen) fluctuate less when the user stands; when the user squats from the standing position, the electromyographic signal and the attitude signal of the muscles in the corresponding parts of the user's body fluctuate more, e.g., amplitude information corresponding to signals of different frequencies of the electromyographic signal becomes greater, or an angular velocity value, a direction of angular velocity, an acceleration value of angular velocity, an angle, displacement information, stress, etc., of the attitude signal may also change. When the user gets up from a squatting state to a standing state, the amplitude information corresponding to the electromyographic signal and the angular velocity value, the direction of angular velocity, the acceleration value of angular velocity, the angle, the displacement information, and the stress corresponding to the attitude signal may change again. Based on this situation, the processing module 220 may segment, based on the feature information corresponding to the electromyographic signal or the feature information corresponding to the attitude signal, the movement signal. Detailed descriptions for segmenting the movement signal based on the feature information corresponding to the electromyographic signal or the feature information corresponding to the attitude signal may be found in FIG. 7 and FIG. 8 of the present disclosure and their related descriptions.

In step 620, the movement of the user during motion may be monitored based on at least one segment of the movement signal.

The step may be performed by processing module 220 and/or processing device 110. In some embodiments, monitoring of the movement of the user based on at least one segment of the movement signal may include matching the at least one segment of the movement signal with at least one segment of a preset movement signal to determine the movement type of the user. The at least one segment of the preset movement signal may be standard movement signals corresponding to different movements that are preset in a database. In some embodiments, a movement type of the user during motion may be determined by determining a matching degree of the at least one segment of the movement signal and the at least one segment of the preset movement signal. Further, the movement type of the user may be determined by determining whether the matching degree of the movement signal and the preset movement signal is within a first matching threshold range (e.g., greater than 80%). If so, the movement type of the user during motion may be determined based on the movement type corresponding to the preset movement signal. In some embodiments, monitoring the movement of the user during motion based on the at least one segment of the movement signal may further include determining the movement type of the user during motion by matching the feature information corresponding to the at least one segment of the electromyographic signal with feature information corresponding to an electromyographic signal of the at least one segment of the preset movement signal. For example, match degree(s) between one or more feature information (e.g., frequency information, amplitude information) of the segment of the electromyographic signal and one or more feature information of the segment of the preset movement signal may be determined respectively, and a determination may be made as to whether a weighted matching degree of the one or more feature information or an average matching degree of the one or more feature information is within a first matching threshold. If so, the movement type of the user during motion may be determined based on the movement type corresponding to the preset movement signal. In some embodiments, monitoring the movement of the user during motion based on the at least one segment of the movement signal may further include determining the movement type of the user during motion by matching the feature information corresponding to the at least one segment of the attitude signal with the feature information corresponding to the attitude signal of the at least one segment of the preset movement signal. For example, the matching degree of the one or more feature information (e.g., the angular velocity value, the angular velocity direction and the acceleration value of the angular velocity, the angle, the displacement information, the stress, etc.) of one segment of the attitude signal and the one or more feature information of one segment of the preset movement signal may be determined respectively to determine whether the weighted matching degree or the average matching degree of the one or more feature information is within the first matching threshold. If so, the movement type of the user may be determined according to a movement type corresponding to the preset movement signal. In some embodiments, monitoring the movement of the user during motion based on the at least one segment of the movement signal may further include determining the movement type of the user during motion by matching the feature information corresponding to the electromyographic signal and the feature information corresponding to the attitude signal of the at least one segment of the movement signal with the feature information corresponding to the electromyographic signal and the feature information corresponding to the attitude signal of the at least one segment of the preset movement signal.

In some embodiments, monitoring the movement of the user during motion based on the at least one segment of the movement signal may include determining the movement quality of the user by matching the at least one segment of the movement signal with the at least one segment of the preset movement signal. Further, if a matching degree of the movement signal and the preset movement signal is within a second matching threshold range (e.g., greater than 90%), the movement quality of the user during motion may meet the standard. In some embodiments, determining the movement of the user during motion based on the movement signal of the at least one segment may include determining the movement quality of the user during motion by matching the one or more feature information of the movement signal of the at least one segment with the one or more feature information of the at least one segment of the preset movement signal. It should be noted that a segment of the movement signal may be a movement signal of a complete movement or a movement signal of a partial of a complete movement. In some embodiments, for a complex complete movement, there may be different ways of force generation at different stages of the complete movement, that is, there may be different movement signals at the different stages of the movement, and the user movement may be monitored in real time, and thus, the accuracy of the monitored movement signal at the different stages of the complete movement may be improved.

It should be noted that the above description of the process 600 is for example and illustration purposes only and does not limit the scope of application of the present disclosure. For those skilled in the art, various amendments and changes can be made to process 600 under the guidance of the present disclosure. However, these amendments and changes are still within the scope of the present disclosure. For example, in some embodiments, the user's movement may also be determined by a movement recognition model or a manually preset model.

Figure 7:
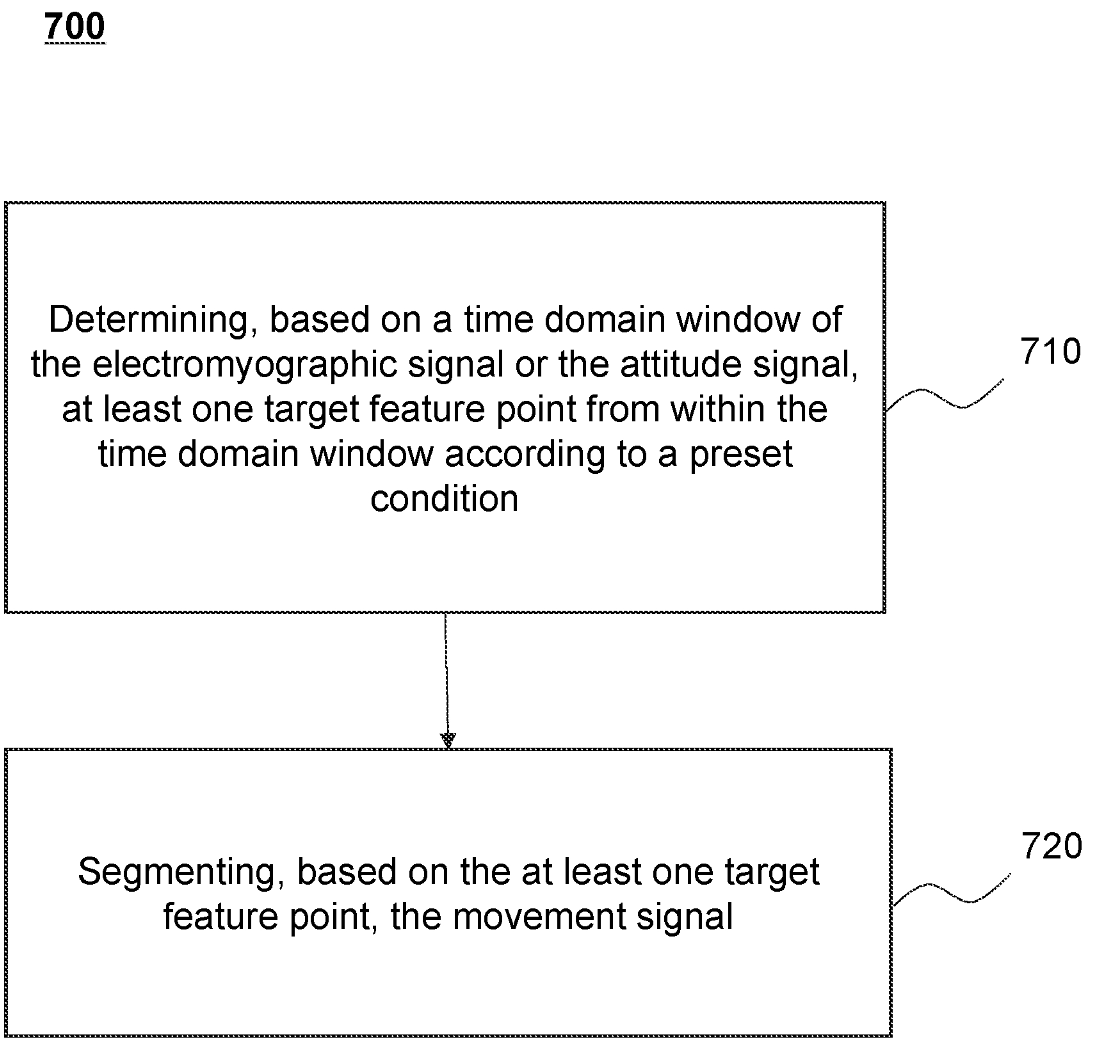
FIG. 7 is a flowchart of an exemplary process for segmenting a movement signal according to some embodiments of the present disclosure.

FIG. 7 is a flowchart of an exemplary process for segmenting a movement signal according to some embodiments of the present disclosure. As shown in FIG. 7, process 700 may include the following steps.

In step 710, at least one target feature point within the time domain window may be determined based on a time domain window of the electromyographic signal or the attitude signal and according to a preset condition.

In some embodiments, the step may be performed by the processing module 220 and/or the processing device 110. The time domain window of the electromyographic signal may include an electromyographic signal over a range of time, and the time domain window of the attitude signal may include an attitude signal over a same range of time. A target feature point refers to a signal of the movement signal with a target feature, which may represent a stage of the user's movement. For example, when a user performs a seated chest press, at the beginning, the user's arms are extended outward horizontally, begin to rotate internally, come together, and finally return to the extended state again in the horizontal direction, this process is a complete seated chest press movement. When the user performs a seated chest press movement, the feature information corresponding to the electromyographic signal or the attitude signal may be different in each stage. By analyzing the feature information corresponding to the electromyographic signal (e.g., amplitude information, frequency information) or the feature information corresponding to the attitude signal (e.g., the angular velocity value, the direction of angular velocity, the acceleration value of angular velocity, the angle, the displacement information, the stress, etc.), the target feature point corresponding to a stage of the user's movement may be determined. In some embodiments, one or more target feature points may be determined from the time domain window based on the preset condition. In some embodiments, the preset condition may include one or more of a change in the direction of the angular velocity corresponding to the attitude signal, the angular velocity corresponding to the attitude signal being greater than or equal to an angular velocity threshold, the angle corresponding to the attitude signal reaching an angular threshold, the change of the angular velocity value corresponding to the attitude signal being the extreme value, and the amplitude information corresponding to the electromyographic signal being greater than or equal to an electromyographic threshold. In some embodiments, the target feature points at the different stages of a movement may correspond to different preset conditions. For example, in the seated chest press, a preset condition for a target feature point when the user's arms are horizontally extended outward and then start to internally rotate may be different from a preset condition for a target feature point when the arms are brought together. In some embodiments, the target feature points of different movements may correspond to different preset conditions. For example, the chest press movement and the bent-over movement may be different, and the preset conditions regarding the respective preset target feature points in these two movements may also be different. Exemplary descriptions of the preset condition may refer to the description of a movement start point, a movement middle point, and a movement end point in the present disclosure.

In other embodiments, the at least one target feature point may be determined from the time domain windows based on both of the time domain windows of the electromyographic signal and the attitude signal, according to the preset condition. The time domain windows of the electromyographic signal and the attitude signal may include the electromyographic signal and the attitude signal over a range of time. The time of the electromyographic signal may correspond to the time of the attitude signal. For example, a time point of the electromyographic signal when the user starts to move may be the same as a time point of the attitude signal when the user starts to move. The target feature point here may be determined by combining the feature information corresponding to the electromyographic signal (e.g., the amplitude information) and the feature information corresponding to the attitude signal (e.g., the angular velocity value, the direction of angular velocity, the acceleration value of angular velocity, the angle, etc.).

In step 720, the movement signal may be segmented based on the at least one target feature point.

In some embodiments, the step 720 may be performed by the processing module 220 and/or the processing device 110. In some embodiments, the target feature point in the electromyographic signal or the attitude signal may be one or more, and the movement signal may be divided into multiple segments by one or more target feature points. For example, when there is a target feature point in the electromyographic signal, the target feature point may divide the electromyographic signal into two segments, where the two segments may include the electromyographic signal before the target feature point and the electromyographic signal after the target feature point. Alternatively, the processing module 220 and/or the processing device 110 may extract the electromyographic signal for a certain time range around the target feature point as a segment of the electromyographic signal. As another example, when the electromyographic signal has a plurality of target feature points (e.g., n-target feature points, and the first target feature point is not a beginning of the time domain window, the $n^{th}$ target feature point is not an end of the time domain window), the electromyographic signal may be divided into (n+1) segments based on the n target feature points. As another example, when the electromyographic signal has the plurality of target feature points (e.g., n-target feature points, the first target feature point is the beginning of the time domain window, the $n^{th}$ target feature point is not the end of the time domain window), the electromyographic signal may be divided into n segments based on the n target feature points. As a further example, when the electromyographic signal has the plurality of target feature points (e.g., n-target feature points, the first target feature point is the beginning of the time domain window, the $n^{th}$ target feature point is the end of the time domain window), the electromyographic signal may be divided into (n−1) segments based on the n target feature points. It should be noted that the movement stage corresponding to the target feature point may include one or more types. When the movement stage corresponding to the target feature point are multiple types, the plurality of target feature points may be used as a benchmark for segmenting the movement signal. For example, the movement stage corresponding to the target feature point may include the movement start point and the movement end point, the movement start point may be before the movement end point, and in this situation, the movement signal between the movement start point and a next movement start point may be considered as a segment of the movement signal.

In some embodiments, the target feature point may include one or more of the movement start point, the movement middle point, or the movement end point.

To describe the segmentation of the movement signal, take the target feature point including all of the movement start point, the movement middle point and the movement end point as an exemplary illustration. The movement start point may be considered as a start point of a user movement cycle. In some embodiments, different movements may correspond to different preset conditions. For example, in the seated chest press, the preset condition may be that the direction of the angular velocity of the movement after the movement start point changes relative to the direction of the angular velocity of the movement before the movement start point, or that the value of the angular velocity at the movement start point is approximately 0 and the acceleration value of the angular velocity at the movement start point is greater than 0. In other words, when the user performs the seated chest press, the movement starting point may be set to the point when the arms are extended outward horizontally and start to internally rotate. As another example, in a bent-over movement, the preset condition may be that the angle of arm lift is greater than or equal to an angle threshold. Specifically, when the user performs a bent-over movement, the angle of arm lift when the user's arm is horizontal is 0°, the angle of arm lift when the arm is down is negative, and the angle of arm lift when the arm is up is positive. When the user's arm is raised from the horizontal position, the arm is raised at an angle greater than 0. The point in time when the angle of the arm lift reaches the angle threshold may be considered as the movement start point. The angle threshold may be −70° to −20°, or as a preference, the angle threshold may be −50° to −25°. In some embodiments, to further ensure the accuracy of a selected movement start point, the preset condition may also include that the angular velocity of the arm within a specific range of time after the movement start point may be greater than or equal to an angular velocity threshold. The angular velocity threshold may range from 5°/s~50°/s. According to preference of example, the angular velocity threshold may range from 10°/s~30°/s. For example, when a user performs a bent-over movement, the angular velocity of the arm is continuously greater than the angular velocity threshold for a specific time range (e.g., 0.05 s, 0.1 s, 0.5 s) after an angular threshold is reached and the user's arm is continuously raised upward. In some embodiments, if the angular velocity of the selected movement start point according to the preset condition is less than the angular velocity threshold within a specific range of time, the preset condition continues until a movement start point is determined.

In some embodiments, the movement middle point may be a point within one movement cycle from the start point. For example, when the user performs the seated chest press, a start point of the movement may be set to the time when the arms extend outward horizontally and begin to internally rotate, and the time when the arms come together may be determined as a movement middle point of the user. In some embodiments, the preset condition may be that a direction of the angular velocity at the point in time after the movement middle point changes relative to a direction of the angular velocity at the point in time before the movement middle point, and an angular velocity value at the movement middle point is approximately zero, wherein the direction of the angular velocity at the movement middle point is opposite to the direction of the angular velocity at the movement start point. In some embodiments, to improve the accuracy of the selection of the movement middle point, a change of the angular velocity (an acceleration of angular velocity) in a first specific time range after the movement middle point (e.g., 0.05 s, 0.1 s, 0.5 s) may be greater than an acceleration threshold of angular velocity (e.g., 0.05 rad/s). In some embodiments, the amplitude information in the electromyographic signal corresponding to the movement middle point may be greater than the electromyographic threshold while the movement middle point satisfies the preset condition described above. Since the different movements correspond to different electromyographic signals, the electromyographic threshold may be related to the user movement and the target electromyographic signal. In the seated chest press, the electromyographic signal at the pectoral muscle may be the target electromyographic signal. In some embodiments, the position corresponding to the movement middle point (also may be called as "middle position") may be approximated as the maximum point of muscle force, where the electromyographic signal may have a relatively great value. It should be noted that the electromyographic signal at the part of the user's body when the user performs the movement during motion may be substantially higher than the electromyographic signal at the part of the user's body when the user does not perform the movement during motion (when the muscle in the particular part may be considered as a resting state). For example, an amplitude of the electromyographic signal at the part of the user's body when the user's movement reaches the middle position may be 10 times higher than that in the resting state. In addition, the relationship between the amplitude of the electromyographic signal at the part of the user when the movement position reaches the middle position (the movement middle point) and the amplitude of the electromyographic signal in the resting state may be different according to the different movement types performed by the user, and the relationship between the two may be adapted according to the actual movement. In some embodiments, to improve the accuracy of the selection of the movement middle point, the amplitude corresponding to a second specific time range after the movement middle point (e.g., 0.05 s, 0.1 s, 0.5 s) may be continuously greater than the electromyographic threshold. In some embodiments, in addition to the above preset condition (e.g., the angular velocity and an amplitude condition of the electromyographic signal), a Euler angle (also referred to as an angle) of the movement middle point and the start position may satisfy a certain condition preset to determine the movement middle point. For example, in the seated chest press, the Euler angle at the movement middle point relative to the movement start point may be greater than one or more Euler angle thresholds (also referred to as angle thresholds). For example, with a front-to-back direction of the human body as an X-axis, a left-right direction of the human body as a Y-axis, and a height direction of the human body as a Z-axis, a Euler angle changed in the X and Y directions may be less than 25°, and the Euler angle changed in the Z direction may be greater than 40° (the movement of the seated chest press is mainly related to the rotation at the Z-axis direction, the above parameters are only reference examples). In some embodiments, the electromyographic thresholds and/or the Euler angle thresholds may be stored in advance in a storage device or a hard drive of the wearable device 130, or in the processing device 110, or may be determined based on an actual condition and adjusted in real time.

In some embodiments, the processing module 220 may determine, based on the time domain window of the electromyographic signal or the attitude signal, the movement middle point from a time domain window at a time point after the movement start point according to a preset condition. In some embodiments, after the movement middle point is determined, whether there are other time points that meet the preset condition within the time range from the movement start point to the movement middle point may be re-verified, and if so, a movement start point closest to the movement middle point may be selected as the best movement start point. In some embodiments, if the difference between the time of the movement middle point and the time of the movement start point is greater than a specific time threshold (e.g., ½ or ⅔ of a movement cycle), the movement middle point may be invalid, and the movement start point and movement middle point may be re-determined based on preset condition.

In some embodiments, the movement end point may be a time point that is after the movement middle point, and within one movement cycle from the movement start point. For example, the movement end point may be set as a point that is one movement cycle from the movement start point, and the movement end point herein may be considered as an end of a movement cycle of the user. For example, when the user performs the seated chest press, the movement start point may be set as a time point when the arms extend horizontally to the left and right and start internal rotation, the time point when the arms close together may be the movement middle point of the user, and the time point when the arms return to the extended state again from the horizontal direction may correspond to the movement end point of the user. In some embodiments, the preset condition may be that a changed angular velocity value corresponding to the attitude signal is an extreme value. In some embodiments, to prevent jitter misjudgment, the change in Euler angle should exceed a certain Euler angle threshold, e.g., 20°, in the time range from the movement middle point to the movement end point. In some embodiments, the processing module 220 may determine the movement end point from the time domain window after the movement middle point based on the time domain windows of the electromyographic signal and the attitude signal according to the preset condition. In some embodiments, if the difference between the time of the movement end point and the time of the movement middle point is greater than a specific time threshold (e.g., ½ of a movement cycle), the movement start point and the movement middle point may be invalid, and the movement start point, the movement middle point, and the movement end point may be re-determined based on the preset condition.

In some embodiments, at least one set of the movement start point, the movement middle point, and the movement end point in the movement signal may be repeatedly determined, and the movement signal may be segmented based on the at least one set of the movement start point, the movement middle point, and the movement end point as the target feature points. The step may be performed by the processing module 220 and/or the processing device 110. It should be noted that the segmentation of the movement signal is not limited to be based on the above movement start point, the movement middle point and the movement end point, but may also include other time points. For example, for the seated chest press, 5 time points may be selected according to the above steps, a first time point may be a movement start point, a second time point may be a moment of the maximum angular velocity of the internal rotation, a third time point may be the movement middle point, a fourth time point may be the moment of the maximum angular velocity of external rotation, a fifth time point may be the moment when the arms return to extend left and right, and the angular velocity is 0, that is, the movement end point. In this example, compared to the movement start point, the movement middle point and the movement end point in the above steps, the second time point is added as a ¼ marker point of the movement cycle, the movement end point described in the above embodiments is used as the fourth time point for marking the ¾ position of the movement cycle, and the fifth time point is added as an end point of the complete movement. For the seated chest press, more time points are used here, and a recognition of the movement quality may be done based on the signal of the first ¾ of the movement cycle (i.e., the recognition of the movement quality for a single cycle does not depend on a complete analysis of the signal of a whole cycle), which may complete the monitoring and feedback of the user's movement without the end of a current cycle. At same time, all signals of the process of the whole movement may be completely recorded to be easily uploaded to the cloud or the mobile terminal device, thus more methods may be adopted to monitor the user's movement. For more complex movement, the cycle of the movement may be quite long, and each stage may have different force patterns. In some embodiments, the above method for determining each time point may be adopted to divide the movement into multiple stages, and the signal for each stage may be recognized and fed back separately to improve timeliness of feedback of the user's movement.

It should be noted that the above segmentation and monitoring of the movement signal based on the movement start point, movement middle point and movement end point as a set of target feature points is only an exemplary illustration. In some embodiments, the user's movement signal may also be segmented and monitored based on any one or more of the movement start point, the movement middle point and the movement end point as the target feature points. For example, the movement signal may be segmented and monitored by using the movement start point as the target feature point. As another example, the movement start point and the movement end point may be used as a set of target feature points to segment and monitor the movement signal, and other time points or time ranges that can be used as the target feature points are within the scope of protection of the present disclosure.

It should be noted that the above description of the process 700 is for example and illustration purposes only and does not limit the scope of application of the present disclosure. For those skilled in the art, various amendments and changes can be made to the process 700 under the guidance of the present disclosure. However, these amendments and changes are still within the scope of the present disclosure. For example, step 710 and step 720 may be performed simultaneously by the processing module 220. As another example, step 710 and step 720 may be performed simultaneously by the processing module 220 and the processing device 110, respectively.

Figure 8:
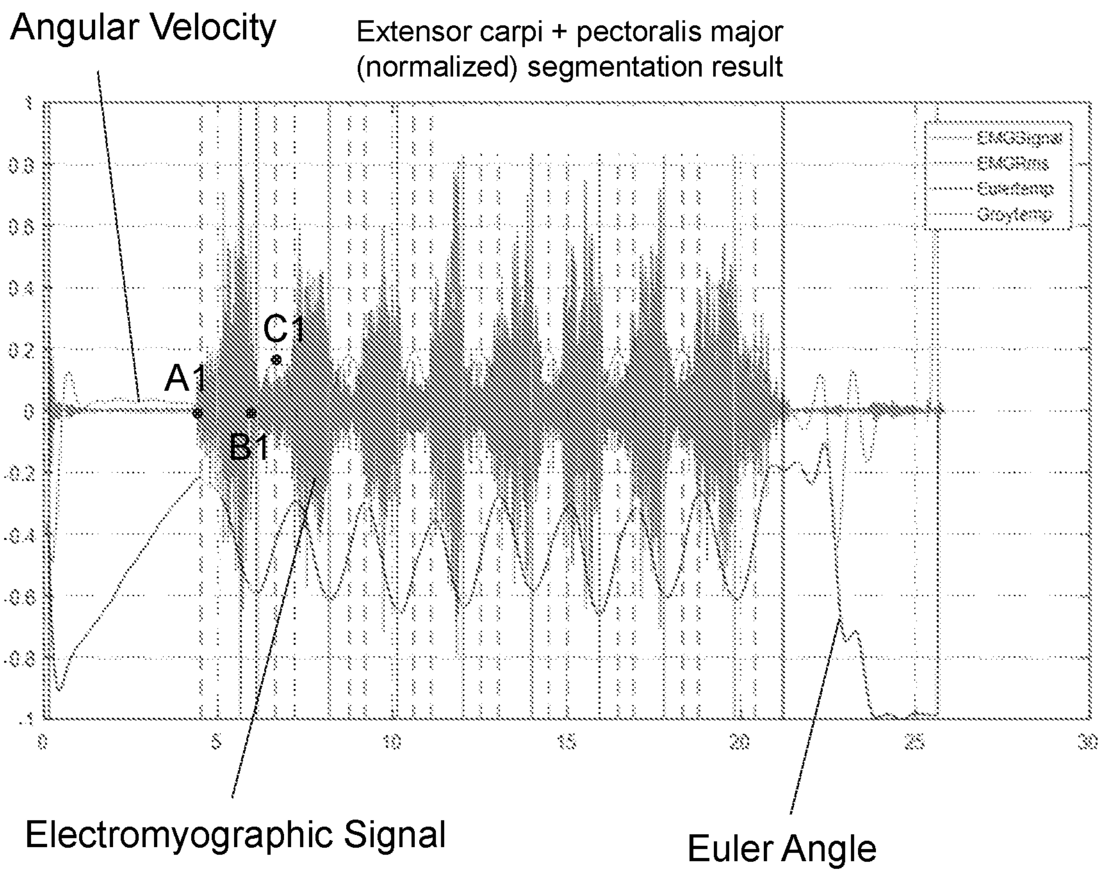
FIG. 8 is a diagram illustrating exemplary normalized results of segmenting a movement signal according to some embodiments of the present disclosure.

FIG. 8 is a diagram illustrating exemplary movement signal segmentation according to some embodiments of the present disclosure. A horizontal coordinate in FIG. 8 may indicate a motion time of a user, and a vertical coordinate may indicate amplitude information of an electromyographic signal of a muscle part (e.g., pectoralis major) during seated chest press. FIG. 8 may also include an angular velocity curve and a Euler angle curve corresponding to an attitude signal of the wrist position of the user during motion. The angular velocity curve is configured to represent a velocity change of the user during motion and the Euler angle curve is configured to represent a position situation of a user's body part during motion. As shown in FIG. 8, point A1 is determined as the movement start point according to the preset condition. Specifically, a direction of the angular velocity at a time point after the user's movement start point A1 changes relative to the direction of the angular velocity at a time point before the movement start point A1. Further, the angular velocity value at the movement start point A1 is approximately 0, and an acceleration value of the angular velocity at the movement start point A1 is greater than 0.

Refer to FIG. 8, point B1 is determined as the movement middle point according to the preset condition. Specifically, the direction of the angular velocity at the time point after the user's movement middle point B1 changes relative to the direction of the angular velocity at the time point before the movement middle point B 1, and the angular velocity value at the movement middle point B1 is approximately 0. The direction of the angular velocity at the movement middle point B1 is opposite to the direction of the angular velocity at the movement start point A1. In addition, the amplitude of the electromyographic signal (shown as the "electromyographic signal" in FIG. 8) corresponding to the movement middle point B1 is greater than the electromyographic threshold.

Continue to refer to FIG. 8, point Cl is determined as the movement end point according to the preset condition. Specifically, a changed angular velocity value at the movement end point Cl is the extreme value from the movement start point A1 to the movement end point Cl. In some embodiments, the process 700 may complete the movement segmentation shown in FIG. 8, such that the movement signal from the movement start point A1 to the movement end point Cl shown in FIG. 8 may be considered as a segment of the motion.

It is noted that, in some embodiments, if a time interval between the movement middle point and the movement start point is greater than a specific time threshold (e.g., ½ of a movement cycle), the processing module 220 may re-determine the movement start point to improve the accuracy of the movement segmentation. The specific time threshold here may be stored in a storage device or a hard drive of the wearable device 130, or in the processing device 110, or may be determined or adjusted based on the actual situation of the user during motion. For example, if the time interval between the movement start point A1 and the movement middle point B1 in FIG. 8 is greater than a specific time threshold, the processing module 220 may re-determine the movement start point, thereby improving the accuracy of the movement segmentation. In addition, the segmentation of the movement signal is not limited to be based on the above movement start point A1, the movement middle point B1 and the movement end point Cl, but may also include other time points, and the selection of the time points may be made according to the complexity of the movement.

When obtaining the user's movement signal, other physiological parameter information of the user (e.g., a heart rate signal), an external condition such as a relative movement of the obtaining module 210 and the human body during motion or a compression of the obtaining module 210 may affect the quality of the movement signal, for example, resulting in an abrupt change in the electromyographic signal, thereby affecting the monitoring of the movement. For ease of description, an abrupt electromyographic signal may be described by using a singularity, and an exemplary singularity may include a burr signal, a discontinuous signal, etc. In some embodiments, monitoring the movement of the user during motion based at least on the feature information corresponding to the electromyographic signal or the feature information corresponding to the attitude signal may further include: pre-processing the electromyographic signal in a frequency domain or a time domain, obtaining, based on the preprocessed electromyographic signal, the feature information corresponding to the electromyographic signal, and monitoring, based on the feature information corresponding to the electromyographic signal or the feature information corresponding to the attitude signal, the movement of the user during motion. In some embodiments, pre-processing the electromyographic signal in the frequency domain or the time domain may include filtering the electromyographic signal in the frequency domain to select or retain components of the electromyographic signal in a particular frequency range in the frequency domain. In some embodiments, the obtaining module 210 may obtain an electromyographic signal in a frequency range of 1 Hz-1000 Hz, filter the electromyographic signal, and select an electromyographic signal in a specific frequency range (e.g., 30 Hz-150 Hz) for subsequent processing. In some embodiments, the specific frequency range may be 10 Hz-500 Hz. According to preference of example, the specific frequency range may be 15 Hz-300 Hz or 30 Hz-150 Hz. In some embodiments, a filtering process may include a low-pass filter processing. In some embodiments, the low-pass filter may include an LC passive filter, an RC passive filter, an RC active filter, a passive filter composed of special elements. In some embodiments, the passive filter composed of the special elements may include one or more of a piezoelectric ceramic filter, a crystal filter, an acoustic surface filter. It should be noted that the specific frequency range is not limited to the above range, but may also be other ranges, which may be selected according to the actual situation. More descriptions for monitoring, according to the feature information corresponding to the electromyographic signal or the feature information corresponding to the attitude signal, the movement of the user during motion may be found in FIG. 5, FIG. 6 of the present disclosure and their relevant descriptions.

In some embodiments, pre-processing the electromyographic signal in the frequency domain or the time domain may further include signal correction processing of the electromyographic signal in the time domain. The signal correction processing refers to a correction to the singularity (e.g., the burr signal, the discontinuous signal, etc.) in the electromyographic signal. In some embodiments, the signal correction processing of the electromyographic signal in the time domain may include determining the singularity in the electromyographic signal, i.e., determining the abrupt signal in the electromyographic signal. The singularity may be a sudden change in the amplitude of an electromyographic signal within a certain moment, causing a discontinuity in the signal. As another example, the electromyographic signal is morphologically smooth and there is no abrupt change in the amplitude of the electromyographic signal, but there is the abrupt change in the first-order differential of the electromyographic signal, and the first-order differential is discontinuous. In some embodiments, the method for determining the singularity in the electromyographic signal may include, but is not limited to, one or more of a Fourier transform, a wavelet transform, a fractal dimension, etc. In some embodiments, the signal correction processing of the electromyographic signal in the time domain may include removing the singularity in the electromyographic signal, for example, removing signals within a period of time at and near the singularity. Alternatively, the signal correction processing of the electromyographic signal in the time domain may include correcting the singularity of the electromyographic signal according to the feature information of the electromyographic signal in the specific time range, such as adjusting the amplitude of the singularity based on the signals around the singularity. In some embodiments, the feature information of the electromyographic signal may include the amplitude information, the statistic information of the amplitude information, etc. The statistic information of amplitude information (also referred to as an amplitude entropy) refers to a distribution of the amplitude information of the electromyographic signal in the time domain. In some embodiments, after a location (e.g., the time point) of the singularity in the electromyographic signal is determined by a signal processing algorithm (e.g., the Fourier transform, the wavelet transform, the fractal dimension), the singularity may be corrected based on the electromyographic signal in the specific time range before or after the location of the singularity. For example, when the singularity is an abrupt trough, the electromyographic signal at the abrupt trough may be supplemented based on the feature information (e.g., the amplitude information, the statistic information of the amplitude information) of the electromyographic signal in a specific time range (e.g., 5 ms-60 ms) before or after the abrupt trough.

Figure 9:
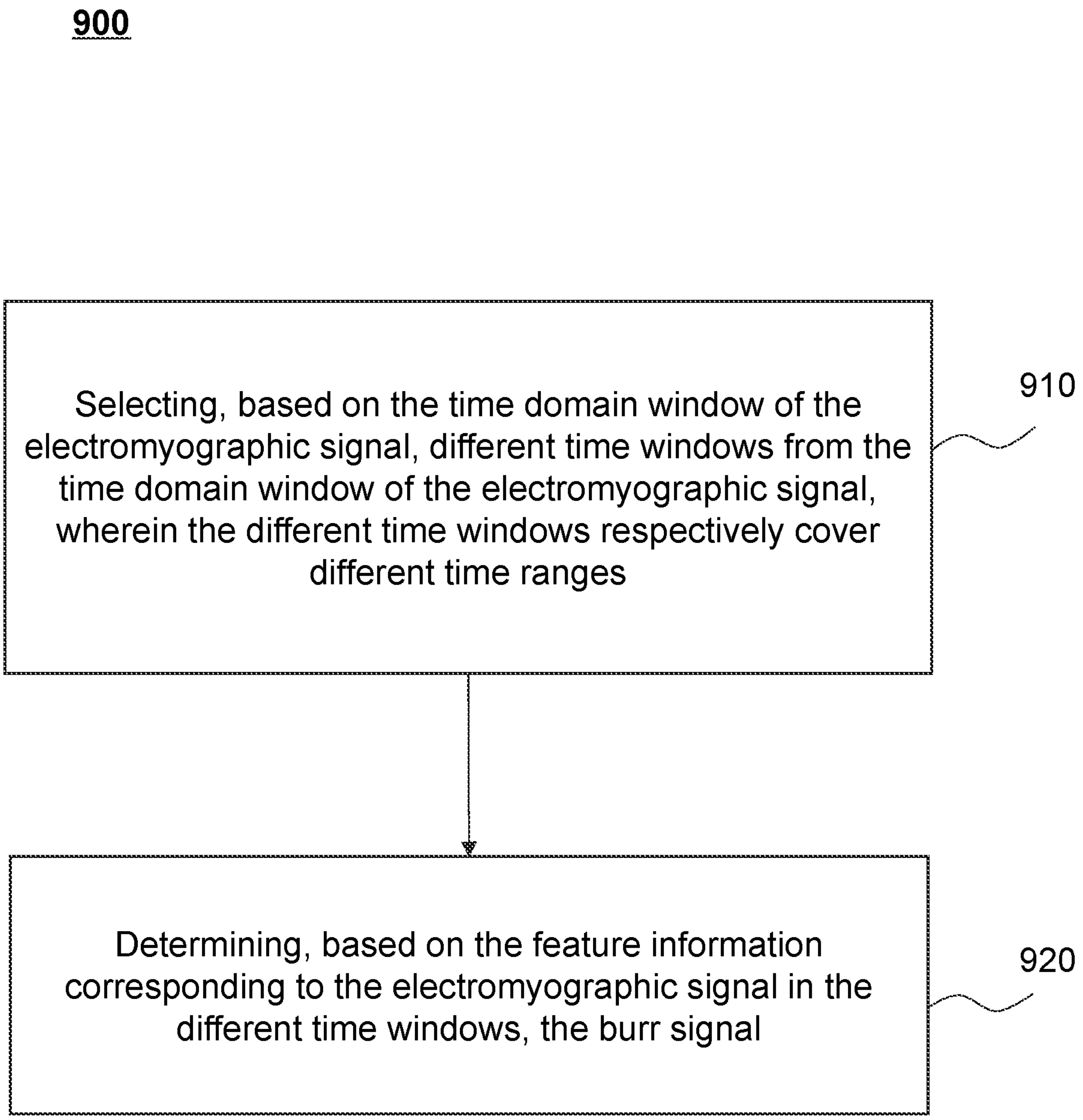
FIG. 9 is a flowchart of an exemplary process for preprocessing an electromyographic signal according to some embodiments of the present disclosure.

Exemplary illustration with the singularity as the burr signal, FIG. 9 is a flowchart of an exemplary process for pre-processing an electromyographic signal according to some embodiments of the present disclosure. As shown in FIG. 9, the process 900 may include following steps.

In step 910, different time windows may be selected from the time domain window of the electromyographic signal based on the time domain window of the electromyographic signal, wherein the different time windows may cover different time ranges, respectively.

In some embodiments, the step may be performed by the processing module 220 and/or the processing device 110. In some embodiments, the different windows may include at least one specific window. The specific window refers to a window with a specific time length selected from the time domain window. For example, when the time length of the time domain window of the electromyographic signal is 3 s, a time length of the specific window may be 100 ms. In some embodiments, the specific window may include a plurality of different time windows. Merely as way of exemplary illustration, the specific window may include a first time window and a second time window. The first time window may refer to a window corresponding to a partial time length of the specific window. For example, when the time length of the specific window is 100 ms, the time length of the first time window may be 80 ms. The second time window may be another window corresponding to the partial time length of the specific window. For example, when the specific window is 100 ms, the second time window may be 20 ms. In some embodiments, the first time window and the second time window may be consecutive time windows within a same specific window. In some embodiments, the first time window and the second time window may also be two discrete or overlapping time windows within the same specific window. For example, when the time length of the specific window is 100 ms, the time length of the first time window may be 80 ms and the time length of the second time window may be 25 ms. In this situation, the second time window may be overlapped with the first time window in 5 ms. In some embodiments, the processing module 220 may slide and update the specific window sequentially from an initially time point of the time domain window of the electromyographic signal according to the specific time length based on the time domain window of the electromyographic signal, and may continue to divide an updated specific window into the first time window and the second time window. The specific time length mentioned here may be less than 1 s, 2 s, 3 s, etc. For example, the processing module 220 may select a specific window of a specific time length of 100 ms and divide that specific window into a first time window of 80 ms and a second time window of 20 ms. Further, the specific window may be updated by sliding along the time direction. A sliding distance here may be a time length of the second time window (e.g., 20 ms) or other suitable time lengths, e.g., 30 ms, 40 ms, etc.

In step 920, the burr signal may be determined based on the feature information corresponding to the electromyographic signal in the different time windows.

In some embodiments, the step may be performed by the processing module 220 and/or the processing device 110. In some embodiments, the feature information corresponding to the electromyographic signal may include at least one of the amplitude information, the statistic information of the amplitude information. In some embodiments, the processing module 220 may obtain the amplitude information or the statistic information of the amplitude information corresponding to the electromyographic signal in different time windows (e.g., the first time window, the second time window) to determine the location of the burr signal. Detailed descriptions for determining, based on the feature information corresponding to the electromyographic signal in different time windows, the location of the burr signal may be found in FIG. 10 and its relevant descriptions.

It should be noted that the above description of the process 900 is for example and illustration purposes only and does not limit the scope of application of the present disclosure. For those skilled in the art, various amendments and changes can be made to process 900 under the guidance of the present disclosure. For example, the specific window is not limited to include the first time window and the second time window described above, but may also include other time windows, for example, a third time window, a fourth time window, etc. In addition, the specific range of moments before or after the position of the burr signal may be adapted according to the length of the burr signal, which may not be further limited herein. However, these amendments and changes are still within the scope of the present disclosure.

Figure 10:
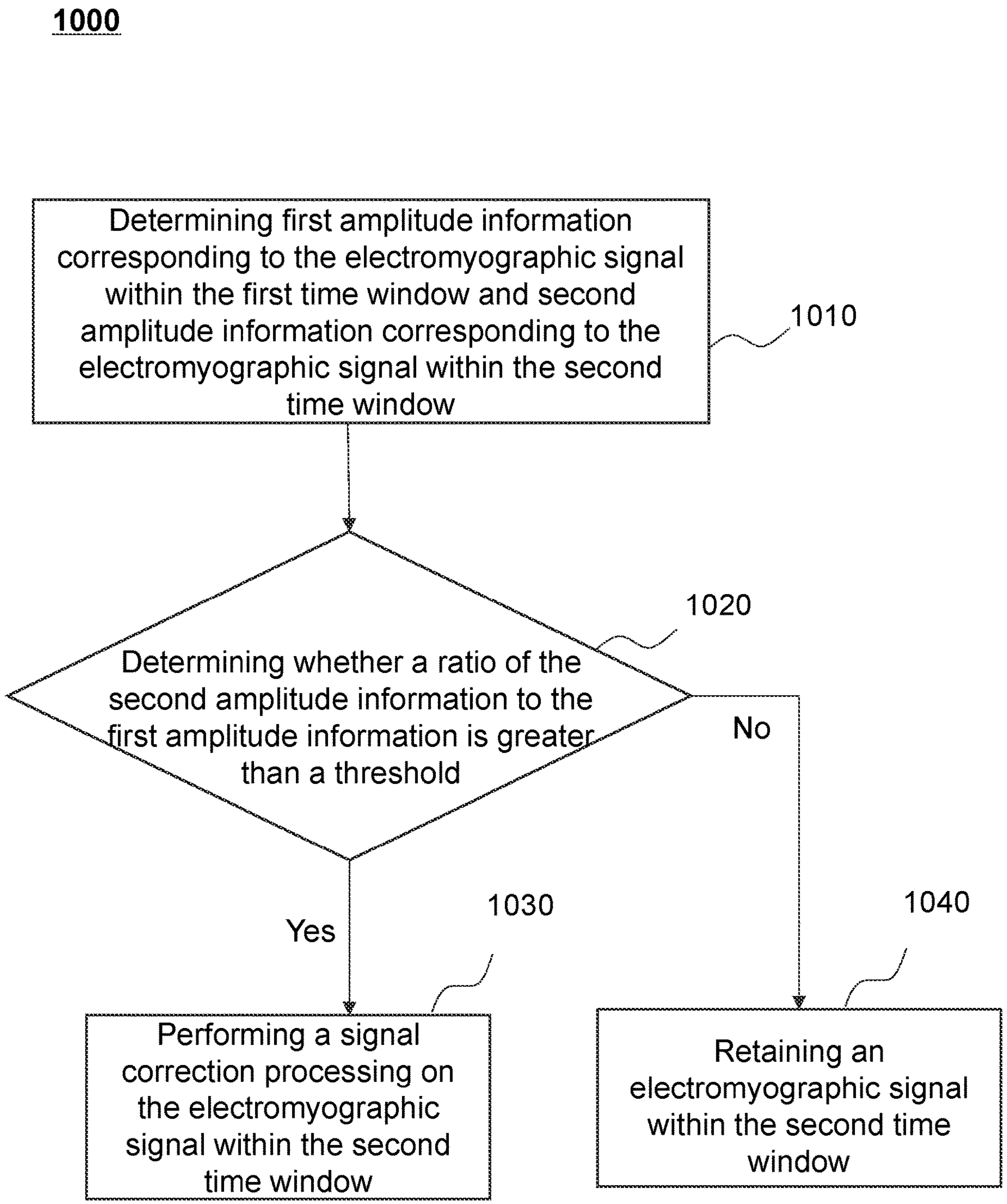
FIG. 10 is a flow chart illustrating an exemplary burr signal according to some embodiments of the present disclosure.

FIG. 10 is a flowchart illustrating an exemplary process for determining a burr signal according to some embodiments of the present disclosure. As shown in FIG. 10, process 1000 may include the following steps.

In step 1010, first amplitude information corresponding to the electromyographic signal within the first time window and second amplitude information corresponding to the electromyographic signal within the second time window may be determined.

In some embodiments, the step may be performed by the processing module 220 and/or the processing device 110. In some embodiments, the processing module 220 may select the time lengths of the first time window and the second time window, and extract the first amplitude information corresponding to the electromyographic signal during the time length of the first time window and the second amplitude information corresponding to the electromyographic signal during the time length of the second time window. In some embodiments, the first amplitude information may include an average amplitude of the electromyographic signal during the first time window, and the second amplitude information may include the average amplitude of the electromyographic signal during the second time window. For example, the processing module 220 may select a time length of a first time window as 80 ms, and extract the first amplitude information corresponding to the electromyographic signal within the first time window. The processing module 220 may select a time length of a second time window as 20 ms, and extract the second amplitude information corresponding to the electromyographic signal within the second time window.

In some embodiments, a selection of the time length of the first time window and the time length of the second time window may be related to the shortest burr signal length and amount of computation of the system. In some embodiments, the time length of the first time window and the time length of the second time window may be selected according to the feature of the burr signal. The time length of an electro-cardio burr signal is 40 ms-100 ms, the time interval between two burr signals in the electro-cardio signal may be about 1 s, a peak point of the burr signal is basically symmetrical on both sides, an amplitude distribution of the burr signal is relatively even on both sides, etc. In some embodiments, when the burr signal is the electro-cardio signal, a time length less than the length of the burr signal, e.g., a half of the length of the burr signal, may be selected as the time length of the second time window, and the time length of the first time window may be greater than (e.g., four times) the time length of the second time window. In some embodiments, the time length of the first time window may be within a range of an interval (about 1 s) between burr signals minus the time length of the second time window. It should also be noted that the above selected time length of the first time window and the time length of the second time window are not limited to the above description, as long as a sum of the time length of the second time window and the time length of the first time window is less than a time interval of adjacent two burr signals, or the time length of the second time window is less than a single burr signal length, or an amplitude of the electromyographic signal within the second time window and an amplitude of the electromyographic signal the first time window have a good discrimination.

In step 1020, a determination may be made as whether a ratio of the second amplitude information to the first amplitude information is greater than a threshold.

In some embodiments, the step may be performed by the processing module 220 and/or the processing device 110. In some embodiments, the processing module 220 may determine whether the ratio of the second amplitude information corresponding to the electromyographic signal in the second time window to the first amplitude information corresponding to the electromyographic signal in the first time window is greater than the threshold. The threshold here may be stored in a storage device or a hard drive of the wearable device 130, or in the processing device 110, or may be adjusted according to an actual situation. In some embodiments, if the processing module 220 determines that the ratio of the second amplitude information to the first amplitude information is greater than the threshold, step 1020 may proceed to step 1030. In other embodiments, if the processing module 220 determines that the ratio of the second amplitude information to the first amplitude information is not greater than the threshold, step 1020 may proceed to step 1040.

In step 1030, a signal correction processing may be performed on the electromyographic signal within the second time window.

In some embodiments, the step may be performed by the processing module 220 and/or the processing device 110. In some embodiments, the processing module 220 may perform the signal correction processing on the electromyographic signal within the second time window based on a comparison result of the ratio of the second amplitude information to the first amplitude information and the threshold in step 1020. For example, in some embodiments, if the ratio of the second amplitude information to the first amplitude information is greater than the threshold, then the electromyographic signal in the second time window corresponding to the second amplitude information may be a burr signal. In some embodiments, processing the electromyographic signal within the second time window may include performing a signal correction processing on the electromyographic signal within the second time window based on the electromyographic signal within a specific time range before or after the second time window. In some embodiments, the signal correction processing of the electromyographic signal within the second time window may include, but is not limited to, a padding, an interpolation, etc. In some embodiments, the specific time range herein may be 5 ms-60 ms. According to preference of example, the specific time range may be 10 ms-50 ms or 20 ms-40 ms. It should be noted that the specific time range is not limited to the above range, for example, the specific time range may be greater than 60 ms, less than 5 ms, or other ranges. In practical application scenarios, the specific time range may be adapted based on the duration of the burr signal.

In step 1040, an electromyographic signal within the second time window may be retained.

In some embodiments, the step may be performed by the processing module 220 and/or the processing device 110. In some embodiments, the processing module 220 may perform a retention on the electromyographic signal within the second time window according to the comparison result of the ratio of the second amplitude information to the first amplitude information and the threshold in step 1020. For example, in some embodiments, when the ratio of the second amplitude information to the first amplitude information is not greater than the threshold, then the electromyographic signal within the second time window corresponding to the second amplitude information may be a normal electromyographic signal, and the normal electromyographic signal may be retained, i.e., the electromyographic signal within the second time window may be retained.

It should be noted that the amplitude of the electromyographic signal is gradually increasing since electrical charges gradually accumulates during muscular exertion, so that the amplitude of the electromyographic signal within two adjacent time windows (e.g., the first time window and the second time window) does not change abruptly in the absence of a burr signal. In some embodiments, whether there is the burr signal in the electromyographic signal may be determined and the burr signal may be removed according to the process 1000, to realize a real-time processing of the burr signal, thereby enabling the wearable device 130 or the mobile terminal device 140 to provide a real-time feedback of the motion state to the user, and helping the user to perform motion more scientifically.

In some embodiments, the time length corresponding to the first time window may be greater than the time length corresponding to the second time window. In some embodiments, a specific time length corresponding to a specific window may be less than 1 s. In some embodiments, the ratio of the time length corresponding to the first time window to the time length corresponding to the second time window may be greater than 2. In some embodiments, the time length corresponding to the first time window, the time length corresponding to the second time window, and the specific time length corresponding to the specific window may be selected to ensure that the shortest burr signal (e.g., 40 ms) can be removed, and the system has a high signal-to-noise ratio, the calculation volume of the system may be decreased, repeated calculation of the system may be avoided, and the time complexity may be reduced, thereby improving the calculation efficiency and the calculation accuracy of the system.

It should be noted that the above description of the process 1000 is for example and illustration purposes only, and does not limit the scope of application of the present disclosure. For those skilled in the art, various amendments and changes may be made to process 1000 under the guidance of the present disclosure. For example, the above process 1000 is only an example where the singularity is the burr signal, and when the singularity is a trough signal, each of the above steps (e.g., step 1010, step 1020, step 1030, etc.) and the technical schemes may be adjusted or other methods may be used to perform the signal correction processing. However, these amendments and changes are still within the scope of the present disclosure.

In some embodiments, the signal correction processing may further be performed on the singularity of the electromyographic signal by the other methods, e.g., a high-pass method, a low-pass method, a band-pass method, a wavelet transform reconstruction method, etc. In some embodiments, for an application scenario where a low-frequency signal is not sensitive, a 100 Hz high-pass filter may be used for a removal of the burr signal. In some embodiments, in addition to the signal correction processing of the electromyographic signal, the other methods of the signal processing of the electromyographic signal, such as a filtering processing, a signal amplification, a phase adjustment, etc., may also be performed. In some embodiments, the electromyographic signal of the user collected by the electromyographic sensor may be converted into a digital electromyographic signal by an analog-to-digital converter (ADC), and the converted digital electromyographic signal may be subjected to a filtering process, which may filter out an industrial frequency signal and its harmonic signal, etc. In some embodiments, the processing of the electromyographic signal may further include removing motion artifacts of the user. The motion artifacts here refer to signal noises generated by a relative movement of the muscles at the position to be measured relative to the electromyographic module during an obtaining process of the electromyographic signal while the user in motion.

In some embodiments, the attitude signal may be obtained by the attitude sensor on the wearable device 130. The attitude sensor on the wearable device 130 may be distributed on the limb areas (e.g., the arms, the legs, etc.), the trunk areas (e.g., the chest, the abdomen, the back, the waist, etc.), and the head, etc. The attitude sensor may enable the collection of the attitude signal from other parts of the body such as the limb parts and the trunk parts. In some embodiments, the attitude sensor may be a sensor of an attitude and heading reference system (AHRS) with an attitude fusion algorithm. The attitude fusion algorithm may fuse data from a nine-axis inertial measurement unit (IMU) with a three-axis acceleration sensor, a three-axis angular velocity sensor, and a three-axis geomagnetic sensor into Euler angles or quaternions to obtain the attitude signal of the user's body part where the attitude sensor is located. In some embodiments, the processing module 220 and/or the processing device 110 may determine the feature information corresponding to the attitude based on the attitude signal. In some embodiments, the feature information corresponding to the attitude signal may include, but is not limited to, the value of angular velocity, the direction of angular velocity, the acceleration value of angular velocity, etc. In some embodiments, the attitude sensor may be a strain sensor. The strain sensor may obtain a bending direction and a bending angle at the user's joints, thereby obtaining the attitude signal during the user's motion. For example, the strain sensor may be set at the knee joint of the user. When the user is in motion, the user's body part acts on the strain sensor, and the bending direction and the bending angle at the knee joint of the user may be determined based on the change in resistance or length of the strain sensor, thereby obtaining the attitude signal of the user's leg. In some embodiments, the attitude sensor may also include a fiber optic sensor, and the attitude signal may be represented by a change in direction after bending of a fiber from the fiber optic sensor. In some embodiments, the attitude sensor may also be a magnetic flux sensor, and the attitude signal may be represented by transformation of the magnetic flux. It should be noted that the type of attitude sensor is not limited to the above sensors, but can also be other sensors, the sensors that can obtain the user's attitude signal are within the scope of the attitude sensor of the present disclosure.

Figure 11:
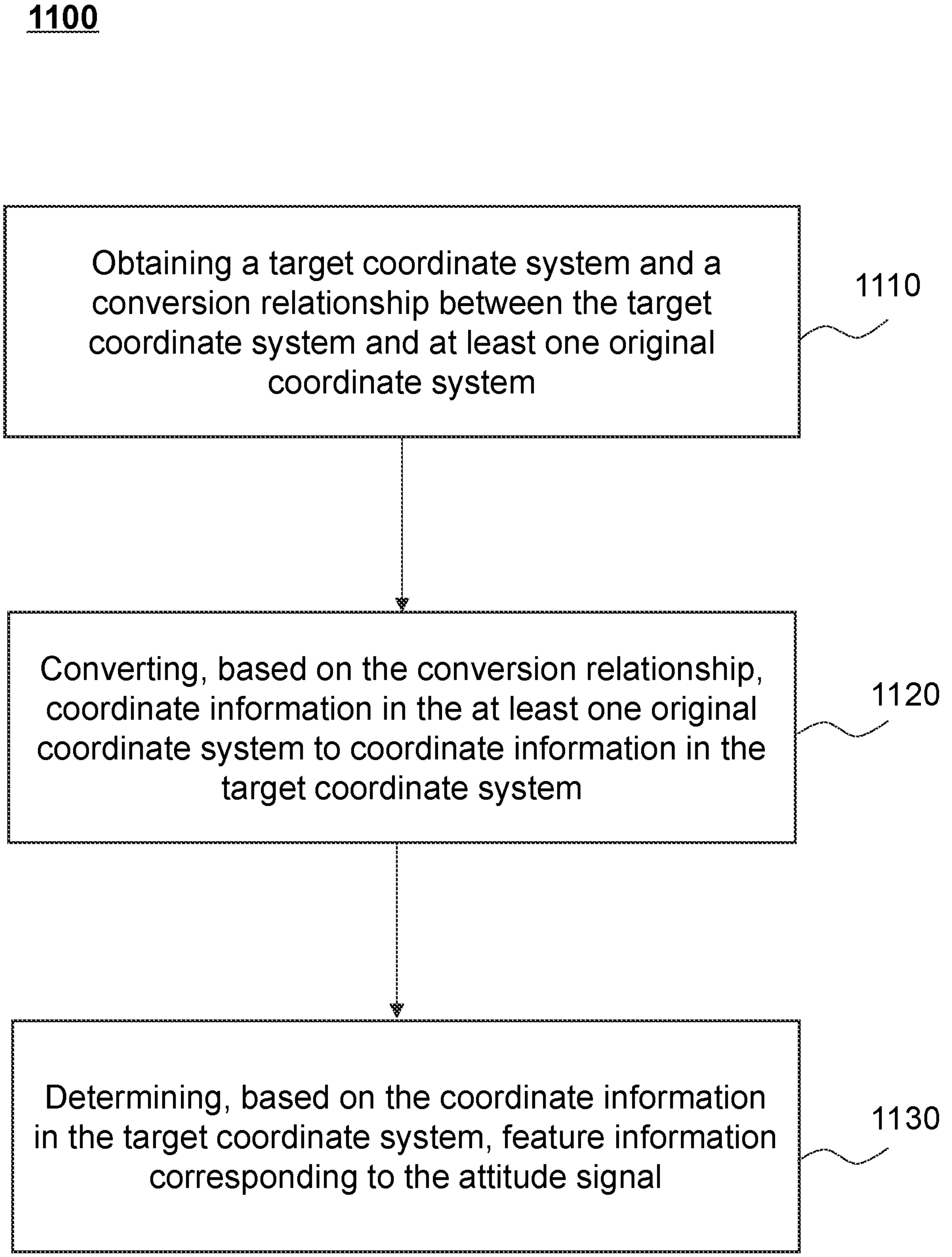
FIG. 11 is a flowchart of an exemplary process for determining feature information corresponding to an attitude signal according to some embodiments of the present disclosure.

FIG. 11 is a flowchart of an exemplary process for determining feature information corresponding to an attitude signal according to some embodiments of the present disclosure. As shown in FIG. 11, the process 1100 may include following steps.

In step 1110, a target coordinate system and a conversion relationship between the target coordinate system and at least one original coordinate system may be obtained.

In some embodiments, the step may be performed by the processing module 220 and/or the processing device 110. In some embodiments, the original coordinate system may be a coordinate system corresponding to the attitude sensor set on the human body. When the user uses the wearable device 130, each attitude sensor on the wearable device 130 is distributed on different parts of the human body, so that installation angles of the attitude sensors are different, and the attitude sensors in different parts use their own coordinate systems as the original coordinate systems, so the attitude sensors in different parts have different original coordinate systems. In some embodiments, an obtained attitude signal of the each attitude sensor may be represented in its corresponding original coordinate system. By transforming the attitude signal in different original coordinate systems into a same coordinate system (e.g., the target coordinate system), it is easy to determine a relative motion between different parts of the human body. In some embodiments, the target coordinate system refers to a human coordinate system established based on the human body. For example, a length direction of the human torso (i.e., a direction perpendicular to a transverse plane of the body) may be used as the Z-axis, an anterior-posterior direction of the human torso (i.e., a direction perpendicular to the coronal plane of the body) may be used as the X-axis, and a left-right direction of the human torso (i.e., a direction perpendicular to the sagittal plane of the body) may be used as the Y-axis in the target coordinate system. In some embodiments, there is a conversion relationship between the target coordinate system and the original coordinate system by which coordinate information in the original coordinate system may be converted to coordinate information in the target coordinate system. In some embodiments, the conversion relationship may be expressed as one or more rotation matrices. More descriptions for determining the conversion relationship between the target coordinate system and the original coordinate system may be found in FIG. 13 of the present disclosure and its relevant descriptions.

In step 1120, coordinate information in the at least one original coordinate system may be converted to coordinate information in the target coordinate system based on the conversion relationship.

In some embodiments, the step may be performed by the processing module 220 and/or the processing device 110. The coordinate information in the original coordinate system may be three-dimensional coordinate information in the original coordinate system. The coordinate information in the target coordinate system may be the three-dimensional coordinate information in the target coordinate system. Merely as way of exemplary illustration, the coordinate information $v_1$ in the original coordinate system may be converted to the coordinate information $v_2$ in the target coordinate system according to the conversion relationship. Specifically, a conversion between the coordinate information $v_1$ and the coordinate information $v_2$ may be performed by using a rotation matrix. The rotation matrix here may be understood as the conversion relationship between the original coordinate system and the target coordinate system. Specifically, the coordinate information $v_1$ in the original coordinate system may be converted to coordinate information $v_1-1$ using a first rotation matrix, the coordinate information $v_1-1$ may be converted to coordinate information $v_1-2$ using a second rotation matrix, and the coordinate information $v_1-2$ may be converted to coordinate information $v_1-3$ using a third rotation matrix. The coordinate information $v_1-3$ may be the coordinate information $v_2$ in the target coordinate system. It should be noted that the rotation matrices are not limited to the above first rotation matrix, the second rotation matrix and the third rotation matrix, but may also include fewer or more rotation matrices. In some alternative embodiments, the rotation matrix may be a rotation matrix or a combination of a plurality of rotation matrices.

In step 1130, the feature information corresponding to the attitude signal may be determined based on the coordinate information in the target coordinate system.

In some embodiments, the step may be performed by the processing module 220 and/or the processing device 110. In some embodiments, determining, based on the coordinate information in the target coordinate system, the feature information corresponding to the attitude signal may include determining, based on a plurality of coordinate information in the target coordinate system of the user during motion, the feature information corresponding to the attitude signal of the user. For example, when the user performs a seated chest press, the user's arm may correspond to the first coordinate information in the target coordinate system when the user's arm is held forward, and the user's arm may correspond to the second coordinate information in the target coordinate system when the user's arm is opened in a same plane as the torso. Based on the first coordinate information and the second coordinate information, the feature information, e.g., the angular velocity, the angular velocity direction, and the acceleration value of the angular velocity, corresponding to the attitude signal may be determined.

It should be noted that the above description of the process 1100 is for example and illustration purposes only and does not limit the scope of application of the present disclosure. For those skilled in the art, various amendments and changes can be made to process 1100 under the guidance of the present disclosure. However, these amendments and changes are still within the scope of the present disclosure.

Figure 12:
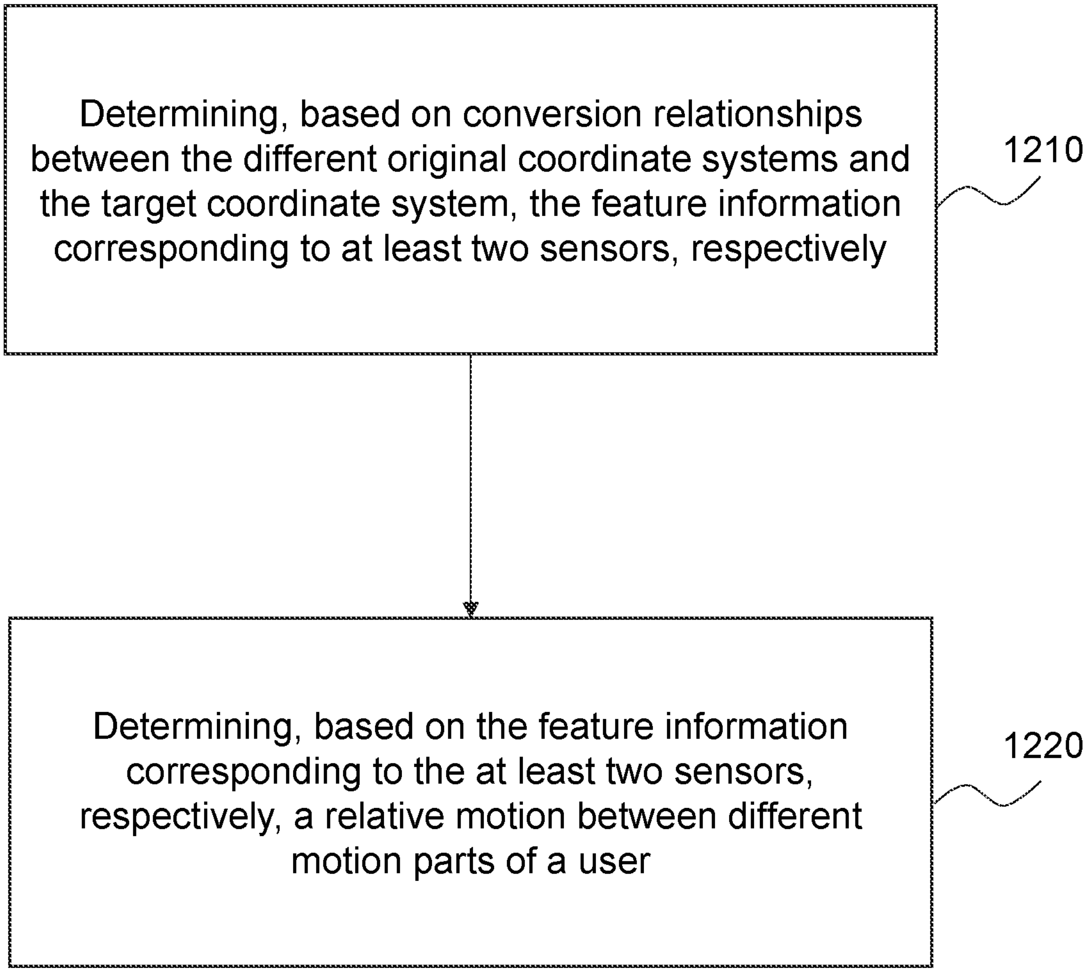
FIG. 12 is a flowchart of an exemplary process for determining relative motion between different motion parts of a user according to some embodiments of the present disclosure.

In some embodiments, the relative motion between different motion parts of the user's body may be determined based on the feature information corresponding to the attitude sensors located at the different motion parts of the user's body. For example, by using the feature information corresponding to the attitude sensor at the user's arm and the feature information corresponding to the attitude sensor at the user's torso, the relative motion between the user's arm and torso during motion may be determined. FIG. 12 is a flowchart of an exemplary process for determining relative motion between different motion parts of a user according to some embodiments of the present disclosure. As shown in FIG. 12, the process 1200 may include following steps.

In step 1210, feature information corresponding to at least two sensors respectively may be determined based on conversion relationships between different original coordinate systems and a target coordinate system.

In some embodiments, the step may be performed by the processing module 220 and/or the processing device 110. In some embodiments, due to different installation positions of different sensors at the human body, there are different conversion relationships between the original coordinate systems corresponding to the sensors and the target coordinate system. In some embodiments, the processing device 110 may convert the coordinate information in the original coordinate systems corresponding to the sensors at different parts of the user (e.g., small arm, large arm, torso, etc.) to the coordinate information in the target coordinate system, respectively, so that the feature information corresponding to at least two sensors may be determined respectively. More descriptions of the conversion of the coordinate information in the original coordinate system to coordinate information in the target coordinate system may be found elsewhere in the present disclosure, e.g., FIG. 11, which may not be repeated herein.

In step 1220, a relative motion between different motion parts of a user may be determined based on the feature information corresponding to the at least two sensors respectively.

In some embodiments, the step may be performed by the processing module 220 and/or the processing device 110. In some embodiments, a motion part may refer to a limb on the human body that can move independently, for example, a small arm, a large arm, a small leg, a thigh, etc. Merely as way of exemplary illustration, when the user performs an arm lifting dumbbell, the coordinate information in the target coordinate system corresponding to the sensor set at the small arm part and the coordinate information in the target coordinate system corresponding to the sensor set at the large arm part may be combined to determine the relative motion between the small arm and the large arm of the user, thereby determining the arm lifting dumbbell movement of the user.

In some embodiments, a same motion part of the user may be arranged with a plurality of sensors of the same or different types, and the coordinate information in the original coordinate systems corresponding to a plurality of sensors of same or different types may be converted to the coordinate information in the target coordinate system, respectively. For example, a plurality of sensors of the same or different types may be arranged at different locations of the user's small arm part, and a plurality of coordinates in the target coordinate systems corresponding to a plurality of sensors of the same or different types may simultaneously represent the movement of the user's small arm part. For example, the coordinate information in the target coordinate systems corresponding to a plurality of sensors of the same type may be averaged, thereby improving the accuracy of the coordinate information of the motion parts during the user's motion. For example, the coordinate information in the target coordinate system may be obtained by performing a fusion algorithm (e.g., Kalman filtering, etc.) on the coordinate information in coordinate systems corresponding to a plurality sensors of different types.

It should be noted that the above description of the process 1100 is for example and illustration purposes only and does not limit the scope of application of the present disclosure. For those skilled in the art, various amendments and changes can be made to process 1100 under the guidance of the present disclosure. However, these amendments and changes are still within the scope of the present disclosure.

Figure 13:
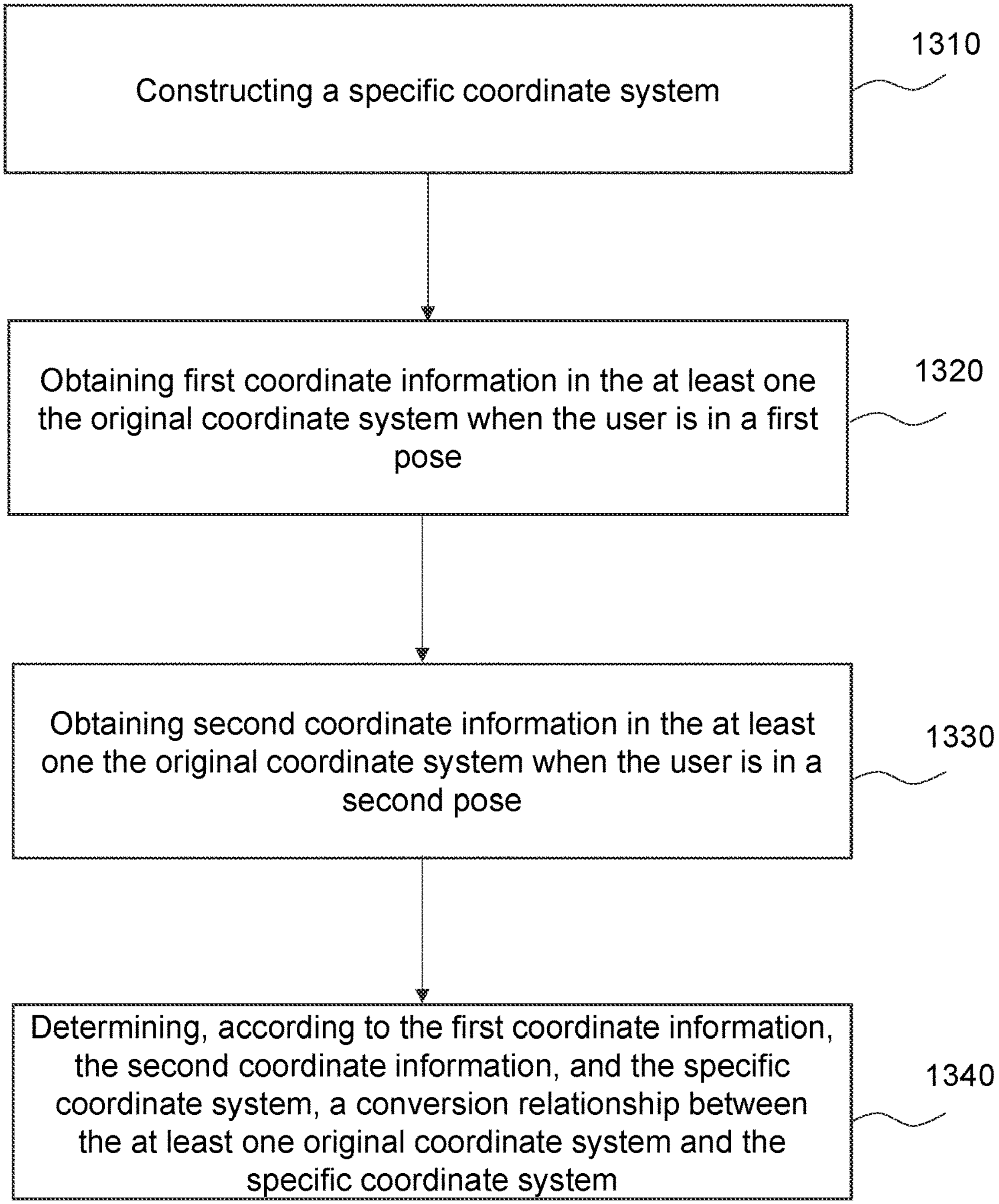
FIG. 13 is a flowchart of an exemplary process for determining a conversion relationship between an original coordinate system and a particular coordinate system according to some embodiments of the present disclosure.

FIG. 13 is a flowchart of an exemplary process for determining a conversion relationship between an original coordinate system and a specific coordinate system according to some embodiments of the present disclosure. In some embodiments, the process for determining the conversion relationship between the original coordinate system and the specific coordinate system may also be referred to as a calibration process. As shown in FIG. 13, the process 1300 may include following steps.

In step 1310, a specific coordinate system may be constructed.

In some embodiments, the step may be performed by the processing module 220 and/or the processing device 110. In some embodiments, the conversion relationship between at least one original coordinate system and the target coordinate system may be obtained by the calibration process. The specific coordinate system may refer to a reference coordinate system configured to determine the conversion relationship between the original coordinate system and the target coordinate system during the calibration process. In some embodiments, in a constructed specific coordinate system, a length direction of the torso when the human body is standing may be determined as the Z-axis, a front-to-back direction of the human body may be determined as the X-axis, and z left-to-right direction of the human torso may be determined as the Y-axis. In some embodiments, the specific coordinate system may be related to the orientation of the user during the calibration process. For example, if the user's body is facing a fixed direction (e.g., north) during the calibration process, the front (north) direction of the body may be the X-axis. In the calibration process, the X axis direction may be fixed.

In step 1320, first coordinate information in at least one original coordinate system when a user is in a first pose may be obtained.

In some embodiments, the step may be performed by the obtaining module 210. The first pose may be a pose that the user approximately remains standing. The obtaining module 210 (e.g., the sensor) may obtain the first coordinate information in the original coordinate system based on the user's first pose.

In step 1330, second coordinate information in the at least one original coordinate system when the user is in a second pose may be obtained.

In some embodiments, the step may be performed by the obtaining module 210. The second pose may be a pose that the user's body part (e.g., the arm) where the sensor is located is tilted forward. In some embodiments, the obtaining module 210 (e.g., the sensor) may obtain the second coordinate information in the original coordinate system based on the user's second pose (e.g., a forward tilting pose).

In step 1340, a relationship between the at least one original coordinate system and the specific coordinate system may be determined based on the first coordinate information, the second coordinate information, and the specific coordinate system.

In some embodiments, the step may be performed by the processing module 220 and/or the processing device 110. In some embodiments, a first rotation matrix may be determined based on the first coordinate information corresponding to the first pose. In the first pose, since the Euler angles in the X direction and the Y direction of the specific coordinate system in a ZYX rotation order are 0, and the Euler angles in the X direction and the Y direction of the original coordinate system are not necessarily 0, then the first rotation matrix is the rotation matrix obtained by rotating the original coordinate system in the reverse direction around the X-axis and then around the Y-axis. In some embodiments, a second rotation matrix may be determined based on the second coordinate information of the second pose (e.g., the body part where the sensor is located is tilted forward). Specifically, in the second pose, it is known that the Euler angles of the specific coordinate system in the Y direction and a $Z_3$ direction are 0 in the ZYZ rotation order, and the Euler angles of the original coordinate system in the Y direction and the $Z_3$ direction are not necessarily 0, then the second rotation matrix is the rotation matrix obtained by rotating the original coordinate system in the reverse direction around the Y direction and then around the $Z_3$ direction. The conversion relationship between the original coordinate system and the specific coordinate system may be determined based on the first rotation matrix and the second rotation matrix. In some embodiments, when there are a plurality of original coordinate systems (sensors), the conversion relationship between each original coordinate system and the specific coordinate system may be determined according to the above method.

It should be noted that the first pose is not limited to an approximately standing pose, and the second pose is not limited to the pose that the user's body part (e.g., the arm) where the sensor is located is tilted forward. The first and second poses herein may be approximated as being stationary during the calibration process. In some embodiments, the first pose and/or the second pose may also be a dynamic pose during the calibration process. For example, the user's walking attitude may be a relatively fixed attitude, an angle and an angular velocity of the arms, the legs and the feet during walking may be extracted to recognize a movement, such as a forward stride, a forward arm swing, or the like. The user's forward walking attitude may be used as the second pose in the calibration process. In some embodiments, the second pose is not limited to one movement, and a plurality of movements may also be extracted as the second pose. For example, coordinate information of a plurality of movements may be fused to obtain a more accurate rotation matrix.

In some embodiments, the rotation matrix may be dynamically corrected during the calibration process using one or more signal processing algorithms (e.g., using a Kalman filtering algorithm) to obtain a better transformation matrix in the whole calibration process.

In some embodiments, a machine learning algorithm, or other algorithms may be used for automatic recognition of specific movements to update the rotation matrix in real time. For example, if the machine learning algorithm recognizes that a current user is walking, or standing, the calibration process may be automatically started. In this case, the wearable device no longer need an explicit calibration process, and the rotation matrix may be dynamically updated when the user uses the wearable device.

In some embodiments, an installation position of the attitude sensor may be relatively fixed and a rotation matrix may be preset, which may make the recognition process of the specific movement more accurate. Further, the rotation matrix may continue to be corrected during the user's use of the wearable device to make the obtained rotation matrix closer to the real situation.

It should be noted that the above description of the process 1300 is for example and illustration purposes only, and does not limit the scope of application of the present disclosure. For those skilled in the art, various amendments and changes can be made to process 1300 under the guidance of the present disclosure. However, these amendments and changes are still within the scope of the present disclosure.

Figure 14:
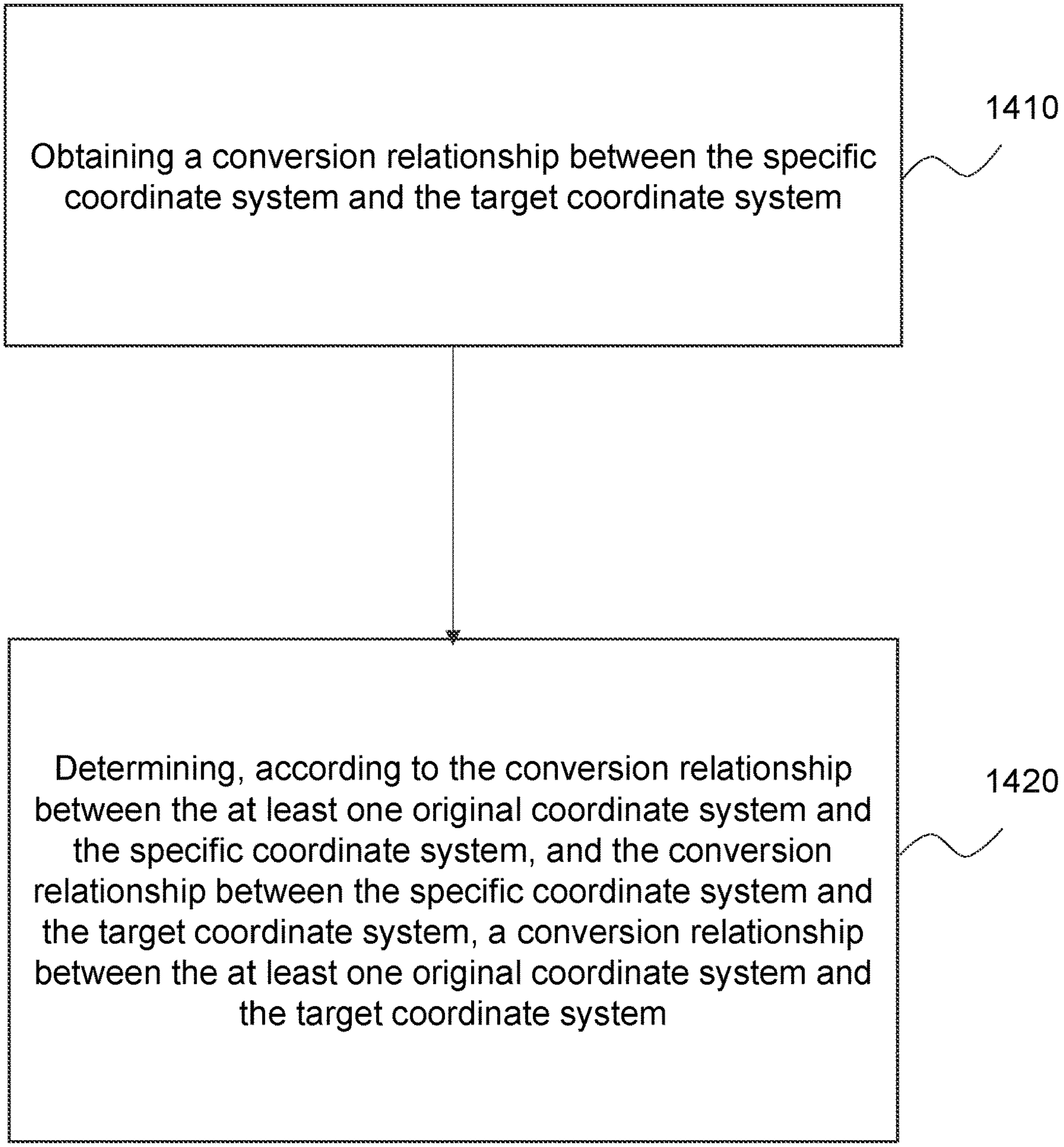
FIG. 14 is a flowchart of an exemplary process for determining a conversion relationship between an original coordinate system and a target coordinate system according to some embodiments of the present disclosure.

FIG. 14 is a flowchart of an exemplary process for determining a conversion relationship between an original coordinate system and a target coordinate system according to some embodiments of the present disclosure. As shown in FIG. 14, the process 1400 may include following steps.

In step 1410, a conversion relationship between a specific coordinate system and a target coordinate system may be obtained.

In some embodiments, the step may be performed by the processing module 220 and/or the processing device 110. In both of the specific coordinate system and the target coordinate system, a length direction of the human torso may be determined as the Z-axis. Therefore, the conversion relationship between the specific coordinate relationship and the target coordinate system may be obtained based on a conversion relationship between the X-axis of the specific coordinate system and the X-axis of the target coordinate system and a conversion relationship between the Y-axis of the specific coordinate system and the Y-axis of the target coordinate system. The principle of obtaining the conversion relationship between the specific coordinate relationship and the target coordinate system may be found in FIG. 13 and its relevant descriptions.

In some embodiments, in the specific coordinate system, the length direction of the human torso may be determined as the Z-axis and a front-to-back direction of the human body may be determined as a calibrated X-axis. Since the front-to-back direction of the user's body changes during motion (e.g., a turning motion) and cannot be fixed in the calibrated coordinate system, it is necessary to determine a coordinate system that can rotate with the body, i.e., the target coordinate system. In some embodiments, the target coordinate system may change with the user's orientation, and the X-axis of the target coordinate system is always in front of the human torso.

In step 1420, a conversion relationship between at least one original coordinate system and the target coordinate system may be determined according to a conversion relationship between the at least one original coordinate system and the specific coordinate system, and the conversion relationship between the specific coordinate system and the target coordinate system.

In some embodiments, the step may be performed by the processing module 220 and/or the processing device 110. In some embodiments, the processing device 110 may determine the conversion relationship between the at least one original coordinate system and the target coordinate system according to the conversion relationship between the at least one original coordinate system and the specific coordinate system determined in the process 1300 and the conversion relationship between the specific coordinate system and the target coordinate system determined in step 1410, such that the coordinate information in the original coordinate system can be converted to the coordinate information in the target coordinate system.

It should be noted that the above description of the process 1400 is for example and illustration purposes only and does not limit the scope of application of the present disclosure. For those skilled in the art, various amendments and changes can be made to the process 1400 under the guidance of the present disclosure. However, these amendments and changes are still within the scope of the present disclosure.

In some embodiments, the position of the attitude sensor set on the wearable device 130 may change and/or the installation angle of the attitude sensor on the human body may be different, then the user performs the same motion, and the attitude data returned by the attitude sensor may have great differences.

Figure 15A:
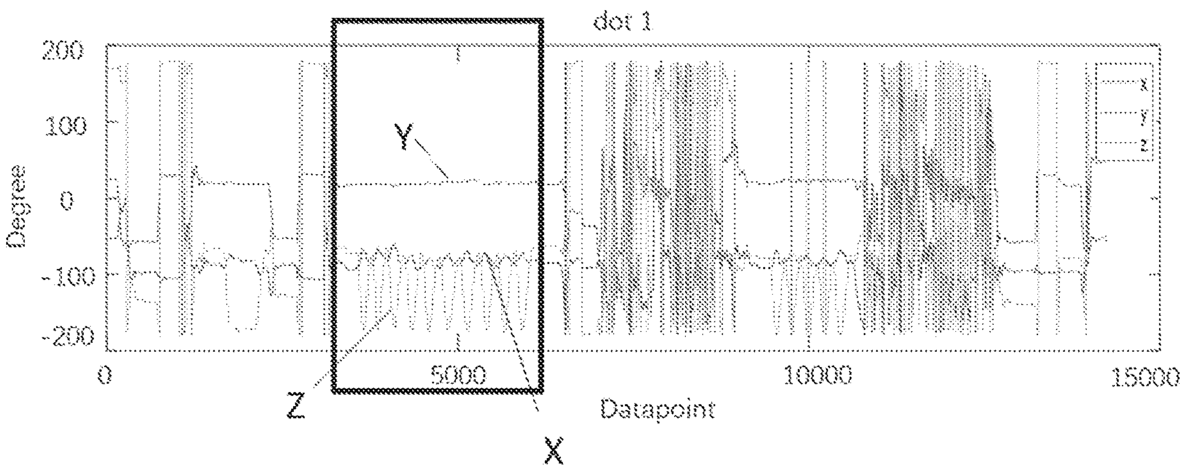
FIG. 15A is an exemplary vector coordinate diagram illustrating Euler angle data in an original coordinate system at a position of a small arm of a human body according to some embodiments of the present disclosure.

FIG. 15A is an exemplary vector coordinate diagram illustrating Euler angle data in an original coordinate system at a position of a small arm of a human body according to some embodiments of the present disclosure. A boxed part may represent the Euler angle data (the coordinate information) in the original coordinate system corresponding to the position of the small arm when the user performs the same movement. As shown in FIG. 15A, the result of the Euler angle vector in the Z-axis direction (shown as "Z" in FIG. 15A) in the boxed part are approximately in a range of −180° to (−80°). The result of the Euler angle vector in the Y-axis direction (shown as "Y" in FIG. 15A) fluctuate approximately around 0°. The result of the Euler angle vector in the X-axis direction (shown as "X" in FIG. 15A) fluctuate approximately around −80°. A fluctuation range here may be 20°.

Figure 15B:
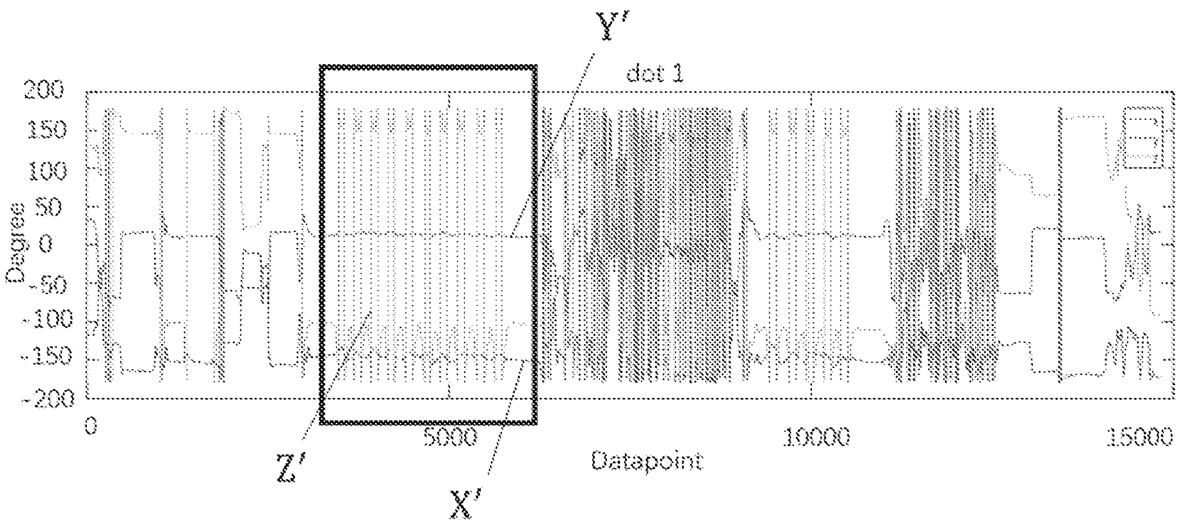
FIG. 15B is an exemplary vector coordinate diagram illustrating Euler angle data in another original coordinate system at a position of a small arm of a human body according to some embodiments of the present disclosure.

FIG. 15B is an exemplary vector coordinate diagram illustrating Euler angle data in another original coordinate system at a position of a small arm of a human body according to some embodiments of the present disclosure. The boxed part may represent the Euler angle data in the original coordinate system corresponding to the other position of the small arm when the user performs the same movement (the same movement as shown in FIG. 15A). As shown in FIG. 15B, the result of the Euler angle vector in the Z-axis direction (shown as "Z" in FIG. 15B) in the boxed part is approximately in a range of −180° to 180°. The result of the Euler angle vector in the Y-axis direction (shown as "Y" in FIG. 15B) fluctuate approximately around 0°. The result of the Euler angle vector in the X-axis direction (shown as "X" in FIG. 15B) fluctuate approximately around −150°. The fluctuation range here may be 20°.

The Euler angle data shown in FIG. 15A and FIG. 15B are the Euler angle data (the coordinate information) respectively obtained in the original coordinate system when the user performs the same movement at different positions of the human small arm (it can also be understood that the installation angle of the attitude sensor at the position of the human small arm is different). Compared with FIG. 15A and FIG. 15B, it can be seen that, the installation angle of the attitude sensor on the human body is different, when the user performs the same movement, the Euler angle data in the original coordinate system returned by the attitude sensor may vary greatly. For example, the result of the Euler angle vector in the Z-axis direction in FIG. 15A is approximately in the range of −180°-(−80°), and the result of the Euler angle vector in the Z-axis direction in FIG. 15B is approximately in the range of −180°-180°, which are quite different from each other.

Figure 16A:
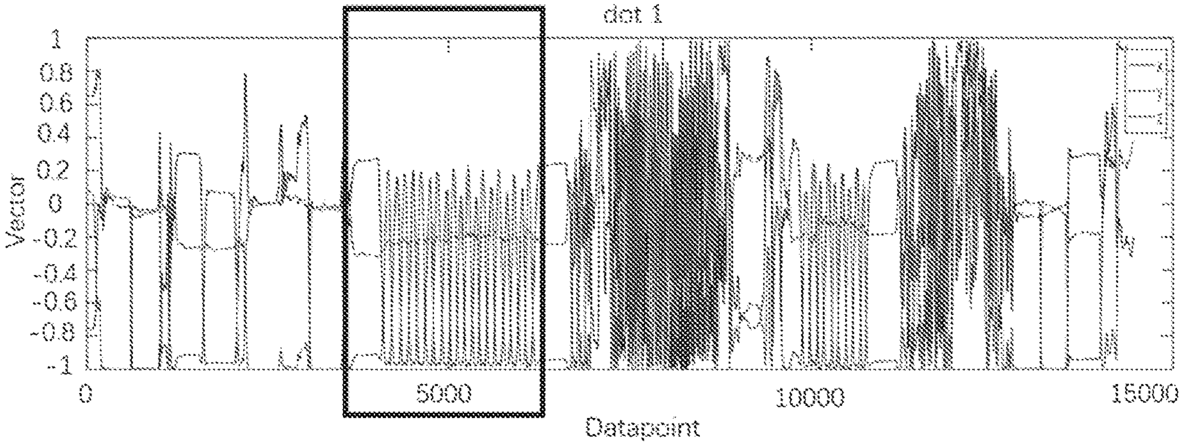
FIG. 16A is an exemplary vector coordinate diagram of Euler angle data in a target coordinate system at a position of a small arm of a human body according to some embodiments of the present disclosure.

In some embodiments, the Euler angle data in the original coordinate system corresponding to sensors with different installation angles may be converted to the Euler angle data in the target coordinate system, thereby facilitating the analysis of the attitude signal of the sensors at different positions. Merely as way of exemplary illustration, a line where the left arm is located may be abstracted as a unit vector pointing from the elbow to the wrist. T unit vector may be a coordinate value in the target coordinate system. In the target coordinate system, an axis pointing to the rear of the body may be determined as the X-axis, an axis pointing to the right side of the body may be determined as the Y-axis, and an axis pointing to the top of the body may be determined as the Z-axis, which conforms to the right-handed coordinate system. For example, a coordinate value [−1, 0, 0] in the target coordinate system indicates that the arm is held forward flat. A coordinate value [0, −1, 0] in the target coordinate system indicates that the arm is held flat to the left. FIG. 16A is an exemplary vector coordinate diagram of Euler angle data in a target coordinate system at a position of a small arm of a human body according to some embodiments of the present disclosure. FIG. 16A is a curve obtained after the Euler angle data of the small arm in the original coordinate in FIG. 15A is converted into vector coordinates in the target coordinate system. The boxed part may represent the Euler angle data in the target coordinate system at the position of the small arm when the user performs the same movement. As shown in FIG. 16A, a small arm vector [x, y, z] in the boxed part moves reciprocally between a first position and a second position, wherein the first position is [0.2, −0.9, −0.38] and the second position is [0.1, −0.95, −0.3]. It should be noted that for each reciprocal movement of the small arm, there may be a small deviation between the first position and the second position.

Figure 16B:
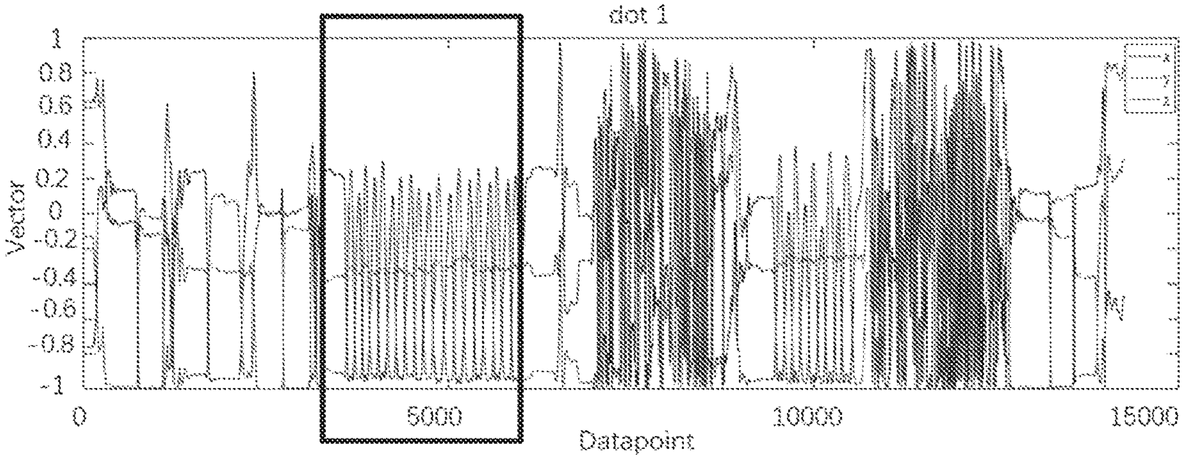
FIG. 16B is an exemplary vector coordinate diagram of Euler angle data in a target coordinate system at another location of a small arm of a human body according to some embodiments of the present disclosure.

FIG. 16B is an exemplary vector coordinate diagram of Euler angle data in a target coordinate system at another location of a small arm of a human body according to some embodiments of the present disclosure. FIG. 16B is a curve obtained after the Euler angle data of the small arm in the original coordinate in FIG. 15B is converted into vector coordinates in the target coordinate system. The boxed part may represent the Euler angle data in the target coordinate system at another location of the small arm when the user performs the same movement (the same movement as the movement shown in FIG. 16A). As shown in FIG. 16B, a small arm vector [x, y, z] reciprocates between the first position and the second position similarly, wherein the first position is [0.2, −0.9, −0.38] and the second position is [0.1, −0.95, −0.3].

Combining FIG. 15A to FIG. 16B, it can be seen from FIGS. 15A and 15B that the Euler angles in the original coordinate system have a great difference in the range of values and the fluctuation form due to the different installation positions of the two attitude sensors. After converting the coordinate information of the original coordinate system corresponding to the two attitude sensors to the vector coordinates corresponding to the target coordinate system (e.g., the vector coordinates in FIGS. 16A and 16B) respectively, two approximately same vector coordinates may be obtained. That is, the method can make the feature information corresponding to the attitude signal not affected by the sensor installation position. Specifically, in FIG. 16A and FIG. 16B, it can be seen that the two attitude sensors are installed at different positions on the small arm, and after the coordinate conversion, the same vector coordinates may be obtained, i.e., it can represent the process of the arm switching back and forth between two states of state 1 (arm held flat to the right) and state 2 (arm held flat to the front) during the process of the seated chest press.

Figure 17:
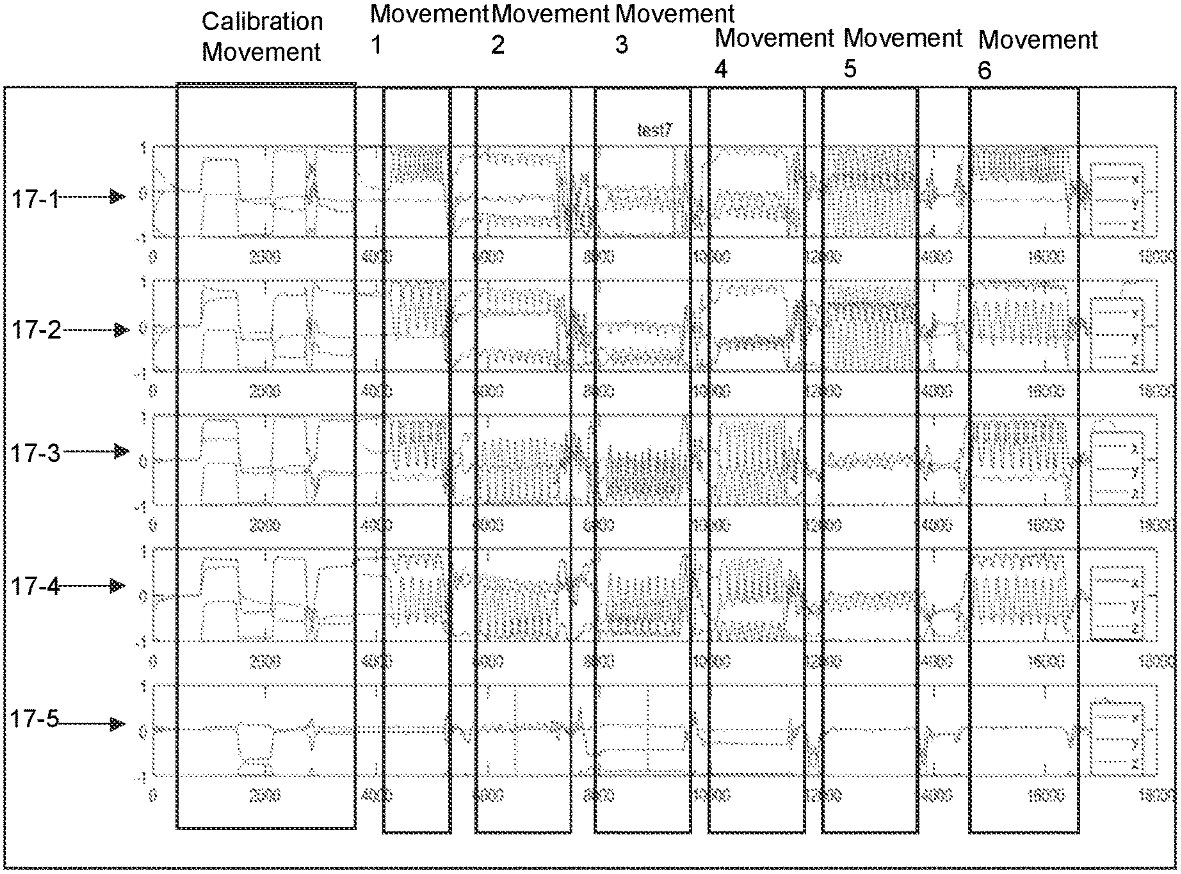
FIG. 17 is an exemplary vector coordinate diagram of Euler angle data in a target coordinate system of a multi-sensor according to some embodiments of the present disclosure.

FIG. 17 is an exemplary vector coordinate diagram of a limb vector in a target coordinate system according to some embodiments of the present disclosure. As shown in FIG. 17, vector coordinates of attitude sensors in a target coordinate system at positions of the left small arm (17-1), the right small arm (17-2), the left large arm (17-3), the right large arm (17-4), and the torso (17-5) of the human body may be represented from top to bottom, respectively. The vector coordinates of each position (e.g., 17-1, 17-2, 17-3, 17-4, 17-5) in the target coordinate system during motion of the human are illustrated in FIG. 17. The first 4200 points in FIG. 17 may be calibration movements required for limb calibration, such as standing, torso forward, arm forward, arm side planks, etc. By using the calibration movements corresponding to the first 4200 points to calibrate, raw data collected by the attitude sensors may be converted to the Euler angles in the target coordinate system. To facilitate the analysis of the data, it may further be converted into the coordinate vector of the arm vector in the target coordinate system. In the target coordinate system, the X-axis may point to the front of the torso, the Y-axis may point to the left of the torso, and the Z-axis may point to the top of the torso. The reciprocal movements in FIG. 17 from left to right are movement 1, movement 2, movement 3, movement 4, movement 5, and movement 6, which are seated chest press, high pull-down, seated chest thrust, seated shoulder thrust, barbell dip head curl, and seated chest press, respectively. As shown in FIG. 17, different movements have different movement patterns, which may be clearly recognized by using the limb vectors. At the same time, the same movement also has good repeatability. For example, the movement 1 and the movement 6 both represent the seated chest press, and the curves of these two movements have good repeatability.

In some embodiments, the attitude data (e.g., the Euler angle, the angular velocity, etc.) directly output by a module of the original coordinate system may be converted to the attitude data in the target coordinate system according to process 1300 and process 1400, so that highly consistent attitude data (e.g., the Euler angle, the angular velocity, the limb vector coordinate, etc.) may be obtained.

Figure 18A:
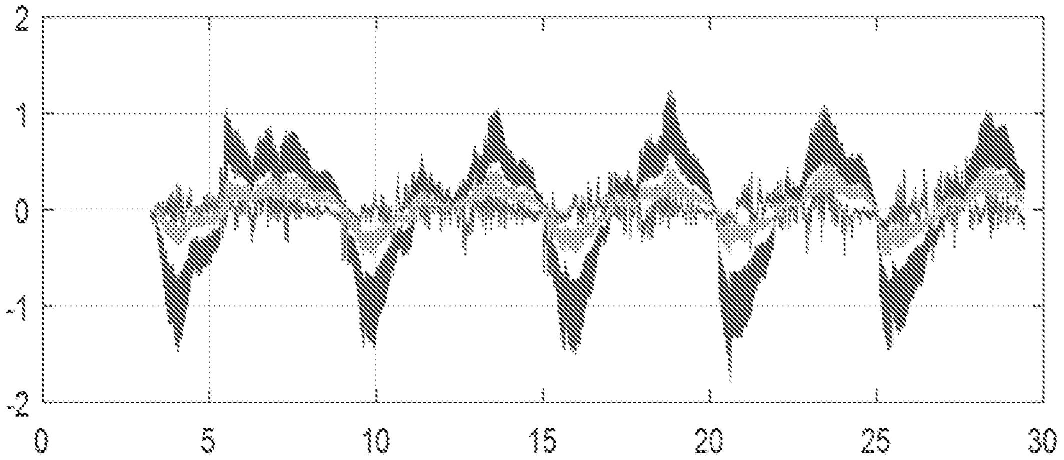
FIG. 18A is a diagram illustrating exemplary results of an original angular velocity according to some embodiments of the present disclosure.
Figure 18B:
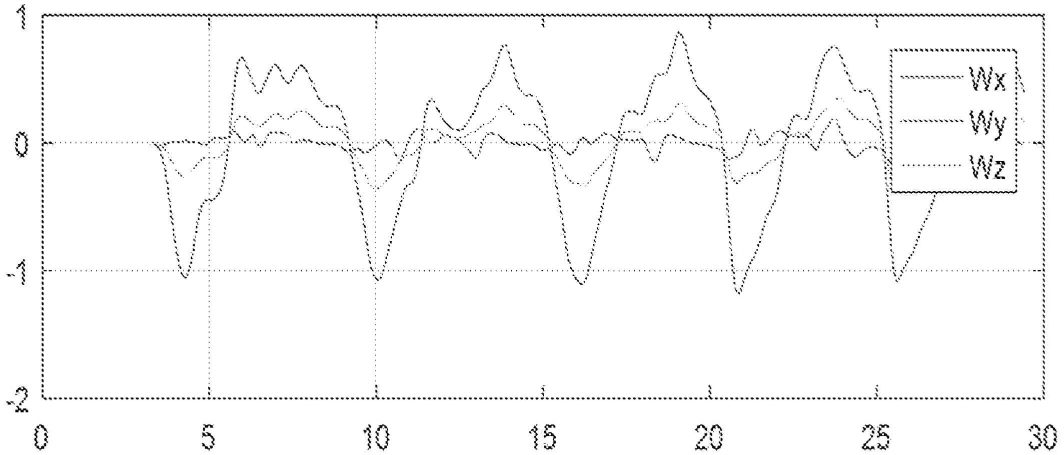
FIG. 18B is a diagram illustrating exemplary results of an angular velocity after filtering processing according to some embodiments of the present disclosure.

FIG. 18A is a diagram illustrating an exemplary coordinate vector of an original angular velocity according to some embodiments of the present disclosure. The original angular velocity may be understood as the conversion of the Euler angle data in the original coordinate systems corresponding to the sensors with different installation angles to the Euler angle data in the target coordinate system. In some embodiments, factors such as jitter during the motion of the user may affect the result of the angular velocity in the attitude data. As shown in FIG. 18A, the original angular velocity shows a more obvious unsmooth curve in its vector coordinate curve under an influence of jitter, etc. For example, a presence of an abrupt signal in the vector coordinate curve of the original angular velocity makes the vector coordinate curve of the original angular velocity unsmooth. In some embodiments, due to the impact of jitter, etc., on the angular velocity result, it is necessary to correct the jittered angular velocity to obtain a smooth vector coordinate curve. In some embodiments, the original angular velocity may be filtered using a 1 Hz-3 Hz low-pass filtering method. FIG. 18B is a diagram illustrating exemplary results of an angular velocity after filtering processing according to some embodiments of the present disclosure. As shown in FIG. 18B, after performing the 1 Hz-3 Hz low-pass filtering on the original angular velocity, the effect of jitter and other effects on the angular velocity (e.g., abrupt signals) may be eliminated, so that the vector coordinate curve corresponding to the angular velocity may be displayed smoother. In some embodiments, performing the low-pass filtering from 1 Hz to 3 Hz on the angular velocity may effectively prevent the effect of jitter, etc., on the attitude data (e.g., the Euler angle, the angular velocity, etc.), so as to facilitate the subsequent signal segmentation process. In some embodiments, the filtering process may also filter out an industrial frequency signal and its harmonic wave signal, burr signal, etc., from the movement signal. It should be noted that low-pass filtering at 1 Hz-3 Hz introduces time delay, which makes a movement point of the attitude signal and a movement point of a real electromyographic signal misaligned in time. Therefore, the time delay generated during the low-pass filtering process may be subtracted from the vector coordinate curve after the low-pass filtering processing, to ensure the synchronization of the attitude signal and the electromyographic signal in time. In some embodiments, the time delay may be associated with a center frequency of the filter. When the attitude signal and the electromyographic signal are processed with different filters, the time delay may be adjusted adaptively according to the center frequency of the filter. In some embodiments, since the angular range of the Euler angle is [480°, +180°], an obtained Euler angle may have a change of −180° to +180° or +180° to −180° when an actual Euler angle is not in this angular range. For example, when the angle is −181°, the Euler angle changes to 179°. In the practical application, the angle change may affect the determination of the angle difference, and it is necessary to correct the angle change first.

In some embodiments, a movement recognition model may also be used to analyze the user's movement signal or the feature information corresponding to the movement signal, so as to recognize the user's movement. In some embodiments, the movement recognition model may include a trained machine learning model configured to recognize the user's movement. In some embodiments, the movement recognition model may include one or more machine learning models. In some embodiments, the movement recognition model may include, but is not limited to, one or more of a machine learning model that classifies the user's movement signal, a machine learning model that recognizes the movement quality of the user, a machine learning model that recognizes the number of movements of the user, and a machine learning model that recognizes a fatigue index of the user performing the movement. In some embodiments, the machine learning model may include one or more of a linear classification model (LR), a support vector machine model (SVM), a plain Bayesian model (NB), a K-nearest neighbor model (KNN), a decision tree model (DT), a random forest/a gradient boosting decision tree (RF/GDBT, etc.), etc. More descriptions regarding the movement recognition model may be found elsewhere in the present disclosure, such as FIG. 20 and its relevant descriptions.

Figure 19:
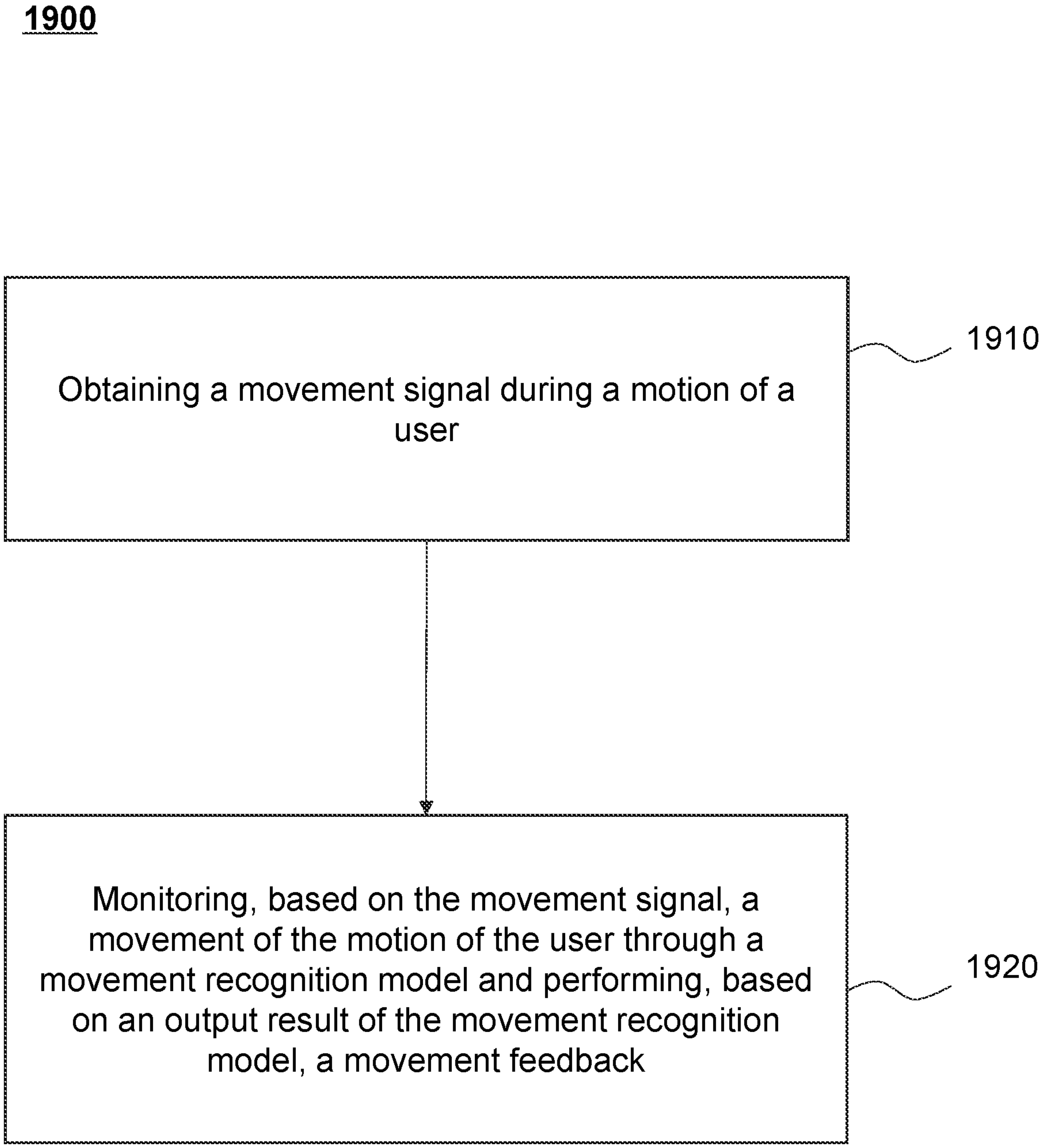
FIG. 19 is a flowchart illustrating an exemplary motion monitoring and feedback method according to some embodiments of the present disclosure.

FIG. 19 is a flowchart illustrating an exemplary motion monitoring and feedback method according to some embodiments of the present disclosure. As shown in FIG. 19, the process 1900 may include the following steps.

In step 1910, a movement signal during a motion of a user may be obtained.

In some embodiments, the step may be performed by the obtaining module 210. In some embodiments, the movement signal may at least include feature information corresponding to an electromyographic signal and feature information corresponding to an attitude signal. The movement signal may refer to human body parameter information during the motion of the user. In some embodiments, the human body parameter information may include, but is not limited to, the electromyographic signal, the attitude signal, a heart rate signal, a temperature signal, a humidity signal, a blood oxygen concentration, or the like, or any combination thereof. In some embodiments, the movement signal may at least include the electromyographic signal and the attitude signal. In some embodiments, an electromyographic sensor in the obtaining module 210 may collect the electromyographic signal during the motion of the user, and an attitude sensor in the obtaining module 210 may collect the attitude signal during the motion of the user.

In step 1920, a movement of the motion of the user may be monitored based on the movement signal through a movement recognition model and a movement feedback may be performed based on an output result of the movement recognition model.

In some embodiments, the step may be performed by the processing module 220 and/or the processing device 110. In some embodiments, the output result of the movement recognition model may include, but is not limited to, a movement type, a movement quality, a movement quantity, a fatigue index, or the like, or any combination thereof. For example, the movement recognition model may recognize the movement type of the user as the seated chest press based on the movement signal. As another example, one machine learning model of the movement recognition model may first recognize the movement type of the user as the seated chest press based on the movement signal, and another machine learning model of the movement recognition model may output the movement quality of the user as a standard movement or an incorrect movement according to the movement signal (e.g., amplitude information, the frequency information of the electromyographic signal, and/or an angular velocity, an angular velocity direction, and an acceleration value of angular velocity of the attitude signal). In some embodiments, the movement feedback may include sending prompt information. In some embodiments, the prompt information may include, but is not limited to, a voice prompt, a text prompt, an image prompt, a video prompt, etc. For example, if the output result of the movement recognition model is the incorrect movement, the processing device 110 may control the wearable device 130 or the mobile terminal device 140 to send the voice prompt (e.g., information such as "nonstandard movement") to the user to remind the user to adjust a fitness movement in time. As another example, if the output result of the movement recognition model is the standard movement, the wearable device 130 or the mobile terminal device 140 may not send the prompt information, or send prompt information such as "standard movement". In some embodiments, the motion feedback may also include the wearable device 130 stimulating a corresponding part of the motion of the user. For example, a component of the wearable device 130 may stimulate the corresponding part of the motion of the user through a manner such as a vibration feedback, an electrical stimulation feedback, a pressure feedback, etc. For example, if the output result of the movement recognition model is the incorrect movement, the processing device 110 may control the component of the wearable device 130 to stimulate the corresponding part of the motion of the user. In some embodiments, the movement feedback may also include outputting a motion record during the motion of the user. The motion record here may refer to the movement type, a movement time, the movement quantity, the movement quality, the fatigue index, physiological parameter information during the motion of the user, or the like, or any combination thereof. Further description regarding the movement recognition model may be found elsewhere in the present disclosure and will not be repeated herein.

It should be noted that the above description regarding the process 1900 is merely provided for the purpose of illustration, and not intended to limit the scope of the present disclosure. For those skilled in the art, various amendments and changes can be made to the process 1900 under the guidance of the present disclosure. However, these amendments and changes are still within the scope of the present disclosure.

Figure 20:
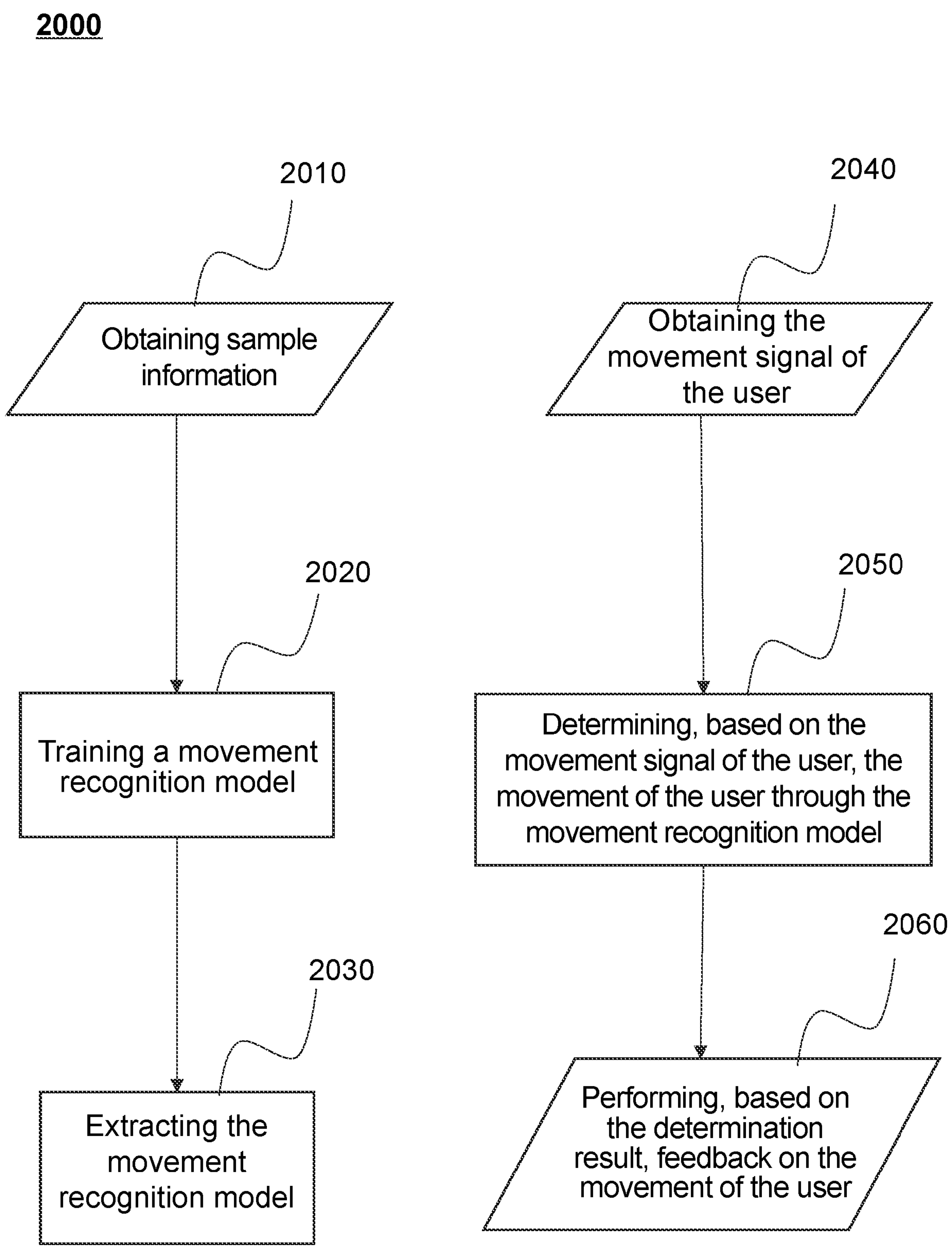
FIG. 20 is a flowchart illustrating exemplary process for model training according to some embodiments of the present disclosure

FIG. 20 is a flowchart illustrating an exemplary process for model training according to some embodiments of the present disclosure.

In step 2010, sample information may be obtained.

In some embodiments, the step may be performed by the obtaining module 210. In some embodiments, the sample information may include a movement signal during a motion of a professional (e.g., a fitness instructor) and/or a non-professional. For example, the sample information may include an electromyographic signal and/or an attitude signal generated by the professional and/or the non-professional while performing a same type of movement (e.g., the seated chest press). In some embodiments, the electromyographic signal and/or the attitude signal in the sample information may be subjected to a segmentation processing of the process 700, a burr processing of the process 900, and a conversion processing of the process 1300, etc., to form at least one segment of the electromyographic signal and/or the attitude signal. The at least one segment of the electromyographic signal and/or the attitude signal may be used as an input of a machine learning model to train the machine learning model. In some embodiments, feature information corresponding to the at least one segment of the electromyographic signal and/or feature information corresponding to the attitude signal may also be used as the input of the machine learning model to train the machine learning model. For example, frequency information and amplitude information of the electromyographic signal may be used as the input of the machine learning model. As another example, an angular velocity, an angular velocity direction, and an acceleration value of angular velocity of the attitude signal may be used as the input of the machine learning model. As another example, a movement start point, a movement middle point, and a movement end point of the movement signal may be used as the input of the machine learning model. In some embodiments, the sample information may be obtained from a storage device of the processing device 110. In some embodiments, the sample information may be obtained from the obtaining module 210.

In step 2020, a movement recognition model may be trained.

The step may be performed by the processing device 110. In some embodiments, the movement recognition model may include one or more machine learning models. For example, the movement recognition model may include, but is not limited to, a machine learning model that classifies the movement signal of the user, a machine learning model that recognizes a movement quality of the user, a machine learning model that recognizes a movement quantity of the user, a machine learning model that recognizes a fatigue degree of the user performing the movement, or any combination thereof. In some embodiments, the machine learning model may include a linear classification model (LR), a support vector machine model (SVM), a Naive Bayesian model (NB), a K-nearest neighbor model (KNN), a decision tree model (DT), a random forest/a gradient boosting decision tree (RF/GDBT, etc.), etc.

In some embodiments, training of the machine learning model may include obtaining the sample information. In some embodiments, the sample information may include the movement signal during the motion of the professional (e.g., the fitness instructor) and/or the non-professional. For example, the sample information may include the electromyographic signal and/or the attitude signal generated by professional and/or the non-professional while performing the same type of movement (e.g., the seated chest press). In some embodiments, the electromyographic signal and/or the attitude signal in the sample information may be subjected to the segmentation processing of the process 700, the burr processing of the process 900, and the conversion processing of the process 1300, etc., to form at least one segment of the electromyographic signal and/or the attitude signal. The at least one segment of the electromyographic signal and/or the attitude signal may be used as the input to the machine learning model to train the machine learning model. In some embodiments, the feature information corresponding to the at least one segment of the electromyographic signal and/or the feature information corresponding to the attitude signal may also be used as the input of the machine learning model to train the machine learning model. For example, the frequency information and the amplitude information of the electromyographic signal may be used as the input of the machine learning model. As another example, the angular velocity, the angular velocity direction, and the acceleration value of angular velocity of the attitude signal may be used as the input of the machine learning model. As another example, the movement start point, the movement middle point, and/or the movement end point signal (including the electromyographic signal and/or the attitude signal) corresponding to the signal may be used as the input of the machine learning model.

In some embodiments, when a machine learning model that recognizes a movement type of the user is trained, the sample information from different movement types (each segment of the electromyographic signal or/and the attitude signal) may be labelled. For example, the sample information from the electromyographic signal and/or the attitude signal generated when the user performs the seated chest press may be labelled "1", where "1" is configured to represent the "seated chest press." The sample information from the electromyographic signal and/or the attitude signal generated when the user performs a bicep curl may be marked as "2," where "2" is configured to represent the "bicep curl." The feature information (e.g., the frequency information, the amplitude information) of the electromyographic signals and the feature information (e.g., the angular velocity, the angular velocity direction, the acceleration value of angular velocity) of the attitude signals corresponding to the different movement types may be different. The labelled sample information (e.g., the feature information corresponding to the electromyographic signal and/or the attitude signal in the sample information) may be used as the input of the machine learning model to train the machine learning model, so that the movement recognition model configured to recognize the movement type may be obtained, and by inputting the movement signal in the machine learning model, a movement type corresponding to the movement signal may be output.

In some embodiments, the movement recognition model may further include the machine learning model for determining the movement quality of the user. The sample information here may include both a standard movement signal (also known as a positive sample) and a non-standard movement signal (also known as a negative sample). The standard movement signal may include a movement signal generated when the professional performs a standard movement. For example, a movement signal generated when the professional performs the seated chest press standardly may be the standard movement signal. The non-standard movement signal may include a movement signal generated when the user performs a non-standard movement (e.g., an incorrect movement). In some embodiments, the electromyographic signal and/or the attitude signal in the sample information may be subjected to the segmentation processing of the process 700, the burr processing of the process 900, and the conversion processing of the process 1300, etc., to form at least one segment of the electromyographic signal and/or the attitude signal. The at least one segment of the electromyographic signal and/or the attitude signal may be used as the input of the machine learning model to train the machine learning model. In some embodiments, the positive sample and the negative sample of the sample information (each segment of the electromyographic signal or/the attitude signal) may be labelled. For example, the positive sample may be labelled "1" and the negative sample may be labelled "0." The "1" here may be configured to characterize a movement of the user as a standard movement, and the "0" here may be configured to characterize a movement of the user as an incorrect movement. A trained machine learning model may output different labels based on the input sample information (e.g., the positive sample, the negative sample). It should be noted that the movement recognition model may include one or more machine learning models for analyzing and recognizing the movement quality of the user. Different machine learning models may analyze and recognize the sample information from the different movement types, respectively.

In some embodiments, the movement recognition model may also include a model that recognizes the movement quantity of fitness movements of the user. For example, at least one set of the movement start point, the movement middle point, and the movement end point may be obtained by performing segmentation processing of the process 700 on the movement signal (e.g., the electromyographic signal and/or the attitude signal) in the sample information, each set of the movement start point, the movement middle point, and the movement end point may be labelled, respectively (e.g., the movement start point may be labeled 1, the movement middle point may be labeled 2, and the movement end point may be labeled 3), and the labels may be used as the input of the machine learning model. For example, if a set of consecutive "1," "2," and "3" is input into the machine learning model, one movement may be output. For example, if three consecutive sets of "1," "2," and "3" are input into the machine learning model, three movements may be output.

In some embodiments, the movement recognition model may also include the machine learning model for recognizing a fatigue index of the user. The sample information here may also include a physiological parameter signal such as an electro-cardio signal, a respiratory rate, a temperature signal, a humidity signal, etc. For example, different frequency ranges of the electro-cardio signal may be used as input data of the machine learning model. The frequency range of the electro-cardio signal from 60 beats/min to 100 beats/min may be labelled "1" (normal). The frequency range of the electro-cardio signal less than 60 beats/min or more than 100 beats/min may be labelled "2" (abnormal). In some embodiments, a further segmentation may be performed and different indices may be labeled as the input data based on the frequency of the electro-cardio signal of the user, and the trained machine learning model may output a corresponding fatigue index according to the frequency of the electro-cardio signal. In some embodiments, the machine learning model may also be trained in combination with the physiological parameter signal such as the respiratory rate, the temperature signal, etc. In some embodiments, the sample information may be obtained from the storage device of the processing device 110. In some embodiments, the sample information may be obtained from the obtaining module 210. It should be noted that the movement recognition model may be any one of the machine learning models or a combination of the plurality of machine learning models, or include other machine learning models, which may be selected according to an actual situation. In addition, the input of the training of the machine learning model is not limited to one segment (one cycle) of the movement signal, but may also be part of a segment of the movement signal, or a plurality of segments of the movement signal, etc.

In step 2030, the movement recognition model may be extracted.

In some embodiments, the step may be performed by the processing device 110. In some embodiments, the processing device 110 and/or the processing module 220 may extract the movement recognition model. In some embodiments, the movement recognition model may be stored to the processing device 110, the processing module 220, or a mobile terminal.

In step 2040, the movement signal of the user may be obtained.

In some embodiments, the step may be performed by the obtaining module 210. For example, in some embodiments, an electromyographic sensor in the obtaining module 210 may obtain the electromyographic signal of the user, and an attitude sensor in the obtaining module 210 may obtain the attitude signal of the user. In some embodiments, the user movement signal may also include other physiological parameter signals such as the electro-cardio signal, the respiration signal, the temperature signal, the humidity signal, etc. during the motion of the user. In some embodiments, the obtained movement signal (e.g., the electromyographic signal and/or the attitude signal) may be subjected to the segmentation processing of the process 700, the burr processing of process the 900, and the conversion processing of the process 1300, etc., to form at least one segment of the electromyographic signal and/or the attitude signal.

In step 2050, the movement of the user may be determined based on the movement signal of the user through the movement recognition model.

The step may be performed by the processing device 110 and/or the processing module 220. In some embodiments, the processing device 110 and/or the processing module 220 may determine the movement of the user based on the movement recognition model. In some embodiments, the trained movement recognition model may include one or more machine learning models. In some embodiments, the movement recognition model may include, but is not limited to, the machine learning model that classifies the movement signal of the user, the machine learning model that recognizes the movement quality of the user, the machine learning model that recognizes the movement quantity of user, the machine learning model that recognizes the fatigue index of the user performing the movement, or any combination thereof. The different machine learning models may have different recognition effects. For example, the machine learning model that classifies the movement signal may use the movement signal of the user as input data and output a corresponding movement type. As another example, the machine learning model that recognizes the movement quality of the user may use the movement signal of the user as input data and output the movement quality (e.g., a standard movement, an incorrect movement). As yet another example, the machine learning model that recognizes the fatigue index of the user performing the movement may use the movement signal (e.g., the frequency of the electrocardio signal) of the user as input data and output the fatigue index of the user. In some embodiments, the movement signal of the user and the determination result (output) of the machine learning model may also be used as the sample information of training the movement recognition model, and the movement recognition model may be trained to optimize relevant parameters of the movement recognition model. It should be noted that the movement recognition model is not limited to the trained machine learning model described above, but can also be a preset model, for example, a manually preset conditional judgment algorithm or manually adding parameters (e.g., a confidence level) to the trained machine learning model, etc.

In step 2060, feedback may be performed on the movement of the user based on the determination result.

In some embodiments, the step may be performed by the wearable device 130 and/or the mobile terminal device 140. Further, the processing device 110 and/or the processing module 220 may send a feedback instruction to the wearable device 130 and/or the mobile terminal device 140 based on the determination result of the movement of the user. The wearable device 130 and/or the mobile terminal device 140 may perform feedback to the user based on the feedback instruction. In some embodiments, the feedback may include sending prompt information (e.g., text information, image information, video information, voice information, indicator information, etc.) and/or stimulating the body of the user by performing a corresponding movement (a manner such as a current stimulation, a vibration, a pressure change, a heat change, etc.). For example, when a user performs a sit-up movement, it may be determined that the user is exerting too much force on a trapezius muscle during the motion (i.e., head and neck movements of the user are not standard) by monitoring the movement signal of the user. In this case, the input/output module 260 (e.g., a vibration prompter) in the wearable device 130 and the mobile terminal device 140 (e.g., a smartwatch, a smartphone etc.) may perform a corresponding feedback movement (e.g., applying the vibration to the user's body part, sending the voice prompt, etc.) to prompt the user to adjust an exertion part in time. In some embodiments, during the motion of the user, the movement type, the movement quality, and the movement quantity during the motion of the user may be determined by monitoring the movement signal during the motion of the user, and the mobile terminal device 140 may output corresponding movement records, so that the user can understand his/her motion situation during the motion.

In some embodiments, when the feedback is performed to the user, the feedback may be matched to perception of the user. For example, when the movement of the user is not standard, the vibration stimulation may be performed on an area corresponding to the movement of the user, and the user may know that the movement is not standard based on the vibration stimulation. The vibration stimulation is within an acceptable range of the user. Further, a matching model may be constructed based on the movement signal of the user and the perception of the user to find a best balance between the user perception and a real feedback.

In some embodiments, the movement recognition model may further be trained based on the movement signal of the user. In some embodiments, training the movement recognition model according to the movement signal of the user may include determining a confidence level of the movement signal of the user by evaluating the movement signal of the user. The confidence level may indicate a quality of the movement signal of the user. For example, the higher the confidence level, the better the quality of the movement signal of the user. In some embodiments, evaluating the movement signal of the user may be performed at a stage such as movement signal obtaining, pre-processing, segmentation, and/or recognition.

In some embodiments, training the movement recognition model according to the movement signal of the user may further include determining whether the confidence level is greater than a confidence level threshold (e.g., 80). If the confidence level is greater than or equal to the confidence level threshold, the movement recognition model may be trained by using the movement signal of the user corresponding to the confidence level as sample data. If the confidence level is smaller than the confidence level threshold, the movement signal of the user corresponding to the confidence level may not be used as sample data to train the movement recognition model. In some embodiments, the confidence level may include, but is not limited to, a confidence level of any stage of the movement signal obtaining, the movement signal pre-processing, the movement signal segmentation, or the movement signal recognition. For example, the confidence level of the movement signal collected by the obtaining module 210 may be used as a determination criterion. In some embodiments, the confidence level may further include a joint confidence level of several stages such as the movement signal obtaining, the movement signal pre-processing, the movement signal segmentation, or the movement signal recognition. The joint confidence level may be obtained by averaging or weighting the confidence level of each stage, etc. In some embodiments, the movement recognition model may be trained in real time, periodically (e.g., a day, a week, a month, etc.), or when a certain data volume is met according to the movement signal of the user.

It should be noted that the above description regarding the process 2000 is merely provided for the purpose of illustration, and not intended to limit the scope of the present disclosure. For those skilled in the art, various amendments and changes can be made to the process 2000 under the guidance of the present disclosure. However, these amendments and changes are still within the scope of the present disclosure.

In some embodiments, when the movement of the user is not standard, the processing device 110 and/or the processing module 220 may send the feedback instruction to the wearable device 130 and/or the mobile terminal 140 based on the determination result of the movement of the user. The wearable device 130 and/or the mobile terminal 140 may perform feedback to the user based on the feedback instruction. For example, the input/output module 260 (e.g., a vibration prompter) in the wearable device 130 and the mobile terminal device 140 (e.g., a smartwatch, a smart phone, etc.) may perform the corresponding feedback movement (e.g., applying the vibration to the user's body part, sending the voice prompt, etc.) to prompt the user that the movement is non-standard or incorrect. In this case, although the user receives the information prompt that there is a non-standard movement during the motion, the user may be unable to identify a reason for the non-standard movement according to the feedback movement, such as a non-standard posture, an incorrect exertion position of a muscle, an incorrect exertion strength of a muscle, etc. On the other hand, if the user feels good about himself/herself after receiving the feedback movement that the motion movement is not standard from the motion monitoring system 100, the user's credibility of the motion monitoring system 100 may also decrease. For example, when a user performs the bicep curl, a standard posture of the movement may be that shoulders needs to be relaxed. The user may subjectively believe that he has relaxed, but in fact, the shoulders may exert force involuntarily, resulting in excessive force on the trapezius muscle. At this time, the user's subjective perception may be inconsistent with an analysis result of the wearable device 130 and/or the mobile terminal device 140, and the user may think that the feedback result of the wearable device 130 and/or the mobile terminal device 140 is inaccurate. Therefore, the embodiments of the present disclosure may also provide a method for displaying a motion monitoring interface. The method may display information related to the motion of the user (e.g., the exertion position of the muscle, the exertion strength of the muscle, and the user's movement model) by using a display device. The user can intuitively observe a problem in the motion according to display content, and timely adjust the movement for a scientific motion.

Figure 21A:
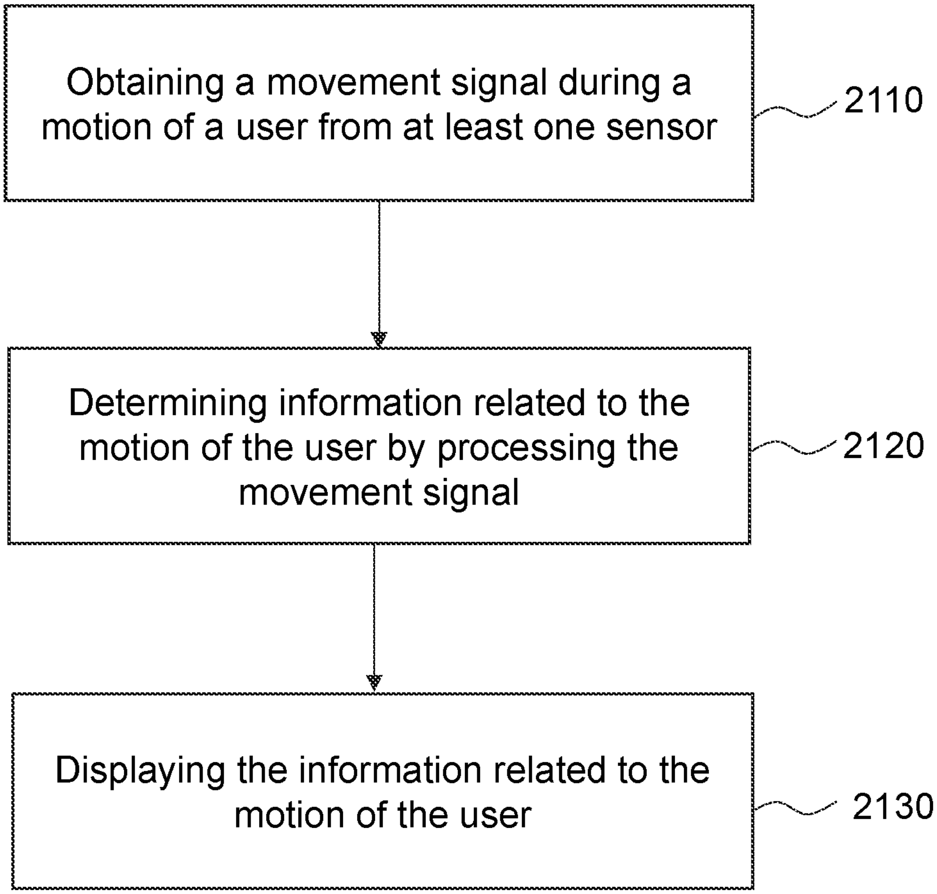
FIG. 21A is an exemplary flowchart of a process for displaying a motion monitoring interface according to some embodiments of the present disclosure.

FIG. 21A is a flowchart illustrating an exemplary process of a method for displaying a motion monitoring interface according to some embodiments of the present disclosure. As shown in FIG. 21A, the process 2100 may include the following steps.

In step 2110, a movement signal during a motion of a user may be obtained from at least one sensor.

In some embodiments, the step 2110 may be performed by the obtaining module 210. In some embodiments, the movement signal during the motion of the user may refer to human body parameter information during the motion of the user. In some embodiments, the human body parameter information may include, but is not limited to, an electromyographic signal, an attitude signal, an electro-cardio signal, a temperature signal, a humidity signal, a blood oxygen concentration, a respiratory rate, or the like, or any combination thereof. In some embodiments, a sensor in the obtaining module 210 may obtain the movement signal during the motion of the user. In some embodiments, an electromyography sensor in the obtaining module 210 may collect the electromyographic signal during the motion of the user. For example, when the user performs the seated chest press, the electromyography sensor in the wearable device corresponding to a position of a human pectoral muscle, a latissimus dorsi, etc. may collect the electromyographic signal corresponding to the muscle position of the user. In some embodiments, an attitude sensor in the obtaining module 210 may collect the attitude signal during the motion of the user. For example, when the user performs a barbell press motion, the attitude sensor in the wearable device corresponding to a position of a human triceps brachii muscle may collect the attitude signal of the position of the user's triceps brachii muscle. In some embodiments, the at least one sensor may include, but is not limited to, an attitude sensor, an electro-cardio sensor, an electromyography sensor, a temperature sensor, a humidity sensor, an inertial sensor, an acid-base sensor, an acoustic transducer, or the like, or any combination thereof. Different types of sensors may be placed at different positions of the user's body according to different signals to be measured, so that different types of sensors and/or sensors at different positions can collect different movement signals.

In some embodiments, the movement signal may be a movement signal formed after the movement signal collected by a plurality of sensors in the obtaining module 210 during the motion of the user is subject to a signal processing process such as filtering, rectification, and/or wavelet transform, a segmentation processing of the process 700, a burr processing of the process 900, or permutation and combination of any one or more of the above processing processes. As described above, the signal processing process such as filtering, rectification, and/or wavelet transform, the segmentation processing of process 700, and the burr processing of process 900 may be performed by the processing module 220 and/or the processing device 110. The obtaining module 210 may obtain the processed movement signal from the processing module 220 and/or the processing device 110.

In step 2120, information related to the motion of the user may be determined by processing the movement signal.

In some embodiments, the step 2120 may be performed by the processing module 220. In some embodiments, the information related to the motion of the user may include a movement type, a movement frequency, a movement intensity, a movement model of the user, or the like, or any combination thereof. In some embodiments, the processing module 220 may determine feature information of the movement signal (e.g., amplitude information, frequency information of the electromyographic signal, and/or an angular velocity, an angular velocity direction, and an acceleration value of angular velocity of the attitude signal) by analyzing and processing the movement signal of the user, and determine the information related to the motion of the user according to the feature information of the movement signal.

In some embodiments, the information related to the motion of the user may include an exertion strength of at least one muscle during the motion of the user. In some embodiments, the processing module 220 may determine the exertion strength of the at least one muscle of the user according to the electromyographic signal collected by the electromyography sensor. For example, when a user performs a deep squat movement, the electromyography sensor set at a position of a human gluteus maximus, a quadriceps femoris muscle, etc. may collect the electromyographic signal corresponding to the muscle position of the user, and the processing module 220 may determine the exertion strength of the gluteus maximus and quadriceps femoris muscle of the user based on a signal strength of the obtained electromyographic signal.

In some embodiments, the processing module 220 may determine the movement type of the user based on the movement signal. For example, the processing module 220 may determine the movement type based on the movement signal and a movement recognition model (e. g., the movement recognition model described in FIG. 20) of the user. For example, the movement type may be manually input. Further, the processing module 220 may determine a muscle located at an exercise position (also called a muscle of the exercise position) of the user and a muscle located at a non-exercise position (also called a muscle of the non-exercise position) of the user according to the movement type of the user. The muscle of the non-exercise position may be a muscle of a position where an incorrect exertion easily occurs or a muscle at a part that is easy to be injured when the user perform a certain movement. Different movement types may correspond to different muscles of exercise positions and different muscles of non-exercise positions. In some embodiments, the user may preset the muscle of the exercise position and the muscle of the non-exercise position corresponding to each movement type. In some embodiments, the processing module 220 may determine whether an exertion part of the user is correct and whether the movement posture is standard when a corresponding movement is performed according to the exertion strengths of the muscle of the exercise position and/or the muscle of the non-exercise position of the user. For example, if the exertion strength of the muscle of the exercise position is too small (e g, smaller than a certain threshold) and/or the exertion strength of the muscle of the non-exercise position is too large (e.g., greater than a certain threshold), it may be considered that the exertion part during the motion of the user is incorrect. In this case, the input/output module 260 may send a feedback signal to the user to prompt the user to adjust the movement in time.

In some embodiments, the information related to the motion of the user may include a user movement model representing a movement of the motion of the user. For example, when the user performs a dumbbell flying bird movement, the attitude sensor set at a position such as a human deltoid muscle, an upper limb joint (e.g., an arm elbow joint), etc. may collect the attitude signal of the deltoid muscle and the upper limb joint of the user. The processing module 220 may process each attitude signal to obtain the feature information corresponding to each attitude signal (e.g., angular velocity information, acceleration information, stress information, displacement information), and the processing module 220 may generate the movement model of the dumbbell flying bird movement according to the feature information. Further description regarding generating the user movement model during the motion of the user based on the attitude signal may be found in FIG. 22 and related description thereof.

In step 2130, the information related to the motion of the user may be displayed.

In some embodiments, the step 2130 may be performed by the input/output module 260. In some embodiments, the information related to the motion of the user may be displayed on a display device (e.g., a display screen) of the wearable device 130 or the mobile terminal device 140, so that the user can intuitively observe a motion situation during the motion.

Figure 21B:
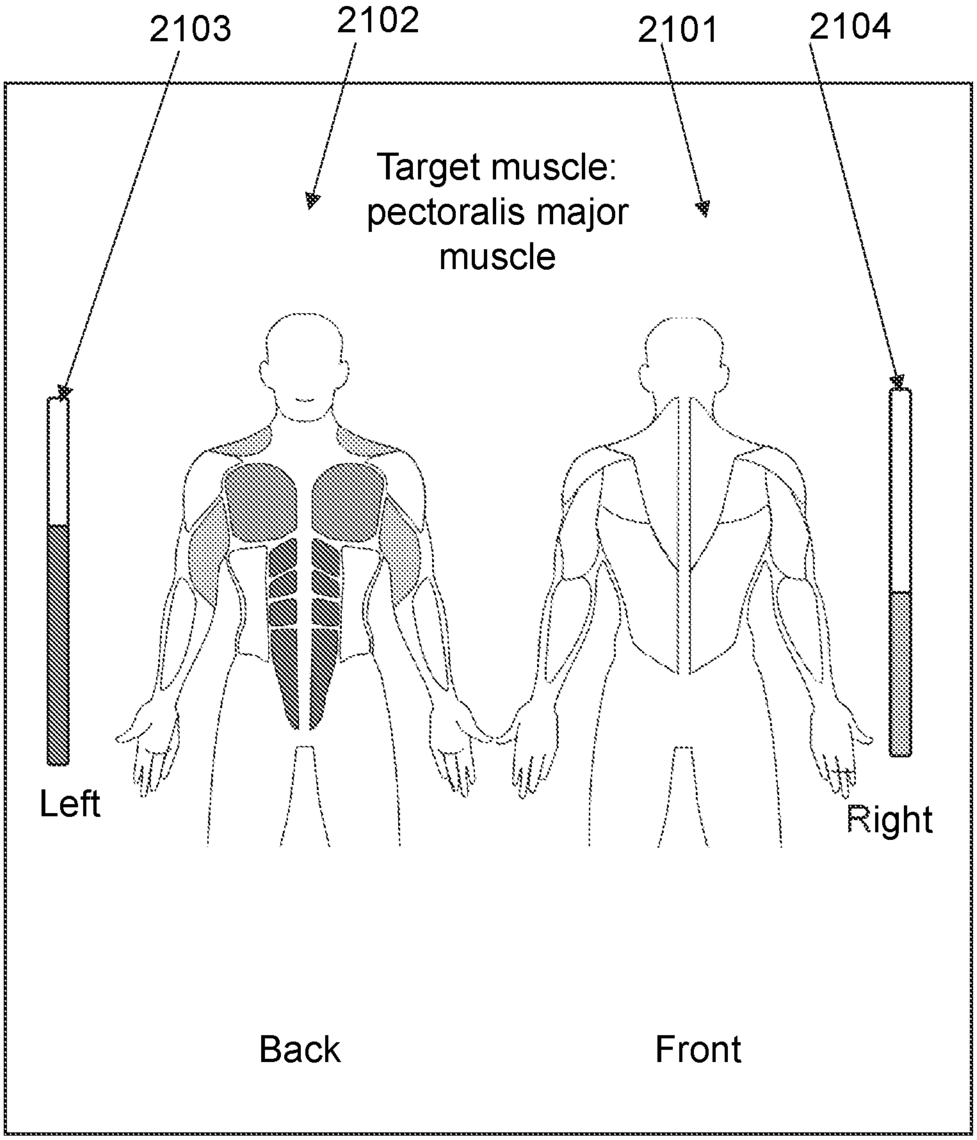
FIG. 21B is an example diagram of a motion monitoring interface according to some embodiments of the present disclosure.

In some embodiments, as shown in FIG. 21B, an interface of the display device may display a front muscle distribution map 2101 and a back muscle distribution diagram 2102 of a human body. When the user starts to exert force, a color of a muscle corresponding to an exertion part of the user in the human muscle distribution map (e.g., the front muscle distribution map 2101 and the back muscle distribution map 2102) may change, so that the user can intuitively feel the exertion strength of the muscle according to the color change corresponding to the muscle in the human muscle distribution map. For example, when a user performs a sit-up movement, an exertion strength of a muscle such as a rectus abdominis muscle, an external oblique muscle, an internal oblique muscle, and a transverse muscle of abdomen of the user's abdomen, and a trapezius muscle of the user's shoulder may be displayed in the human muscle distribution map. In some embodiments, the greater the exertion strength of a certain muscle of the user, the darker the color corresponding to the muscle in the human muscle distribution map (e.g., the closer to red).

In some embodiments, the processing module 220 and/or the user may determine whether the sit-up movement is standard or not according to the exertion strength of muscles of different positions. For example, if the exertion strength of the rectus abdominis muscle, the external oblique muscle, the internal oblique muscle, and the transverse muscle of the user's abdomen is greater than a first strength threshold (the first strength threshold may be set according to the exertion strength of the corresponding muscle when a professional performs a standard sit-up movement), and when the exertion strength of the trapezius muscle of the user's shoulder is smaller than a second strength threshold (the second strength threshold may be set according to the exertion strength of the corresponding muscle when the professional performs the standard sit-up movement), the processing module 220 may determine that the sit-up movement of the user is standard. Otherwise, the processing module 220 may determine that the sit-up movement of the user is non-standard.

It should be noted that the front muscle distribution map 2101 and the back muscle distribution map 2102 of the human body shown in FIG. 21B are only examples. The front muscle distribution map 2101 and the back muscle distribution map 2102 of the human body may be arranged up and down, left and right, or in other arrangement modes easy to observe in the interface.

In some embodiments, the input/output module 260 may obtain a user input regarding a target muscle. The target muscle may refer to a muscle that the user pays more attention to during the motion. For example, the target muscle may be a muscle that the user focuses on during an exercise. In some embodiments, a position of the target muscle and/or a count of target muscles may be related to the movement type of the user. For example, when the user performs the deep squat movement, the target muscle may include the gluteus maximus, the quadriceps femoris muscle, a tibialis anterior muscle, or the like, or any combination thereof. As another example, when the user performs the sit-up movement, the target muscle may include the rectus abdominis muscle, the external oblique muscle, the internal oblique muscle, the transverse muscle of abdomen, the trapezius muscle, or the like, or any combination thereof. In some embodiments, the processing module 220 may determine the movement type of the user based on the movement signal, and determine the target muscle according to the movement type of the user automatically. In some embodiments, the user may determine the movement type manually, and the processing module 220 may determine the target muscle according to the movement type input by the user based on a corresponding relationship between the movement type and the target muscle. In some embodiments, the user may determine the target muscle manually. For example, the user may set a specific muscle as the target muscle by clicking the specific muscle in the human muscle distribution map. As another example, the user may set a specific muscle as the target muscle by inputting a name of the specific muscle in the interface of the display device.

In some embodiments, the interface of the display device may include a status bar (e.g., a status bar 2103 and a status bar 2104 shown in FIG. 21B). The status bar may be configured to display information of the target muscle (e.g., an exertion strength of the target muscle). For example, when the target muscle input by the user is a pectoralis major muscle, the exertion strength of the pectoralis major muscle may be displayed through the status bar. In some embodiments, a color of the status bar may be related to the exertion strength of the target muscle. For example, the darker the color of the status bar, the greater the exertion strength of the target muscle. By displaying the status bar in the interface, the user may feel the exertion strength of the target muscle more intuitively, and the exertion strength of the muscle may be characterized more quantitatively. In some embodiments, the status bar may display a proportional relationship between the exertion strength of the target muscle and a standard exertion strength (or the maximum exertion strength). The standard exertion strength may be set according to an exertion strength corresponding to a muscle when the professional performs a standard movement. The maximum exertion strength may be set according to an exertion strength limit of a human muscle. For example, if the status bar is full, it may indicate that the exertion strength of the target muscle of the user is consistent with the standard exertion strength. The user may more intuitively feel a difference between his/her exertion strength of muscle and the standard exertion strength of muscle through the status bar displayed in the interface, so that the user can timely adjust his/her exertion strength of muscle.

In some embodiments, a count of status bars may be related to a count of target muscles. For example, when the user sets a triceps brachii muscle as the target muscle, two status bars may be displayed on left and right sides of the interface, respectively. The left status bar (e.g., the status bar 2103 shown in FIG. 21B) may be configured to display an exertion strength of a triceps brachii muscle on the left arm of the user. The right status bar (e.g., the status bar 2104 shown in FIG. 21B) may be configured to display an exertion strength of a triceps brachii muscle on the right arm of the user. The exertion strengths of the target muscles on the left and right sides of the user may be displayed through two status bars, which may help the user determine whether the exertion strengths of the muscles on the left and right sides of the body are balanced during the motion, so as to avoid physical damage caused by uneven force on the left and right sides of the body. It should be noted that the status bars shown in FIG. 21B are only examples. The count of the status bars may be any numeric value. The status bar may be set at any position of the interface.

In some embodiments, the input/output module 260 may include a sound output device (e. g., a speaker). The sound output device may make a sound (e.g., a sound of flame burning, bells, water flow), and a volume of the sound may be related to the exertion strength of the target muscle. For example, the volume of the sound may be positively related to the exertion strength of the target muscle, that is, the greater the exertion strength of the target muscle, the greater the volume of the sound; and the weaker the exertion strength of the target muscle, the smaller the volume of the sound. In some embodiments, the sound output device may include a left channel and a right channel, and different channels may correspond to the exertion strengths of different target muscles. For example, the sound from the left channel may correspond to the exertion strength of the target muscle on the left side of the user's body (e.g., the triceps brachii muscle on the left arm), and the sound from the right channel may correspond to the exertion strength of the target muscle on the right side of the user's body (e.g., the triceps brachii muscle on the right arm). By using the multi-channel voice mode of the sound output device, the user may feel the exertion strengths of the muscles in different parts of the body. The user may determine whether the exertion strengths of the muscles on the left and right sides of the body are balanced during the motion only by hearing, which can further improve the user's sense of experience.

It should be noted that the above description regarding the process 2100 is merely provided for the purpose of illustration, and not intended to limit the scope of the present disclosure. For those skilled in the art, various amendments and changes can be made to the process 2100 under the guidance of the present disclosure. For example, the step 2120 may be divided into a plurality of steps to perform processing and determination of the movement signal, respectively. However, these amendments and changes are still within the scope of the present disclosure.

Figure 22:
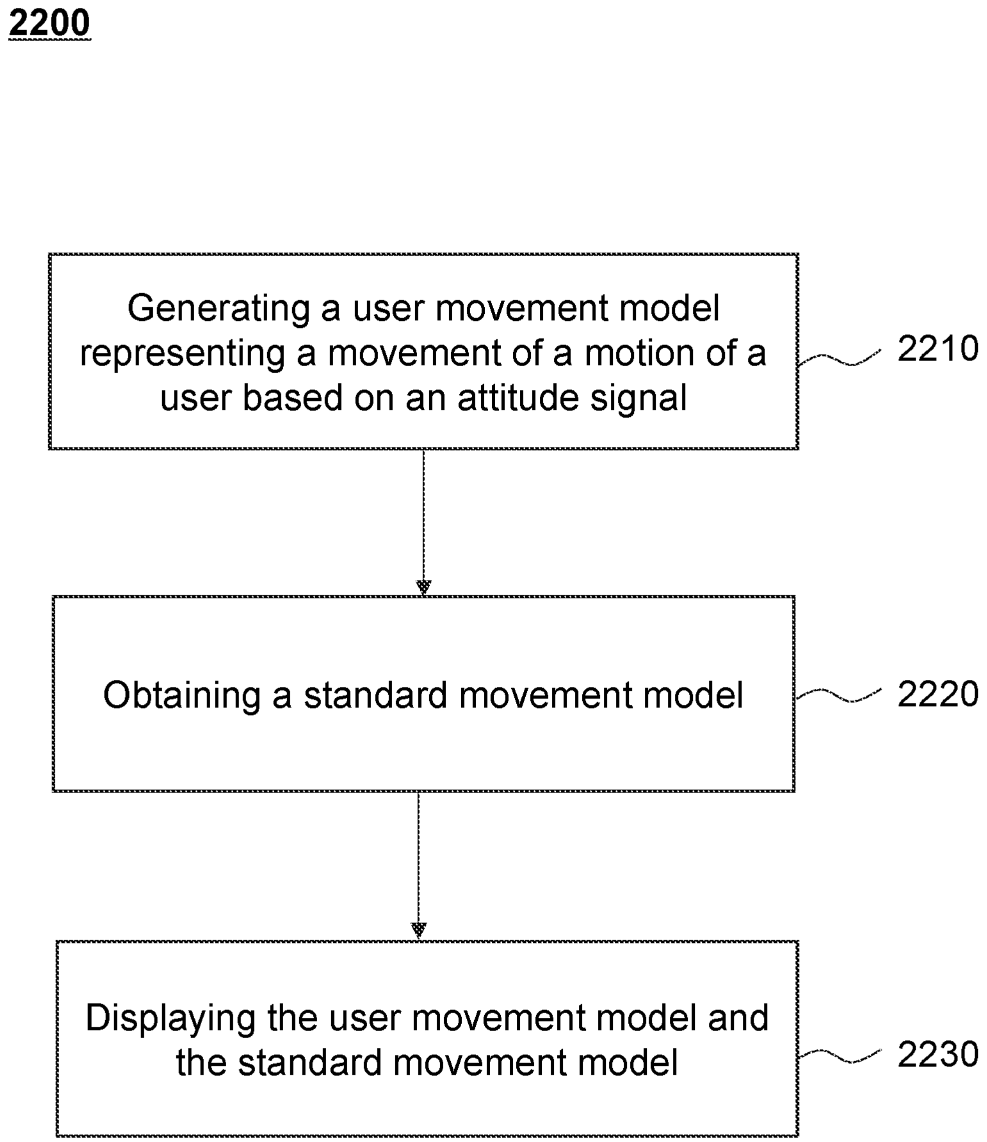
FIG. 22 is an exemplary flowchart of a process for displaying a motion monitoring interface according to some embodiments of the present disclosure.

FIG. 22 is a flowchart illustrating an exemplary process for displaying a motion monitoring interface according to some embodiments of the present disclosure. As shown in FIG. 22, the process 2200 may include the following steps.

In step 2210, a user movement model representing a movement of the motion of the user may be generated based on an attitude signal.

In some embodiments, the step 2210 may be performed by the processing module 220. In some embodiments, the user movement model may include a user three-dimensional (3D) movement model, a user three-dimensional (2D) movement model, etc. The user 3D movement model and/or the user 2D movement model may reproduce the movement of the motion of the user. It may be understood that the movement reproduction of the motion of the user may reflect a posture of the motion of the user to a certain extent, without requiring the reproduced movement to be completely consistent with the real movement of the user.

In some embodiments, the processing module 220 may generate the user movement model representing the movement of the motion of the user based on the attitude signal collected by an attitude sensor. In some embodiments, a plurality of attitude sensors may be placed at different positions of the wearable device 130 (e.g., positions of the wearable device 130 corresponding to a trunk, limbs and joints) according to an attitude signal required to be obtained to measure the attitude signals corresponding to different parts of a human body. The attitude signals corresponding to the different parts may reflect a relative motion situation between different parts of the human body. In some embodiments, the attitude signal may be associated with a type of attitude sensor. For example, when the attitude sensor is an angular velocity triaxial sensor, the obtained attitude signal may be angular velocity information. As another example, when the attitude sensor is an angular velocity triaxial sensor and an acceleration triaxial sensor, the obtained attitude signal may be the angular velocity information and acceleration information. As yet another example, when the attitude sensor is a strain gauge sensor, the strain gauge sensor may be set at a joint position of the user. By measuring a magnitude of a resistance in the strain gauge sensor that changes with a tensile length, the obtained attitude signals may include displacement information, stress, etc. The attitude signals may characterize a bending angle and a bending direction at the joint of the user. As yet another example, the attitude sensor may be an ultrasonic sensor that is set at a fixed position of the joint or the limb of the user. A position of the sensor may be determined by measuring the time of flight (TOF) of an acoustic wave, so as to determine an attitude of the user. The attitude signal obtained by the attitude sensor and feature information corresponding to the attitude sensor (e.g., an angular velocity direction, an angular velocity value, an acceleration value of angular velocity, angle, displacement information, stress, etc.) may reflect a posture of the motion of the user. The processing module 220 may generate the user movement model representing the movement of the motion of the user based on the posture of the motion of the user. For example, the processing module 220 may generate a virtual character (e. g., a 3D or 2D animation model) to display the posture of the motion of the user.

In some embodiments, the processing module 220 may determine other types of information related to the motion of the user (e.g., muscle information) based on other types of movement signals (e.g., an electromyographic signal), and display the other types of information related to the motion of the user on the user movement model. In some embodiments, the processing module 220 may determine an exertion strength of at least one muscle of the user based on the electromyographic signal, and the processing module 220 may display the exertion strength of the at least one muscle of the user on a corresponding position of the user movement model. For example, when the user performs a deep squat movement, the processing module 220 may obtain the electromyographic signal from an electromyography sensor set at a position such as a gluteus maximus, a quadriceps femoris muscle, a tibialis anterior muscle, etc. The processing module 220 may determine the exertion strength of the muscle such as the gluteus maximus, the quadriceps femoris muscle, and the tibialis anterior muscle, respectively, according to the electromyographic signal, and display the exertion strength of the muscle of the gluteus maximus, the quadriceps femoris muscle, and the tibialis anterior muscle at the position corresponding to the gluteus maximus, the quadriceps femoris muscle, and the tibialis anterior muscle in the user movement model. In some embodiments, different muscle strengths may correspond to different display colors. By displaying the other types of information related to the motion of the user in the user movement model at the same time, the user can understand the motion state more intuitively and comprehensively.

In step 2220, a standard movement model may be obtained.

In some embodiments, the step 2220 may be performed by the obtaining module 210. In some embodiments, the standard movement model may be a movement model generated based on standard movement information (e.g., standard attitude information, standard electromyography information) during a motion of a professional (e.g., a fitness instructor). In some embodiments, the standard movement model may include a standard 3D movement model, a standard 2D movement model, etc. The standard 3D movement model and/or the standard 2D movement model may reproduce the movement of the professional. It may be understood that the movement reproduction of the standard movement may reflect a posture of the motion of the professional to a certain extent, without requiring the reproduced movement to be completely consistent with the real movement of the professional. In some embodiments, the standard movement model may display a plurality of types of information related to the motion (e.g., muscle information) during the motion of the professional.

In some embodiments, different types of movements may correspond to different standard movement models. For example, a sit-up movement may correspond to a sit-up standard movement model, and a dumbbell flying bird movement may correspond to a dumbbell flying bird standard movement model. In some embodiments, a plurality of standard movement models corresponding to a plurality of motion types may be stored in a storage device of the motion monitoring system 100 in advance. The obtaining module 210 may obtain, according to the movement type of the user, the standard movement model corresponding to the movement type of the user from the storage device.

In step 2230, the user movement model and the standard movement model may be displayed.

In some embodiments, the step 2230 may be performed by the input/output module 260. In some embodiments, the display device may display the user movement model and the standard movement model simultaneously. For example, the user movement model and the standard movement model may be displayed on top of each other or side by side. By observing and comparing the user movement model and the standard movement model, the user may determine whether the movement of the motion is standard more intuitively and quickly, so as to adjust the movement of the motion in time.

In some embodiments, a determination may be made as whether the movement of the user needs to be adjusted by comparing a degree of coincidence between a contour of the user movement model and a contour of the standard movement model. For example, if the degree of coincidence between the contour of the user movement model and the contour of the standard movement model is greater than a threshold (e.g., 90%, 95%, 98%), it may be determined that the movement of the user is standard and does not need to be adjusted. If the degree of coincidence between the contour of the user movement model and the contour of the standard movement model is smaller than a threshold (e.g., 90%, 95%, 98%), it may be determined that the movement of the user is non-standard. The input/output module 260 may prompt the user to adjust the movement of the motion.

Figure 23A:
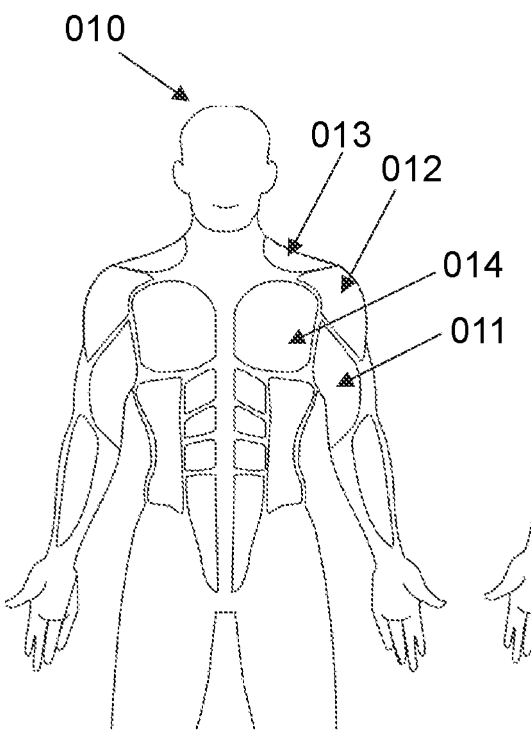
FIG. 23A a schematic diagram of a motion monitoring interface according to some embodiments of the present disclosure.
Figure 23B:
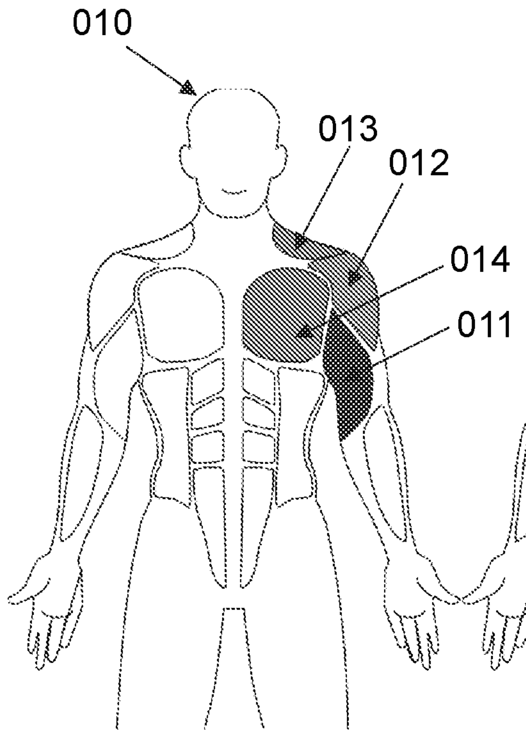
FIG. 23B is a schematic diagram of a motion monitoring interface according to some embodiments of the present disclosure.
Figure 23C:
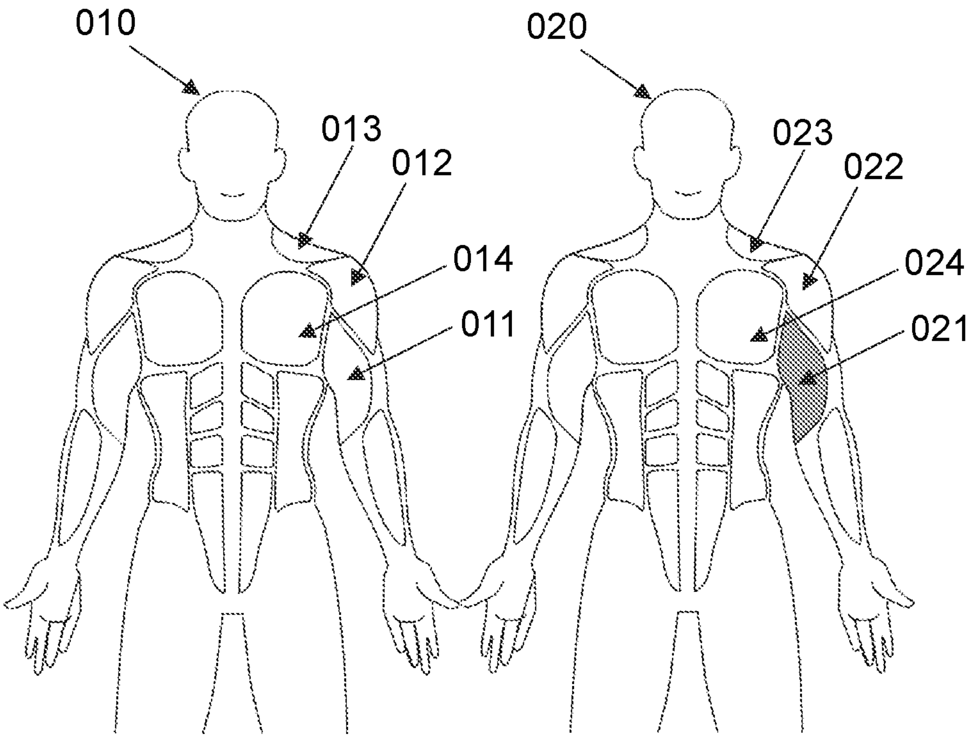
FIG. 23C are schematic diagrams of a motion monitoring interface according to some embodiments of the present disclosure.

In some embodiments, a determination may be made as whether the movement of the user needs to be adjusted by comparing the muscle information displayed on the user movement model with the muscle information displayed on the standard movement model. For the convenience of illustration, a bicep curl movement of a left arm may be taken as an example. In the bicep curl movement, muscles mainly involved in the movement may include a biceps brachii muscle, a deltoid muscle, a trapezius muscle, and a pectoral muscle. FIGS. 23A to 23C are schematic diagrams illustrating motion monitoring interfaces according to some embodiments of the present disclosure. FIGS. 23A to 23C are a user movement model 010 (also referred to as an electromyography animation 010 of a virtual user character) and a standard movement model 020 (also referred to as a reference electromyography animation 020 of a virtual reference character) displayed on the display device, respectively. In FIGS. 23A to 23C, the electromyography animation 010 of the virtual user character may be displayed in a left half of the motion monitoring interface, and the reference electromyography animation 020 of the virtual reference character may be displayed in a right half of the motion monitoring interface. The motion monitoring interface shown in FIG. 23A may correspond to the electromyography animation at a moment before the movement starts. As shown in FIG. 23A, the user and the professional may be in a relaxed state before the movement starts, so all muscles may not exert force. At this time, a user display area 011 corresponding to the biceps brachii muscle, a user display area 012 corresponding to the deltoid muscle, a user display area 013 corresponding to the trapezius muscle, and a user display area 014 corresponding to the pectoral muscle in the electromyography animation 010 of the virtual user character may have no color display. A user display area 021 corresponding to the biceps brachii muscle, a user display area 022 corresponding to the deltoid muscle, a user display area 023 corresponding to the trapezius, and a user display area 024 corresponding to the pectoral muscle in the reference electromyography animation 020 of the virtual reference character may also have no color display.

The motion monitoring interface shown in FIG. 23B may correspond to an electromyography animation at a certain moment in a process of the bicep curl movement. In the process of the bicep curl movement, theoretically, a main exertion point may be the biceps brachii muscle. In some cases, the pectoral muscle may also exert slightly, for example, when the user does not chin up and chest out. In a standard bicep curl movement, the trapezius muscle may not need to be involved in exertion or may exert slightly. As shown in FIG. 23B, a color displayed in the user display area 013 corresponding to the trapezius muscle in the electromyography animation 010 of the virtual user character is darker than a color displayed in the reference display area 023 corresponding to the trapezius muscle in the electromyography animation 020 of the virtual reference character, which may indicate that the trapezius muscle exerts a relatively large force when the user performs the bicep curl movement, and the exertion strength exceeds an exertion strength of the trapezius muscle in the standard bicep curl movement.

The motion monitoring interface shown in FIG. 23C may correspond to an electromyographic animation at a certain moment from an end of the bicep curl movement to a beginning of a next movement cycle. In a set of continuous bicep curl movements, the user may not be in a completely relaxed state from the end of a complete movement cycle to the beginning of a next complete movement cycle. That is, when a barbell reaches the bottom, the biceps muscle cannot be completely relaxed, but may need to maintain a certain amount of exertion strength, so as to achieve the best exercise effect. As shown in FIG. 23C, in the electromyography animation 010 of the virtual user character, the user display area 011 corresponding to the biceps brachii muscle has no color display, which may indicate that the user is in a completely relaxed state. In the reference electromyography animation 020 of the virtual reference character, the color of the reference display area 021 corresponding to the biceps brachii muscle is darker.

To sum up, by observing the electromyography animation 010 of the virtual user character and the reference electromyography animation 020 of the virtual reference character, the user may clearly and intuitively view a difference between the exertion strength of the muscle of the user in the electromyography animation 010 of the virtual user character and the exertion strength of the standard muscle in the reference electromyography animation 020 of the virtual reference character, find problems in the current movement, and adjust the movement in time. Further description regarding displaying the user movement model and the standard movement model may be found in the priority of International Application No. PCT/CN2021/093302, filed on May 12, 2021, the entire contents of which are hereby incorporated by reference.

It should be noted that the above description regarding the process 2200 is merely provided the purpose of illustration, and not intended to limit the scope of the present disclosure. For those skilled in the art, various amendments and changes can be made to the process 2200 under the guidance of the present disclosure. However, these amendments and changes are still within the scope of the present disclosure.

Figure 24:
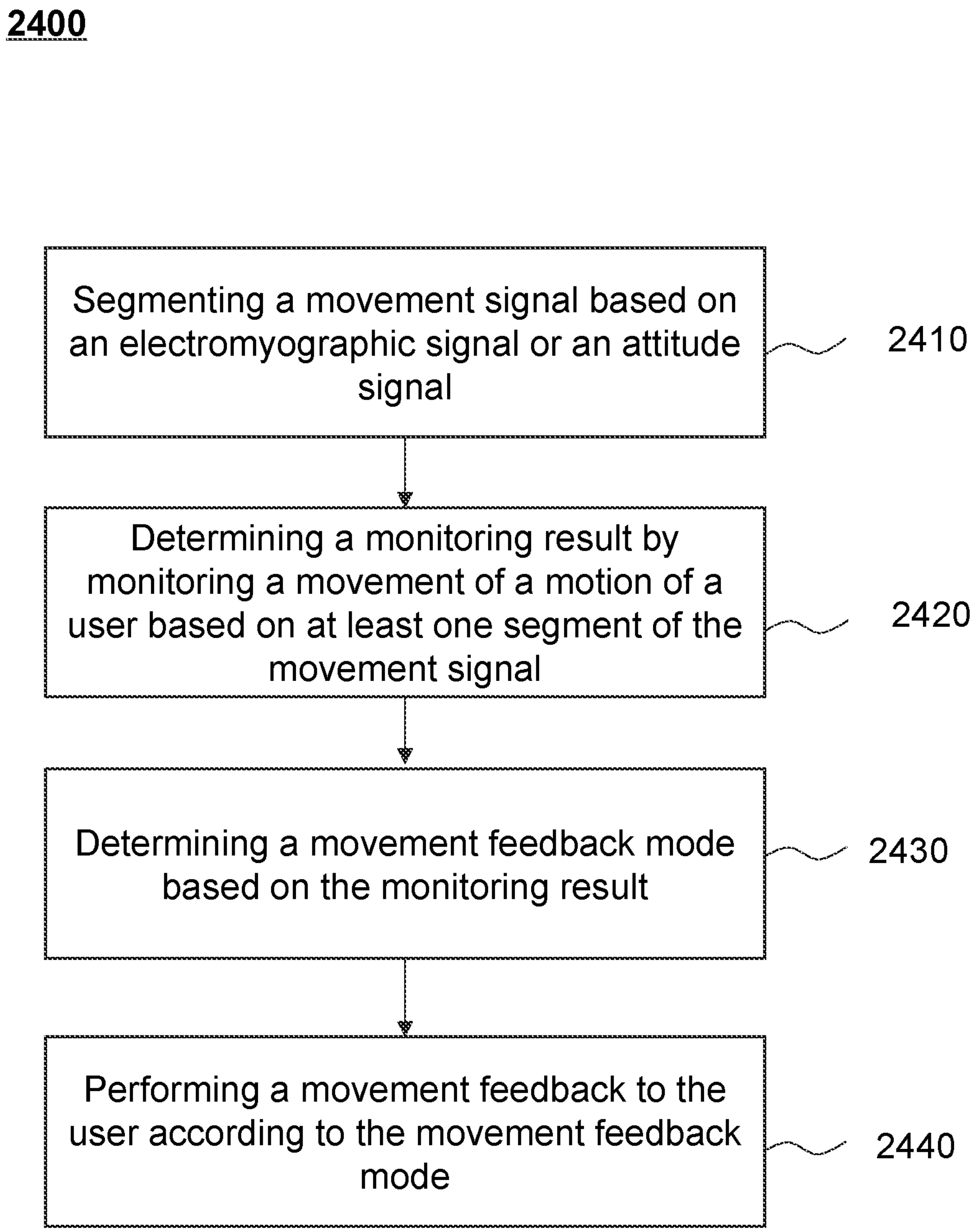
FIG. 24 is an exemplary flowchart of a process for displaying a motion monitoring interface according to some embodiments of the present disclosure.

FIG. 24 is a flowchart illustrating an exemplary process for displaying a motion monitoring interface according to some embodiments of the present disclosure. As shown in FIG. 24, the process 2400 may include the following steps.

In step 2410, a movement signal may be segmented based on an electromyographic signal or an attitude signal.

In some embodiments, the step 2410 may be performed by the processing module 220. In some embodiments, an obtaining process of the movement signal (e.g., the electromyographic signal, the attitude signal) during a motion of a user may be continuous, and a movement during the motion of the user may be a combination of a plurality of sets of movements or a combination of movements of different movement types. In order to analyze each movement during the motion of the user, the processing module 220 may segment the movement signal of the user based on the electromyographic signal or the attitude signal during the motion of the user. In some embodiments, segmenting the movement signal may refer to dividing the movement signal into signal segments with a same time duration or different time durations, or extracting one or more signal segments with a specific time duration from the movement signal. In some embodiments, each segment of the movement signal may correspond to one or more complete movements of the user. For example, when the user performs a deep squat movement, the user goes from a standing posture to a squatting posture, gets up, and returns to the standing posture, which may be regarded as completing the deep squat movement. The movement signal collected by the obtaining module 210 in the process may be regarded as a segment (or a cycle) of movement signal. After that, the movement signal collected by the obtaining module 210 that the user completes a next squat movement may be regarded as another segment of movement signal. A change of each movement step during the motion of the user may cause the electromyographic signal and the attitude signal of a corresponding part to change. Based on the situation, the processing module 220 may segment the movement signal of the user based on the electromyographic signal or the attitude signal. For example, the processing module 220 may segment the movement signal of the user based on feature information corresponding to the electromyographic signal or feature information corresponding to the attitude signal. Detailed description regarding the segmenting the movement signal based on the electromyographic signal or the attitude signal may be found in FIGS. 6 to 8 of the present disclosure and related description thereof.

In step 2420, a monitoring result may be determined by monitoring a movement of the motion of the user based on at least one segment of the movement signal.

In some embodiments, the step 2420 may be performed by the processing module 220. In some embodiments, the at least one segment of the movement signal may be a movement signal of the user in at least one training process. In some embodiments, the training process may refer to a process in which a user completes a training movement. For example, the user completing a deep squat movement may be the training process. In some embodiments, the training process may also refer to a process in which the user completes a plurality of same or different training movements. For example, the user completing a plurality of deep squat movements successively may be a training process. As another example, the user completing the deep squat movement and a jumping movement in situ successively may be a training process. In some embodiments, the training process may refer to a process in which the user completes training movements within a certain period of time. For example, the training process may be a process of training movements completed within a day, a week, a month, or a year.

It should be noted that a segment of movement signal may be a movement signal of a complete training process or a movement signal of a part of the training process in a complete training process. In some embodiments, for a complex complete training process, there may be different exertion modes and different exertion strengths of muscles at different stages of the complete training process, that is, there may be different movement signals at different stages of the training process. The real-time performance of monitoring of the movement of the user may be improved by monitoring the movement signals at the different stages of the complete training process.

In some embodiments, the monitoring result may include a movement type, a movement quantity, a movement quality, a movement time, physiological parameter information, a core stability, an interval time, an expected recovery time of the user, or the like, or any combination thereof, during the at least one training process. The physiological parameter information of the user may include, but is not limited to, a heart rate (e.g., an average heart rate, the maximum heart rate), a blood pressure, a body temperature, an energy consumption during the motion, or the like, or any combination thereof. In most training, muscles of the abdomen and the waist may need to be kept in a state of tension to maintain stability of the trunk, improve training efficiency and reduce a risk of injury. An ability of the muscles of the waist and the abdomen to maintain exertion may be called the core stability. The interval time may refer to a time interval between two consecutive movements. For example, when a user performs a deep squat movement, the interval time may refer to the time interval between a first deep squat movement and a second deep squat movement. The expected recovery time may refer to a time it takes for each part of the body (e.g., muscle) to recover from a motion state to a normal state after the user completes the motion. For example, the expected recovery time may be the time it takes for the muscle of the user to recover from a fatigue state to a relaxed state after the user completes the motion.

In some embodiments, the monitoring result may be determined by monitoring the motion of the user based on the at least one segment of movement signal. In some embodiments, the monitoring result (e.g., the movement type, the movement quality) may be determined based on the at least one segment of movement signal (e.g., the electromyographic signal, the attitude signal) and at least one segment of preset movement signal (e.g., a preset electromyographic signal, a preset attitude signal). The at least one preset movement signal may be a standard movement signal collected by a sensor when a professional performs a standard movement. The preset movement signal may be stored in a database in advance. In some embodiments, the movement type or the movement quality during the motion of the user may be determined by determining a matching degree between feature information corresponding to the at least one segment of movement signal and feature information corresponding to the at least one segment of preset movement signal. For example, if it is determined that the matching degree between the feature information corresponding to a segment of movement signal of the user and the feature information corresponding to a segment of the preset movement signal is higher than a certain threshold (e.g., 95%), it may be determined that the movement type during the motion of the user is consistent with the movement type of the preset movement signal. As another example, if it is determined that the matching degree between a segment of movement signal of the user and a segment of preset movement signal of a same type is higher than a certain threshold (e.g., 95%), it may be determined that the movement quality of the user during the motion meets a requirement and does not need to be adjusted. In some embodiments, the monitoring result (e.g., the heart rate and the energy consumption) of the motion of the user may be determined based on the feature information corresponding to physiological signals of the user (e.g., electro-cardio signals and respiratory signals) collected by different types of sensors. Further description regarding determining the motion type, the movement type, the movement quantity, the movement quality, the movement time, the physiological parameter information, etc. of the user may be found in FIGS. 19-20 of the present disclosure and related descriptions thereof.

In some embodiments, the method for determining the monitoring result by monitoring the user based on the at least one segment of movement signal may be an algorithm not based on another segment of movement signal. In some embodiments, the algorithm may be based on a machine learning model. The movement signal may be input into the machine learning model, and the movement type, the movement quantity, the movement quality, or an error point of the movement may be given through a neural network model or a traditional machine learning model. In some embodiments, the algorithm may be based on an algorithm based on state machine transition. When the movement experiences a series of states, the movement type, movement quantity, the movement quality, or the error point of the movement may be output. In some embodiments, the algorithm may be a combination of threshold judgments. The movement type, the movement quantity, the movement quality, or the error point of the movement may be given by judging whether the movement signal meets a series of conditions.

In some embodiments, the core stability of the user may be determined based on the electromyographic signal obtained by an electromyography sensor. For example, the core stability of the user may be determined based on a proportion of an exertion time of an abdominal muscle of the use during a training process. In the training process, the greater the proportion of the exertion time of the abdominal muscle of the user, the better the core stability of the user. In some embodiments, the core stability of the user may be determined based on the attitude signal obtained by an attitude sensor. For example, the core stability of the user may be determined based on a motion amplitude of the trunk of the user during a training process. In some embodiments, the core stability of the user may be determined based on the electromyographic signal and the attitude signal. For example, the core stability of the user may be determined based on the proportion of the exertion time of the abdominal muscle of the user and the motion amplitude of the trunk of the user in the training process.

In some embodiments, the monitoring result may include muscle information of the user. In some embodiments, the muscle information of the user may include, but is not limited to, a participation degree of at least one muscle, an energy consumption of the at least one muscle, a fatigue degree of the at least one muscle, a balance of at least two muscles, an ability of the at least one muscle, or the like, or any combination thereof.

The participation degree (also referred to as a contribution degree) and the fatigue degree of muscle may indicate whether a target training muscle (e.g., a key training muscle) has been effectively exercised during the motion, and whether other non-target training muscles have exertion compensation, so that the movement quality of the user may be evaluated. In some embodiments, the energy consumption of muscle may be determined based on the electromyographic signal of the muscle of the user and a training time. In some embodiments, the participation degree of each muscle may be determined based on a proportion of an energy consumption of each muscle to an energy consumption of all muscles during the motion of the user. For example, if the energy consumption of all muscles in a certain training is 500 kcal and the energy consumption of pectoral muscles is 250 kcal, the participation degree (the contribution degree) of the pectoral muscles may be determined as 50%. In some embodiments, the participation degree of muscle may be determined based on the feature information of the electromyographic signal. The feature information of the electromyographic signal may include amplitude information (e.g., a mean square amplitude, an integrated electromyogram, an amplitude envelope) and/or frequency information (e.g., an average power frequency, a median frequency, a short-term zero crossing rate) of the electromyographic signal. For example, the participation degree of muscle may be determined based on a percentage of integrated electromyogram of the muscle during a training process (or during a movement).

In some embodiments, the electromyographic signal may be preprocessed, and the participation degree of muscle may be determined based on the amplitude information and/or the frequency information of the preprocessed electromyographic signal. In some embodiments, since different muscles have different types of muscle fibers and different counts of muscles, magnitudes of electromyographic signals that the different muscles can emit may be also different. For example, under a same degree of subjective effort, a muscle group such as the biceps brachii muscle, etc. may be more likely to emit a relatively large electromyographic signal, while a muscle group such as the pectoral muscle, etc. may emit a relatively small electromyographic signal. Therefore, the electromyographic signal may be normalized to eliminate or weaken a difference in the magnitude of the electromyographic signal emitted from the different muscle groups. In some embodiments, there may be a nonlinear relationship between the electromyographic signal and an exertion strength of the user. For example, when the exertion strength of the user is relatively large, the amplitude of the electromyographic signal may increase slowly. Therefore, the amplitude of electromyographic signal may be nonlinearized, and the processed electromyographic signal may be used to determine the participation degree of muscle.

The fatigue degree of muscle may be configured to evaluate the maximum capacity and a growth capacity of the muscle of the user, which may reflect whether the muscle of the user has been adequately exercised. When the user performs the motion (especially a strength training), the motion may make the muscle enter a fatigue state, and an excessive recovery may be formed using natural repair of a body, resulting in an increase in strength, volume, endurance and explosive power of the muscle. Therefore, it is necessary to evaluate the fatigue degree of the muscle of the user after the motion. In some embodiments, the fatigue degree of muscle may be determined based on the feature information of the electromyographic signal. For example, the fatigue degree of muscle may be determined based on a degree of change (e.g., a degree of decline) of a feature value (e.g., an average power frequency, a median frequency, a short-term zero crossing rate) of the electromyographic signal during at least one training process (e.g., between a plurality of movements). As another example, if it is detected that the amplitude of the electromyographic signal shows a decline trend during a process of a user performing the plurality of movements, it may indicate that the muscle has gradually entered the fatigue state. The faster the amplitude of the electromyographic signal declines (that is, the higher the slope of the amplitude), the higher the fatigue degree of muscle. As another example, if the amplitude of the electromyographic signal is detected to have a high degree of jitter, it may indicate that the muscle has gradually entered the fatigue state. As another example, the fatigue degree of muscle may be determined based on a degree of stability of the electromyography amplitude envelope. The lower the degree of stability of the electromyography amplitude envelope, the higher the fatigue degree of muscle. In some embodiments, the fatigue degree of muscle may be determined based on the feature information of the attitude signal (e.g., an angular velocity, an angular velocity direction, an acceleration of angular velocity, an angle, displacement information, and stress). For example, if it is detected that the attitude signal has a high degree of jitter, and the movement of the user is jittered or severely deformed, it may indicate that the muscle is in the fatigue state.

In some embodiments, the fatigue degree of muscle may be determined using a trained machine learning model. For example, the trained machine learning model may be generated by training an initial model based on sample information. In some embodiments, the sample information may include sample movement signals and sample fatigue degrees of muscles of a plurality of users. The sample fatigue degree may be determined based on the sample movement signal. In some embodiments, the initial model may be trained based on the sample information using a training algorithm to generate the trained machine learning model. Exemplary training algorithms may include a gradient descent algorithm, a Newton algorithm, a quasi-Newton algorithm, a conjugate gradient algorithm, a generation adversarial learning algorithm, etc. The trained machine learning model may be used to determine the fatigue degree of the muscle of the user based on the movement signal of the user. For example, the movement signal of the user may be input into the trained machine learning model, and the trained machine learning model may output the fatigue degree of the muscle of the user.

In some embodiments, a determination may be made as whether a current motion exceeds a load of the user according to the fatigue degree of the muscle of the user. For example, when it is determined that the fatigue degree of a certain muscle of the user exceeds a first fatigue threshold, it may be determined that the current amount of motion has exceeded the load of the user. At this time, a prompt may be sent to the user to remind the user to reduce the amount of motion or stop the motion to prevent injury. As another example, when it is determined that the fatigue degree of a certain muscle of the user is lower than a second fatigue threshold, it may be determined that the current amount of motion of the user is insufficient to achieve an expected training effect, or it may indicate that the user still has more spare energy. At this time, a prompt may be sent to the user to remind the user to increase the amount of motion to ensure the training effect. In some embodiments, the recovery time may be estimated according to the fatigue degree of the user and fed back to the user to help the user plan a next motion in advance.

In some embodiments, the balance of at least two muscles may be a motion balance of left and right muscles in a same muscle group of the user's body. For example, the balance of at least two muscles may refer to a balance of the left pectoralis major muscle and the right pectoralis major muscle of the user. When the muscles on the left and right sides of the body are unbalanced during the motion of the user, it may not only affect the beauty of the movement, but also affect a standard degree of the movement. When the muscles on the left and right sides of the body are unbalanced, the user may face a risk of injury. Therefore, it is necessary to monitor the balance of the left and right muscles of the user's body. In some embodiments, the balance of muscles may include a balance of exertion strengths of muscles, a balance of fatigue degrees of muscles, a balance of energy consumptions of muscles, etc.

In some embodiments, the balance of at least two muscles may be determined based on the feature information of the movement signal (e.g., the electromyographic signal, the attitude signal). In some embodiments, a determination may be made as whether the exertion strengths of the two muscles is balanced by comparing the amplitude information of the electromyographic signals of the two muscles (e.g., the root mean square amplitude, the integral electromyogram, the amplitude envelope). For example, if a difference between the amplitude information of the electromyographic signals of the two muscles is within a threshold range, it may be considered that the exertion strengths of the two muscles are substantially the same. In some embodiments, a determination may be made as whether the fatigue degrees of the two muscles are the same by comparing the frequency information of the electromyographic signals of two muscles (e.g., the average power frequency, the median frequency, the short-term zero crossing rate). For example, if a difference between the frequency information of the electromyographic signals of the two muscles is within a threshold range, it may be considered that the fatigue degrees of the two muscles are substantially the same. In some embodiments, a determination may be made as whether motion speeds and motion angles of left and right limbs of the user's body are consistent by comparing the feature information of the attitude signals of the two muscles (e.g., the acceleration and the angular velocity), so as to determine the balance of the posture of the movement of the user. In some embodiments, the balance degree of left and right muscles of the user's body may be comprehensively determined based on the balance of the exertion strengths of the at least two muscles, the balance of the fatigue degrees of the at least two muscles, and the balance of the movement posture of the motion of the user. In some embodiments, when it is determined that the balance degree of the left and right muscles of the user is relatively low, a prompt may be sent to the user to remind the user to strengthen exercise of some muscle groups or improve the posture of the current exercise to ensure the effect of the motion.

The ability of muscle may be a training amount when the user reaches exhaustion during training. In some embodiments, the ability of muscle may be represented by a characteristic amount determined by one or more of characteristics such as an energy consumption, a count of groups of motion, a count of motion times, a weight, a time, etc. For example, the ability of muscle may be expressed by a total work obtained by multiplying a total count of times of motion by a total weight, or expressed by a power obtained by multiplying the total count of times of motion by the total weight and dividing by the time. In some embodiments, the fatigue degree of muscle of the user may be determined based on the electromyographic signal and/or the attitude signal, the training amount (e.g., an energy consumption amount) of the user when the fatigue degree of muscle of the user is relatively high (e.g., higher than a fatigue threshold) may be determined, and the training amount (e.g., the energy consumption amount) of the user at this time may be used as the ability of muscle of the user.

In step 2430, a movement feedback mode may be determined based on the monitoring result.

In some embodiments, the step 2430 may be performed by the processing module 220.

In some embodiments, the movement feedback mode may include a feedback manner, a feedback priority, a feedback content, or the like, or any combination thereof. In some embodiments, the feedback mode may include, but is not limited to, a text prompt, a voice prompt, an image prompt, a video prompt, a vibration prompt, a pressure prompt, or the like, or any combination thereof. For example, the text prompt may be displayed through a display of the input/output module 260. The voice prompt may be realized by playing sound through a speaker in the input/output module 260 and/or the wearable device 130. The image prompt and the video prompt may be realized by the display of the input/output module 260 and/or the wearable device 130. The vibration prompt may be realized by a vibration of a vibration module in the input/output module 260 and/or the wearable device 130. The pressure prompt may be realized through electrodes in the wearable device 130. In some embodiments, the movement feedback mode may be determined according to the movement type of the motion of the user. For example, when the user is running, since the text prompt is not easy to be received by the user, the voice prompt, the vibration prompt, or the pressure prompt may be selected to feedback the monitoring result to the user.

In some embodiments, the feedback priority may include immediate feedback, feedback after a movement is completed, feedback after a training is completed, etc. The immediate feedback may refer to that the input/output module 260 immediately performs feedback to the user according to the corresponding feedback mode when the user has a problem (e.g., an exertion strength of the muscle is relatively high) during the motion. The feedback after a movement/training is completed may refer to that the input/output module 260 performs feedback to the user in a form of a training suggestion after the user completes a movement/training. In some embodiments, the feedback priority of the movement may be determined based on the movement type of the user. For example, when the movement type of the motion of the user is a movement that is easy to cause injury to the user, for example, a deep squat movement is easy to cause knee buckle, resulting damage to the user's knee, at this time, the priority of the movement feedback mode may be relatively high, and a more eye-catching feedback mode (e.g., a text prompt with signs) may be used to perform feedback, so that the user may receive the feedback and adjust the movement posture in time. As another example, if the movement type of the motion of the user is a bicep curl movement, the user's arm is likely to be in a relaxed state without continuous exertion at the lowest point, resulting in low training efficiency, but may not cause harm to the user's body. At this time, the priority of the movement feedback mode may be relatively low, for example, the feedback may be performed through the text prompt after the user completes the training.

In some embodiments, a determination may be made as whether an error occurs in the movement of the motion of the user based on the monitoring result, and the feedback priority of the movement may be determined according to a type of movement error of the motion of the user. The type of movement error may reflect a degree of damage to the user's body when the user makes the movement error. In some embodiments, the type of movement error may be divided into a type of primary movement error, a type of secondary movement error, and a type of tertiary movement error. The type of primary movement error may be a type of movement error that is easy to cause injury (e.g., knee buckle during the deep squat movement) to the user. The type of secondary movement error may be a type of movement error in which a target training muscle has not been effectively exercised (e.g., arms are bent to exert when the user performs the seated chest press, so that the biceps brachii muscle is exercised but the pectoral muscles are not exercised). The type of tertiary movement error may be a type of movement error that leads to a relatively low training efficiency (e.g., running too slow). In some embodiments, when the type of movement error is the type of primary movement error, the feedback priority may be the immediate feedback. When the type of movement error is the type of secondary movement error, the feedback priority may be the feedback after a movement is completed. When the type of movement error is the tertiary movement error, the feedback priority may be the feedback after a training is completed.

In some embodiments, the feedback content may include the monitoring result (e.g., the movement type, the movement quantity, the movement quality, the movement time), the type of movement error, a degree of movement completion, the training suggestion, or the like, or any combination thereof. In some embodiments, the processing module 220 may determine the feedback content according to the motion monitoring result such as the movement type and the type of movement error of the motion of the user. For example, after the user completes a training, the input/output module 260 may feedback training information (e.g., the movement type, the movement quantity, the movement quality, the movement time) during the training process to the user, so as to help the user fully understand the training process. As another example, when the user makes a movement error during the motion (e.g., knee buckle during the deep squat movement), the input/output module 260 may prompt the user of the current movement error to help the user adjust the movement in time. In some embodiments, when the user makes a movement error (e.g., an exertion of a certain muscle is wrong) during the motion, the error of the user may be displayed at a position corresponding to the certain muscle in the user movement model. For example, a manner such as an edge flicker, a sign, a word, a symbol (e.g., an exclamation mark), etc. may be used at the position corresponding to the certain muscle in the user movement model to prompt the user that the exertion of the certain muscle at the position is wrong.

In step 2440, a movement feedback may be performed to the user according to the movement feedback mode.

In some embodiments, the step 2440 may be performed by the input/output module 260.

In some embodiments, the input/output module 260 may display the monitoring result to the user in a form of a text, a chart (e.g., a line chart, a bar chart, a pie chart, a histogram), a sound, an image, a video, or the like, or any combination thereof.

FIG. 25 is a schematic diagram illustrating a motion monitoring interface according to some embodiments of the present disclosure. As shown in FIG. 25, basic training information and exercise counts after a user completes a training is displayed in the form of a text in an interface 2500. In some embodiments, the user may formulate a training plan in advance before the training starts. After the training, the user may compare the basic training information after the training with the training plan to help the user determine a degree of completion of the training plan.

Figure 26:
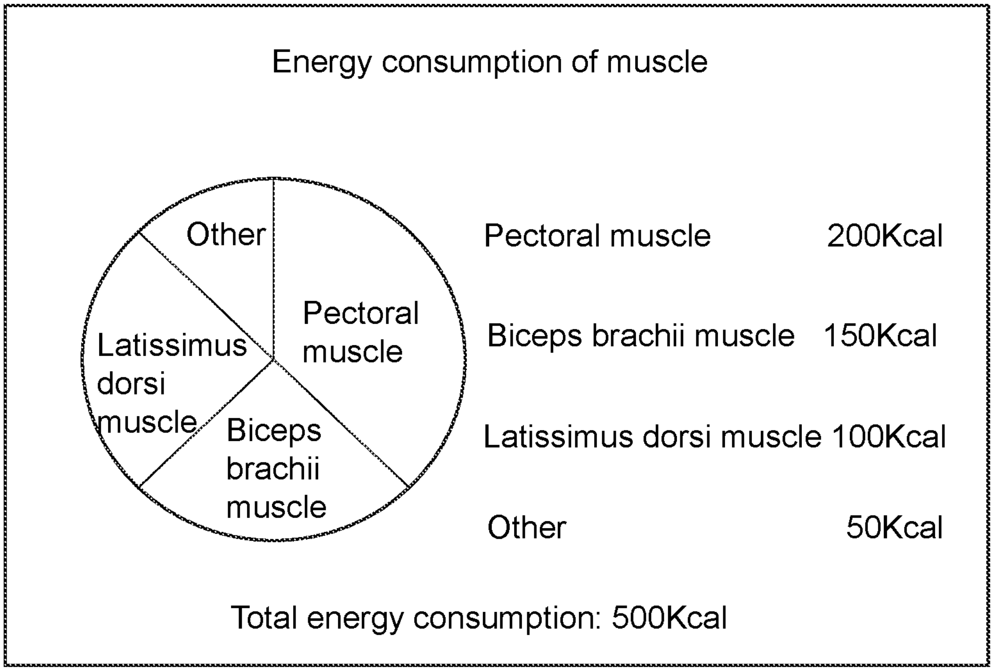
FIG. 26 is a schematic diagram of a motion monitoring interface according to some embodiments of the present disclosure.

FIG. 26 is a schematic diagram illustrating a motion monitoring interface according to some embodiments of the present disclosure. As shown in FIG. 26, an energy consumption of each muscle after a user completes a training is displayed in the form of a pie chart and a text in an interface 2600. It may be seen from FIG. 26 that, in the training, the energy consumption of each muscle of the user is arranged in descending order of a pectoral muscle, a biceps brachii muscle, a latissimus dorsi muscle and other muscles. The user may intuitively observe a proportion of energy consumption of each muscle through the pie chart.

Figure 27:
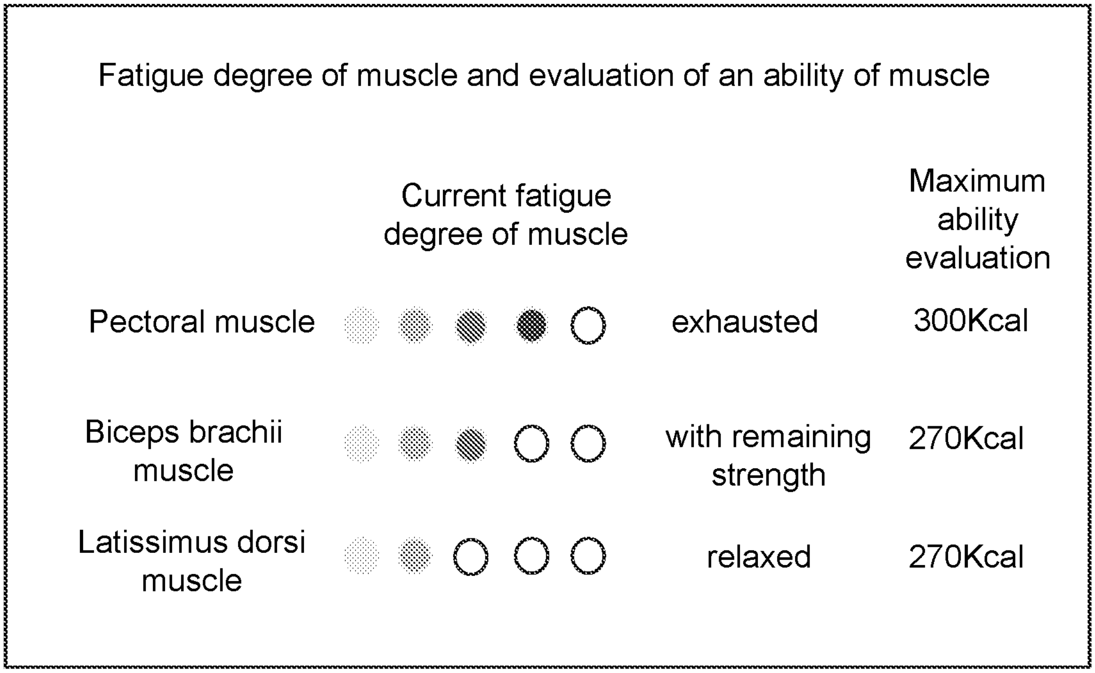
FIG. 27 is a schematic diagram of a motion monitoring interface according to some embodiments of the present disclosure.

FIG. 27 is a schematic diagram illustrating a motion monitoring interface according to some embodiments of the present disclosure. As shown in FIG. 27, a fatigue degree of muscle, an evaluation of the fatigue degree, and an evaluation of the maximum ability of muscle after a user completes a training is displayed in the form of a pattern and a text in an interface 2700. As shown in FIG. 27, different fatigue degrees of muscle may be represented by circular patterns of different colors, and the fatigue degree of each muscle may be evaluated according to the degree fatigue of muscle and the maximum ability of muscle (e.g., exhausted, with remaining strength, relaxed).

Figure 28:
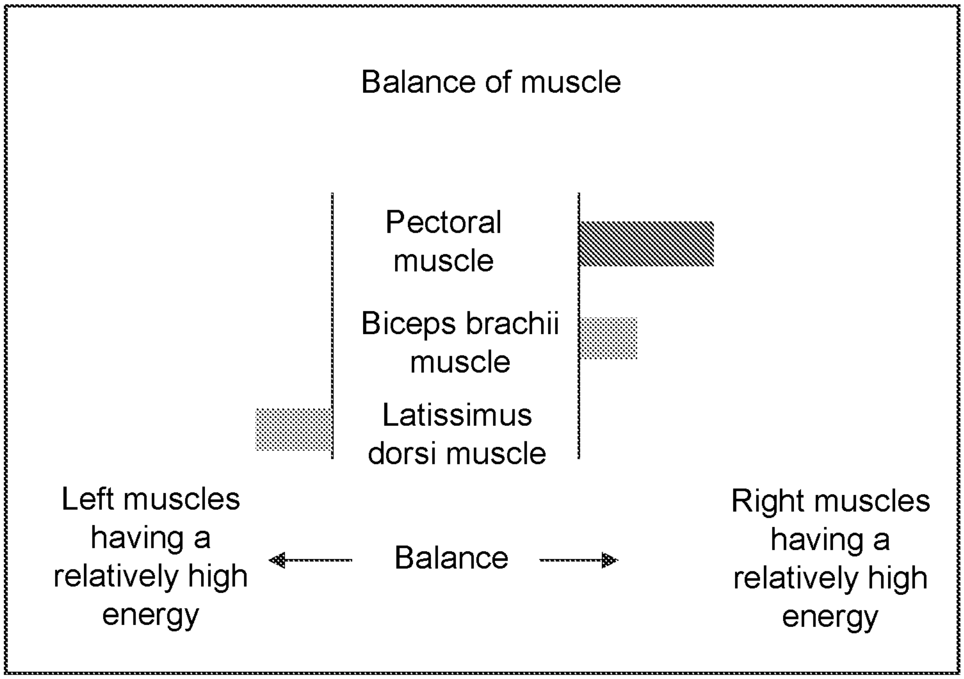
FIG. 28 is a schematic diagram of a motion monitoring interface according to some embodiments of the present disclosure.

FIG. 28 is a schematic diagram illustrating a motion monitoring interface according to some embodiments of the present disclosure. As shown in FIG. 28, a balance of left and right muscles of a body after a user completes a training is displayed in the form of a histogram in an interface 2800. Each kind of muscle may correspond to a columnar strip. A position, a length, and/or a color of the columnar strip may indicate the balance of the kind of muscle corresponding to the columnar strip. For example, the longer the length and/or the darker the color of the columnar strip corresponding to the muscle, the poorer the balance of the muscle. As shown in FIG. 28, the columnar strips corresponding to a pectoral muscle and a biceps brachii muscle are located on the right, which may indicate that the right pectoral muscle and the right biceps brachii muscle have a relatively high energy. The columnar strip corresponding a latissimus dorsi muscle is on the left, which may indicate that the left latissimus dorsi has a relatively high energy. In addition, a length of the columnar strip corresponding to the pectoral muscle is longer (or darker) than a length of the columnar strip corresponding to the biceps brachii muscle, which may indicate that the balance of the pectoral muscle is lower than the balance of the latissimus dorsi muscle.

Figure 29:
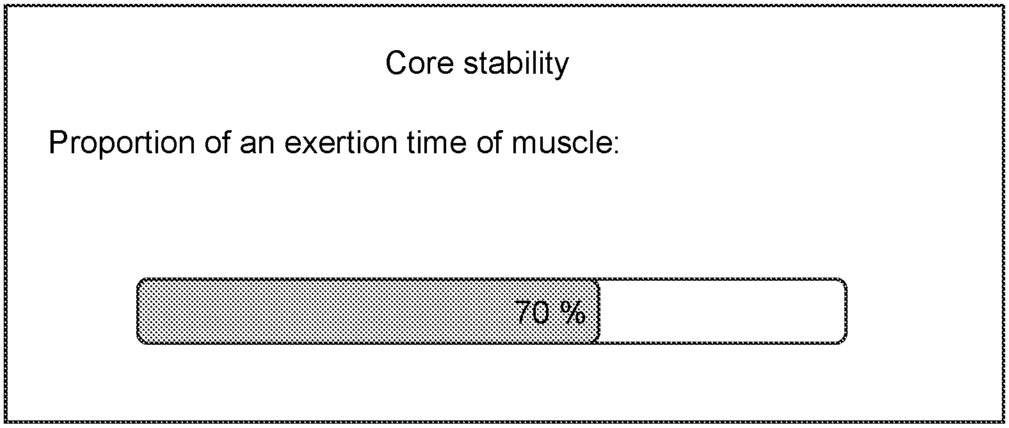
FIG. 29 is a schematic diagram of a motion monitoring interface according to some embodiments of the present disclosure.

FIG. 29 is a schematic diagram illustrating a motion monitoring interface according to some embodiments of the present disclosure. As shown in FIG. 29, a proportion of an exertion time of an abdominal muscle during a training process of a user is displayed in the form of a status bar in an interface 2900, which may reflect a core stability of the user. For example, it can be seen from FIG. 29 that the proportion of the exertion time of the abdominal muscle during the training process (e.g., sit-ups) of the user is 70%, which may reflect that the core stability of the user is good.

In some embodiments, the monitoring result may be displayed in a user model (e.g., the front muscle distribution map 2101 shown in FIG. 21B, the back muscle distribution model 2102, and the user movement model 010 shown in FIGS. 23A to 23C). For example, an energy consumption of at least one muscle, a fatigue degree of the at least one muscle, a training balance of at least two muscles, an ability of the at least one muscle of the user, or the like, or any combination thereof, may be displayed at least one specific location in the user model. The at least one specific location in the user model may correspond to a location of at least one muscle in the user. In some embodiments, energy consumptions of different muscles, fatigue degrees of different muscles, training balances of different muscles, and/or abilities of different muscles may correspond to different display colors, so that the user may feel the training result more intuitively. In some embodiments, the input/output module 260 may obtain a user input regarding a target muscle and display information of the target muscle in the display interface.

Figure 30:
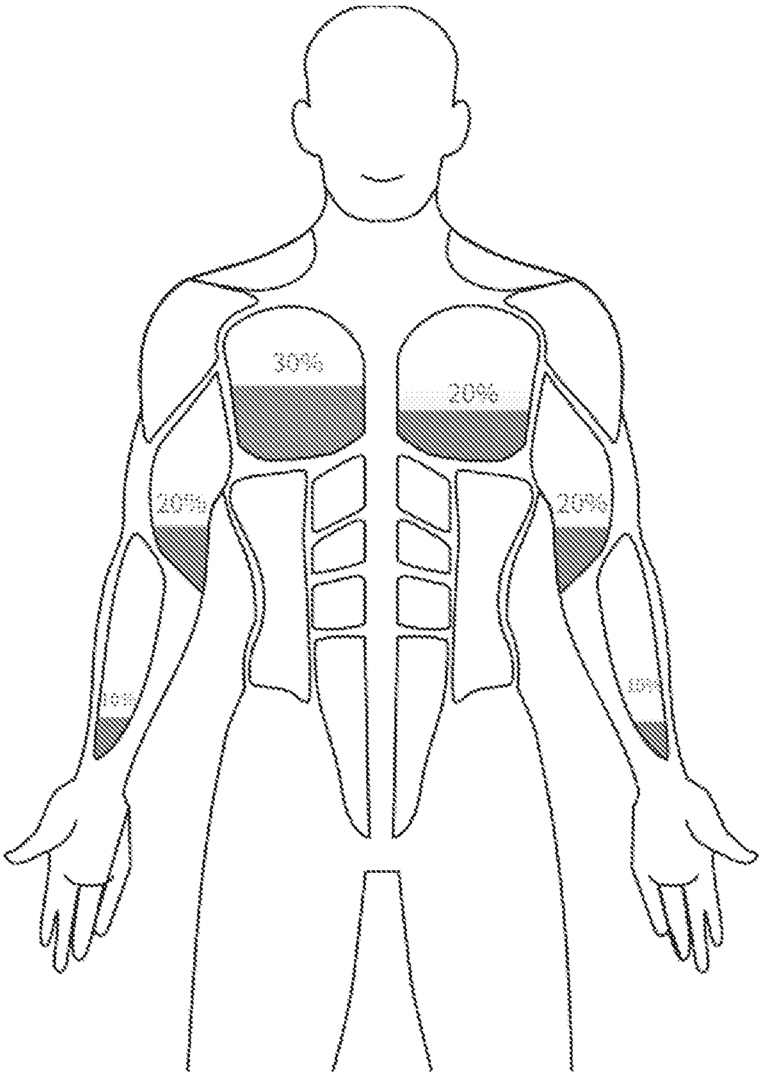
FIG. 30 is a schematic diagram of a motion monitoring interface according to some embodiments of the present disclosure.

FIG. 30 is a schematic diagram illustrating a motion monitoring interface according to some embodiments of the present disclosure. As shown in FIG. 30, contribution degrees of muscles (e.g., percentages of energy consumptions of muscles) during a training process of a user is displayed in the form of human muscle distribution map in an interface 3000. It can be seen from FIG. 30 that the contribution degree of a left pectoralis major muscle of the user is 20%, the contribution degree of a right pectoralis major muscle is 30%, and the contribution degrees of a left biceps brachii muscle and a right biceps muscle brachii muscle are both 20%. In some embodiments, the higher the contribution degree of the muscle, the darker the color of the muscle at a corresponding position in the muscle distribution map.

Figure 31:
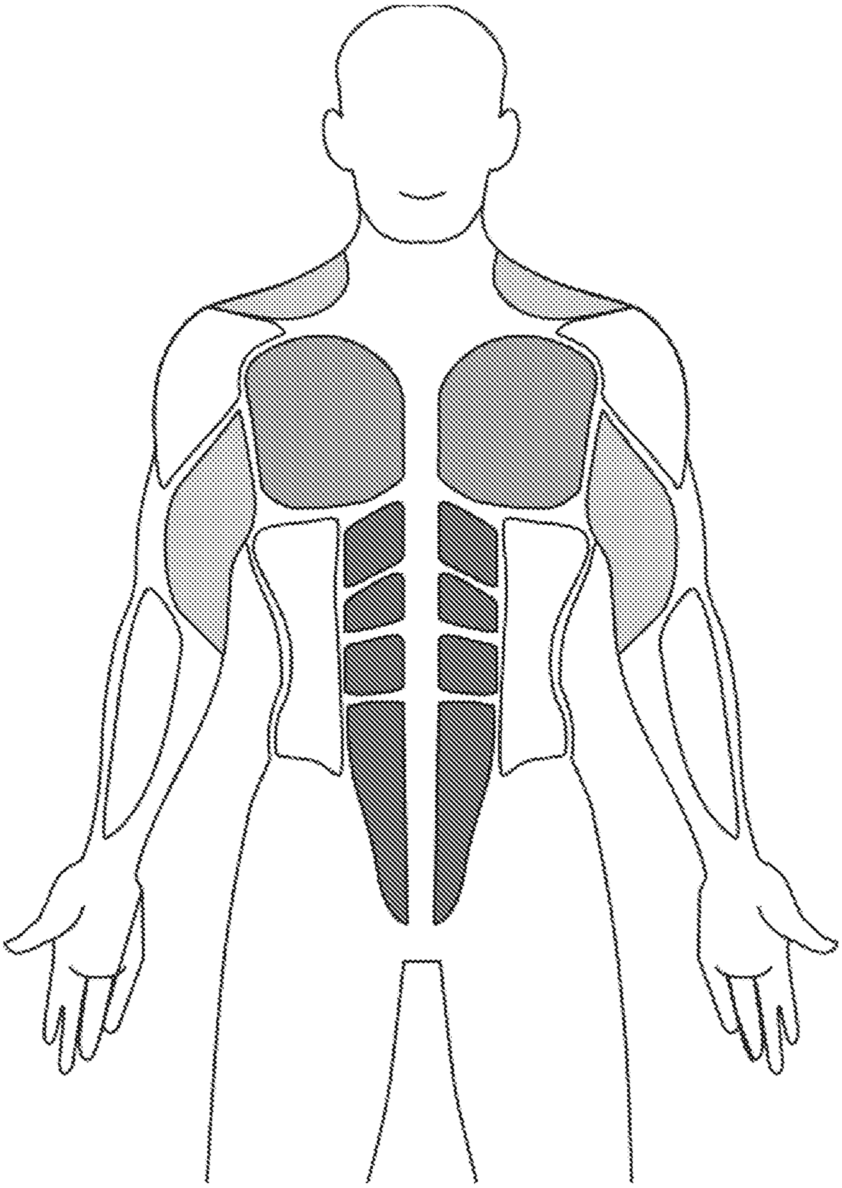
FIG. 31 is a schematic diagram of a motion monitoring interface according to some embodiments of the present disclosure.

FIG. 31 is a schematic diagram illustrating a motion monitoring interface according to some embodiments of the present disclosure. As shown in FIG. 31, a fatigue degree of muscle during a training process of the user is displayed in the form of human muscle distribution map in an interface 3100. For example, the higher the fatigue degree of the muscle, the darker the color of the muscle at a corresponding position in the muscle distribution map.

It should be noted that the interface display modes shown in FIGS. 25-31 are only examples. In some embodiments, the balance of at least two muscles and/or the ability of muscle may be displayed in the interface in the form of human muscle distribution map. In some embodiments, a plurality of monitoring results may be displayed in a plurality of ways in one interface. For example, the contribution degree of muscle and the fatigue degree of muscle of the user during a training process may be displayed simultaneously in the human muscle distribution map. As another example, the energy consumption of each muscle after the user completes the training may be displayed in the form of the pie chart in the interface, and the energy consumption of each muscle during the training process of the user may be displayed in the human muscle distribution map at the same time.

In some embodiments, the motion monitoring system 100 may count motion data during a plurality of training processes of the user and generate a motion record, thereby helping the user understand changes in physical performance and physical quality during long-term exercise and helping the user maintain good exercise habits.

Figure 32:
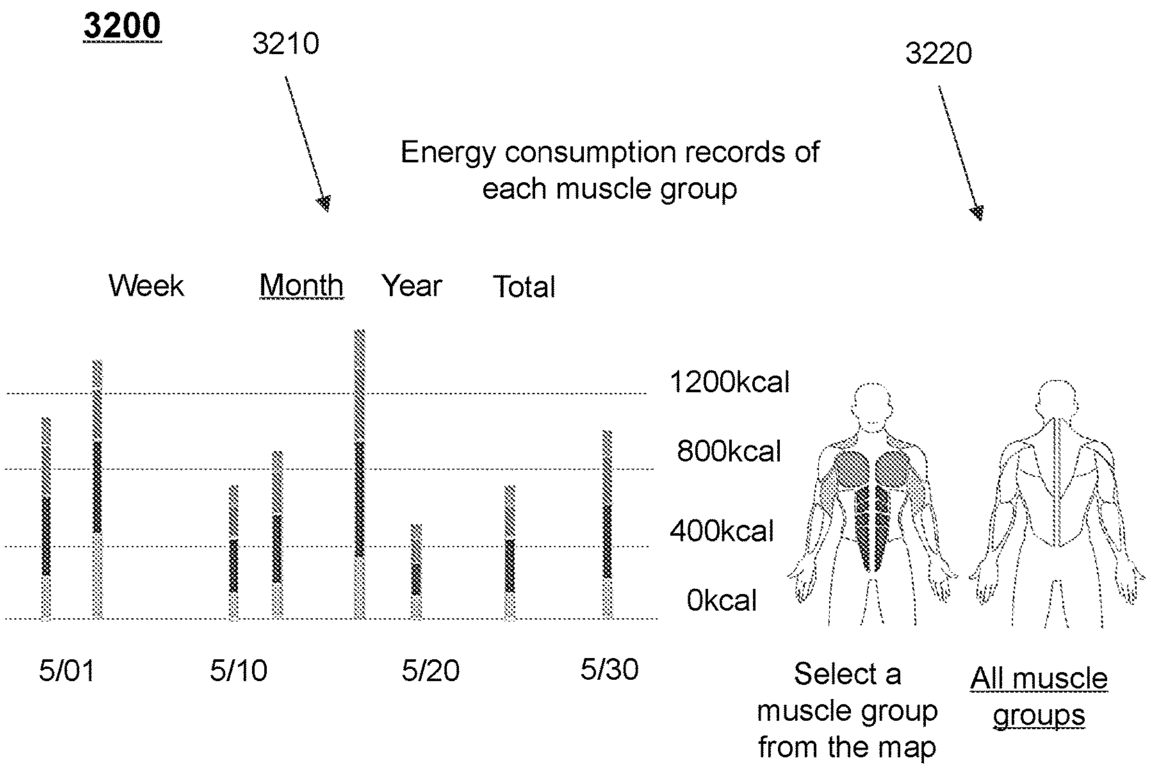
FIG. 32 is a schematic diagram of a motion monitoring interface according to some embodiments of the present disclosure.
Figure 33:
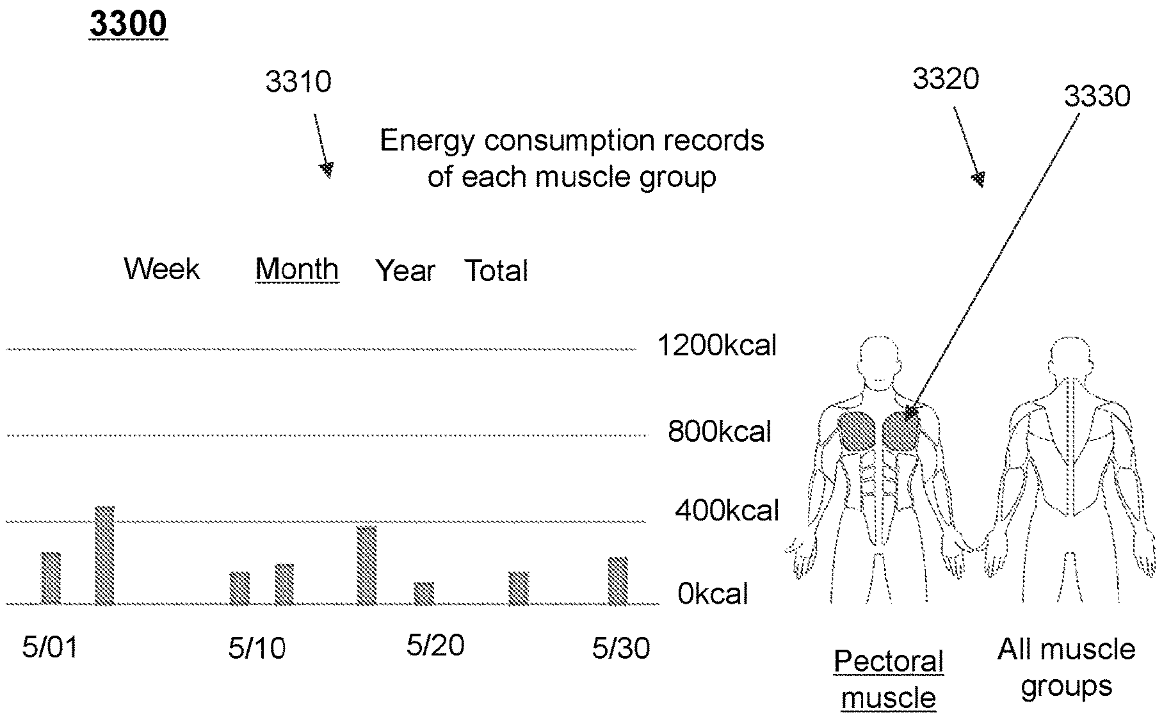
FIG. 33 is a schematic diagram of a motion monitoring interface according to some embodiments of the present disclosure.

FIG. 32 is a schematic diagram illustrating a motion monitoring interface according to some embodiments of the present disclosure. As shown in FIG. 32, a contribution degree (or an energy consumption) of each muscle of a user in different training cycles (e.g., training cycles in a unit of day, week, month, and year) is displayed through a histogram 3210 in an interface 3200. For example, contribution degrees of different muscles may be displayed in different colors in columnar bars. In some embodiments, the user may select a target muscle in a muscle distribution map 3220 in the interface 3200. For example, the user may click a muscle in the muscle distribution map 3220 as the target muscle. As shown in FIG. 33, when the user selects a pectoral muscle 3330 in a muscle distribution map 3320 as the target muscle, the contribution degree of the pectoral muscle in the different training cycles is displayed through a histogram 3310 in an interface 3300. Through long term statistics on the contribution degree of each muscle group, the user can understand his/her training preferences and training history, for example, which muscles are often exercised and which muscles have not been exercised for a long time, so as to help the user better develop a training plan.

Figure 34:
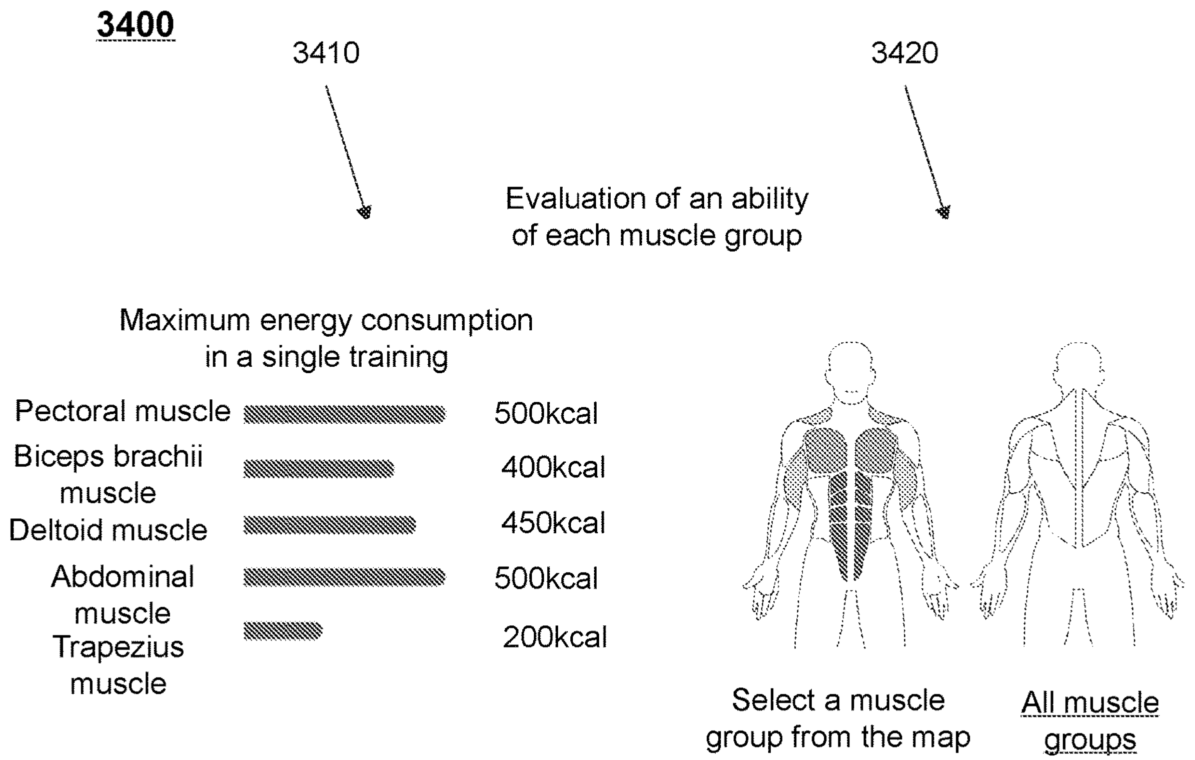
FIG. 34 is a schematic diagram of a motion monitoring interface according to some embodiments of the present disclosure.
Figure 35:
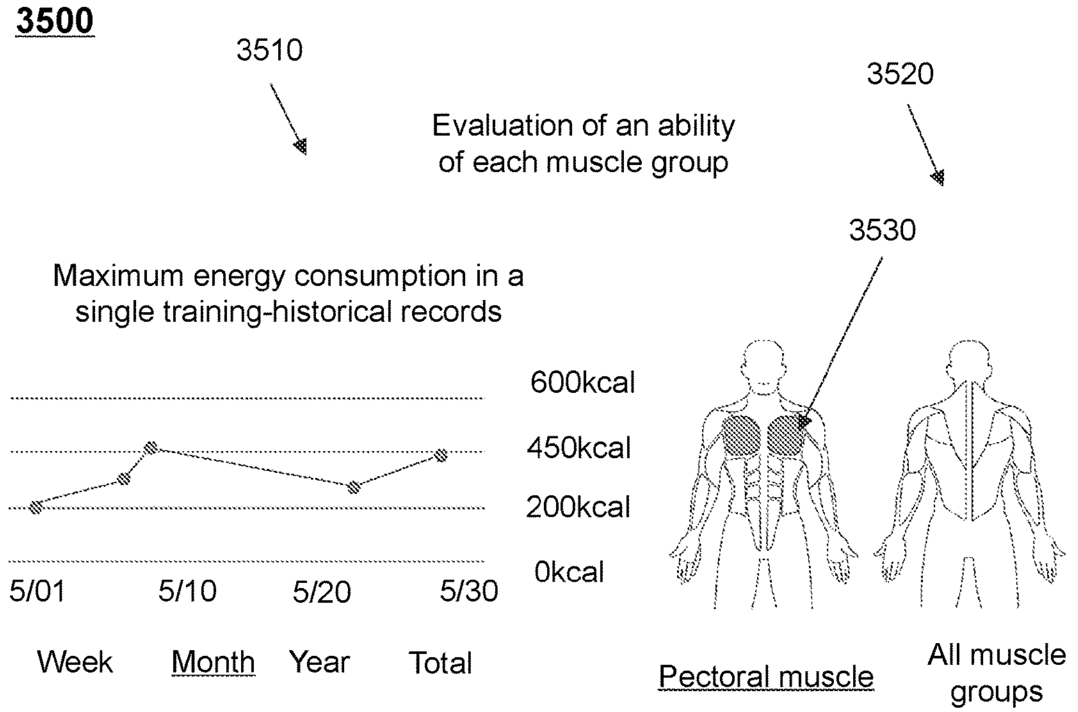
FIG. 35 is a schematic diagram of a motion monitoring interface according to some embodiments of the present disclosure.

FIG. 34 is a schematic diagram illustrating a motion monitoring interface according to some embodiments of the present disclosure. As shown in FIG. 34, the maximum energy consumption of each muscle during a training process of a user is displayed through a histogram 3410 in an interface 3400, thereby reflecting an ability of each muscle. In some embodiments, the user may select a target muscle in a muscle distribution map 3420 in the interface 3400. For example, the user may click a muscle in the muscle distribution map 3420 as the target muscle. As shown in FIG. 35, when the user selects a pectoral muscle 3530 in a muscle distribution map 3520 as the target muscle, the maximum energy consumption of the pectoral muscle in different training cycles is displayed through a line chart 3510 in an interface 3500. Through long-term statistics on the ability of each muscle group, the user can understand the growth of his/her ability, so as to help the user better develop a training plan.

Figure 36:
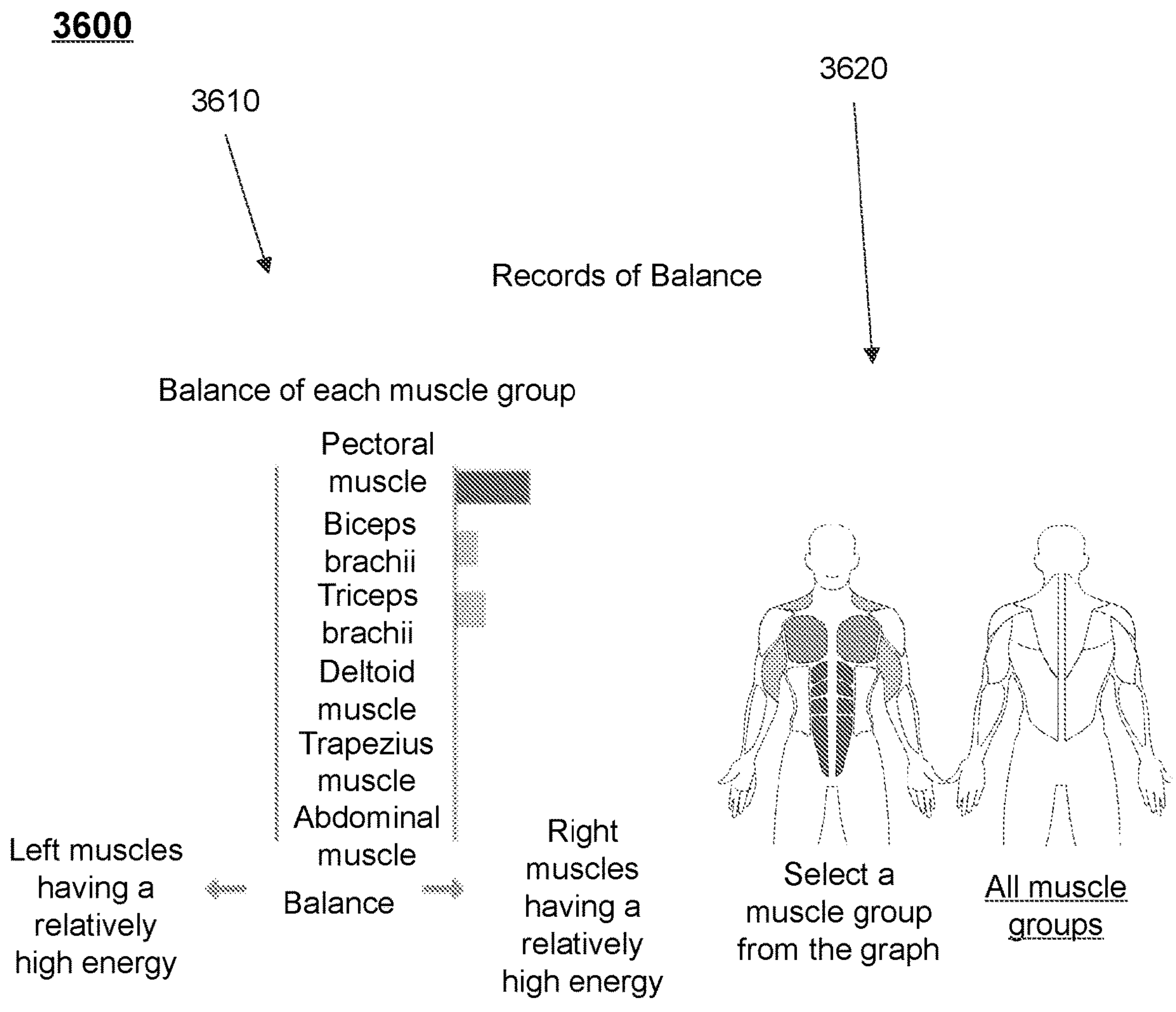
FIG. 36 is a schematic diagram of a motion monitoring interface according to some embodiments of the present disclosure.

FIG. 36 is a schematic diagram illustrating a motion monitoring interface according to some embodiments of the present disclosure. As shown in FIG. 36, a balance of muscle of the user is displayed through a histogram 3610 in an interface 3600. In some embodiments, the user may select a target muscle in a muscle distribution map 3620 in the interface 3600. For example, the user may click a muscle in the muscle distribution map 3620 as the target muscle. At this time, the interface may show the balance of the target muscle in different training cycles. By keeping a long-term record of the balance (or the core stability) of muscle, the user can understand his/her shortcomings and adjust the training plan in time.

It should be noted that the above description regarding the process 2400 is merely provided for the purpose of illustration, and not intended to limit the scope of the present disclosure. For those skilled in the art, various modifications and changes can be made to process 2400 under the guidance of the present disclosure. However, these amendments and changes are still within the scope of the present disclosure.

In some embodiments, the motion monitoring system 100 may calibrate the movement signal of the user obtained by the sensor. In some embodiments, the electromyographic signal collected by the electromyography sensor may be vulnerable to a plurality of factors (e.g., an individual user difference, a user skin status, an installation position of the electromyography sensor, an exertion strength of muscle, a fatigue degree of muscle). The factor such as the individual user difference, the user skin status, the installation position of the electromyography sensor, etc. may make it impossible to directly compare the obtained electromyographic signals for different users. Therefore, it is necessary to calibrate the electromyographic signal, so as to eliminate or weaken the influence of the factor such as the individual user difference, the user skin status, the installation position of the electromyography sensor, etc. on the electromyographic signal. In some embodiments, the motion monitoring system 100 may guide the user to perform a series of calibration movements (e.g., movements such as push-ups, etc. that can mobilize a large number of muscle groups to exert) to activate most of the muscle groups to be detected before the motion starts (e.g., a warm-up phase). For example, a display device (e. g., a screen) of the wearable device 130 or the mobile terminal device 140 may display the calibration movement, and the user may follow instructions to perform a corresponding calibration movement. The processing module 220 may determine an electromyographic signal collected by the electromyography sensor when the user performs the calibration movement as a reference value, and calibrate all the electromyographic signals collected by the user in the movement. For example, taking the push-up movement as the calibration movement as an example, before starting the motion, the motion monitoring system 100 may guide the user to perform a plurality of sets of push-ups (e.g., 3-5 push-ups), and collect electromyographic signals of activated muscles such as the pectoral muscle, the biceps brachii muscle, the triceps brachii muscle, the rectus abdominis muscle of the user, etc. through the electromyography sensor, and determine a specific multiple of the electromyography amplitude of the muscle activated by the push up movement as the reference value. In some embodiments, a range of the multiple may be between 1.2-5 times. For example, the multiple may be between 1.2-3 times. In some embodiments, each muscle may correspond to different multiples. The multiple may be a value preset by the user or the motion monitoring system 100, or a value determined by analyzing a feature of the electromyographic signal. In some embodiments, the reference value of the electromyographic signal of a target user in the motion may be determined based on a plurality of historical electromyographic signals collected when the target user performs a calibration movement during a plurality of historical motions. In some embodiments, the reference value of the electromyographic signal of the target user in the motion may be determined based on a plurality of electromyographic signals collected when a plurality of users perform a calibration movement. By using the plurality of historical electromyographic signals collected when the target user performs the calibration movement and/or the electromyographic signals collected when other users perform the calibration movement to adjust the electromyographic signals collected when the target user performs the current calibration movement, the accuracy and rationality of the reference value of the electromyographic signal in the movement may be improved.

In some embodiments, the motion monitoring system 100 may guide the user to warm up and display a warm-up result of the user. The warm-up exercise before the motion can improve the motion performance of the user, prevent the user from muscle twitching during the motion, and reduce the risk of injury. In some embodiments, the display device (e.g., the screen) of the wearable device 130 or the mobile terminal device 140 may display a series of warm-up movements to guide the user to warm up. In some embodiments, the processing module 220 may determine the warm-up result of the user based on physiological information of the user. For example, since the warm-up exercise will cause the heart rate of the user to increase, the body temperature of the user to rise, and a volume of perspiration of the user to increase, the sensor (e.g., an electrode) or other hardware devices disposed on the wearable device 130 may detect a contact impedance generated by the contact between the electrode and the human body, thus determining a sweating state of the human body, and determining whether the warm-up exercise of the user is sufficient according to the sweating state of the human body. As another example, a determination may be made as whether the warm-up exercise of the user is sufficient based on the fatigue degree of muscle of the user. As another example, a determination may be made as whether the warm-up exercise of the user is sufficient based on information such as an exercise volume, the heart rate, the body temperature, etc. of the user. In some embodiments, a warm-up suggestion may be provided to the user according to the warm-up result, for example, to prompt the user that the warm-up exercise is sufficient to start a formal exercise, or prompt the user to continue the warm-up exercise.

Figure 37:
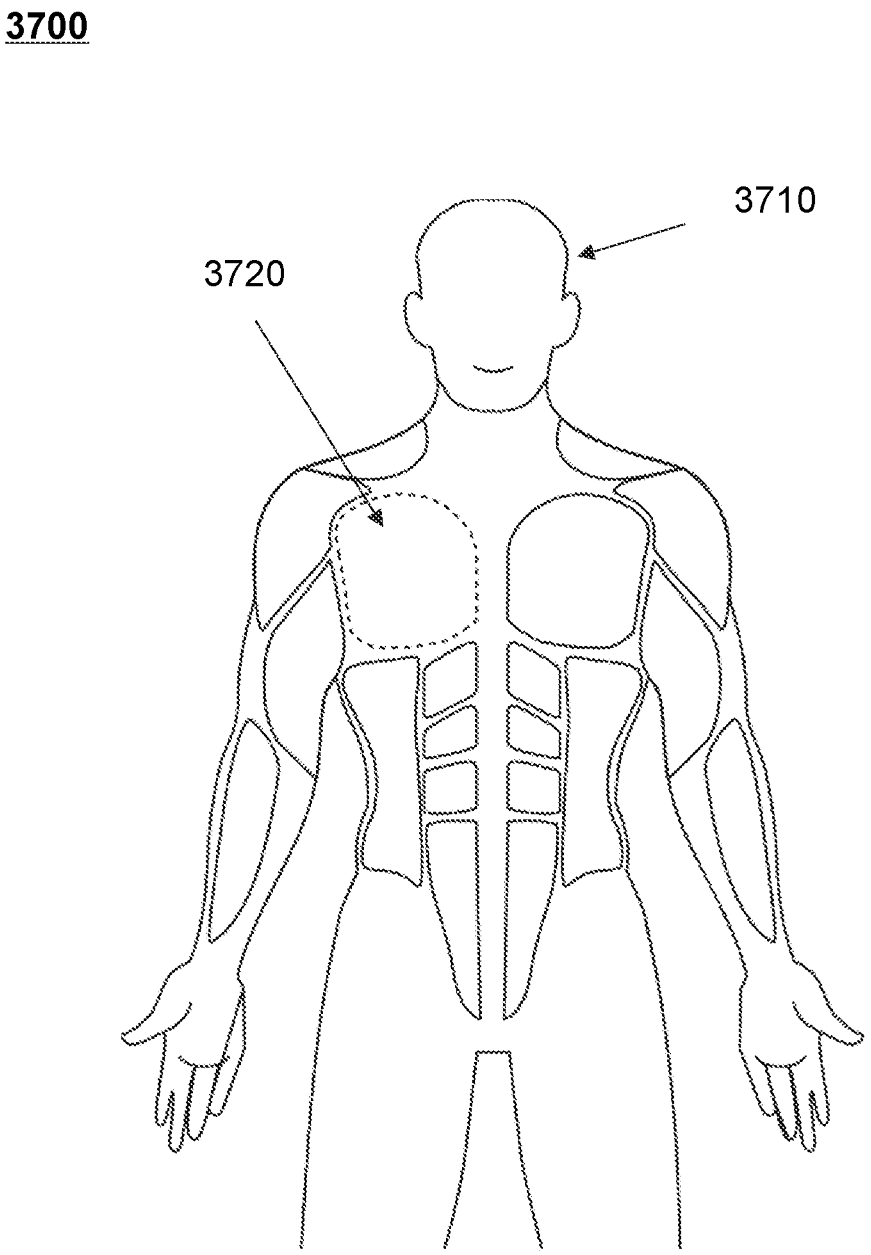
FIG. 37 is a schematic diagram of a motion monitoring interface according to some embodiments of the present disclosure.

In some embodiments, the processing module 220 may determine whether a working state of the sensor is normal based on the movement signal collected by the sensor. The working state of the sensor may include a contact state between the and the skin. The contact state between the sensor and the skin may include a degree of fit between the sensor and the skin, the contact impedance between the sensor and the skin, etc. The quality of the movement signal collected by the sensor set on the user's skin may be related to the contact state between the sensor and the skin. For example, when the degree of fit between the sensor and the skin is poor, there may be more noise in the movement signal collected by the sensor, resulting in that the movement signal cannot reflect a real motion state of the user. In some embodiments, the degree of fit between the sensor and the skin may be determined according to the quality of the movement signal (e.g., an amount of noise in the movement signal) and/or the contact impedance between the sensor and the skin. If the degree of fit between the sensor and the skin is lower than a certain threshold, it may be determined that the working state of the sensor is abnormal. At this time, prompt information may be sent to the user to remind the user to check the state of the sensor. FIG. 37 is a schematic diagram illustrating a motion monitoring interface according to some embodiments of the present disclosure. As shown in FIG. 37, an interface 3700 displays a human muscle distribution map 3710, and a dotted line 3720 indicates that the degree of fit between the sensor at a position of the right pectoral muscle and the user's skin is relatively low. In some embodiments, the position with low degree of fit between the sensor and the user's skin may be marked by other ways (e.g., mark using different colors).

In some embodiments, the movement signal of the user may include a signal related to a feature of the user. The processing module 220 may determine feature information of the user based on the signal related to the feature of the user. The feature information of the user may include body shape information, body composition information, etc. The body shape information may include a waist circumference, a chest circumference, a hip circumference, an arm length, a leg length, a shoulder width, etc. The body composition information may include a body weight, a body fat percentage, a fat distribution, a fat thickness, a muscle distribution, a bone density, etc. For example, a plurality of strain gauge sensors may be set at a plurality of parts of the user's body. By measuring a magnitude of a resistance of the strain gauge sensor that changes with a tensile length, the movement signals obtained may include displacement information, stress, etc. The movement signals may indicate the body shape information of the user. As another example, electrical signals may be applied to electrodes set at a plurality of parts of the user's body, and information of the conductivity characteristics inside the human body may be extracted by measuring a body surface potential, so as to perform a positioning measurement on the body composition of the user.

In some embodiments, the motion monitoring system 100 may monitor the feature information of the user for a long time, and display a statistical analysis result to the user to help the user better understand a physical condition and develop a more reasonable exercise plan. For example, the motion monitoring system 100 may recommend an appropriate exercise to the user, such as a muscle building exercise, a fat loss exercise, a stretching sport, etc., according to a change (e.g., a fat distribution of each part of the user, a muscle distribution of each part of the user) of the feature information of the user over a period of time.

In some embodiments, the wearable device of appropriate size may be recommended to the user according to the body shape information. For example, if the user becomes thinner after a long period of exercise, a prompt may be sent to the user to remind the user to replace with a new wearable device. As another example, when the user select other types of wearable devices, appropriate sizes may be recommended to the user according to the body shape information.

In some embodiments, when the user wears the wearable device 130 to exercise, the user may select a perceptual training mode. In the perceptual training mode, when the user's muscle (e.g., the target muscle) exerts, the display device (e.g., the screen) of the wearable device 130 or the mobile terminal device 140 may display the exertion strength of the muscle. For example, the exertion strength of the target muscle may be displayed through a status bar (e.g., the status bars 2103 and 2104 shown in FIG. 21B). As another example, the exertion strength of the target muscle may be displayed by the amount of the sound emitted by a sound output device (e.g., a speaker). As yet another example, a brightness and a color of a corresponding muscle position may be changed in a user model to show a change of the exertion strength of the target muscle. In some embodiments, if the exertion strength of the target muscle of the user is consistent with a standard exertion strength, the user may be prompted (e.g., by the voice prompt, the text prompt, etc.) to help the user strengthen the feeling of controlling muscles. Through the perceptual training mode, it can help the user learn to control limbs and muscles, increase an ability of the brain and the nervous system to control muscles, effectively improve a motion performance, improve a movement pattern, and even correct a posture.

Figure 38:
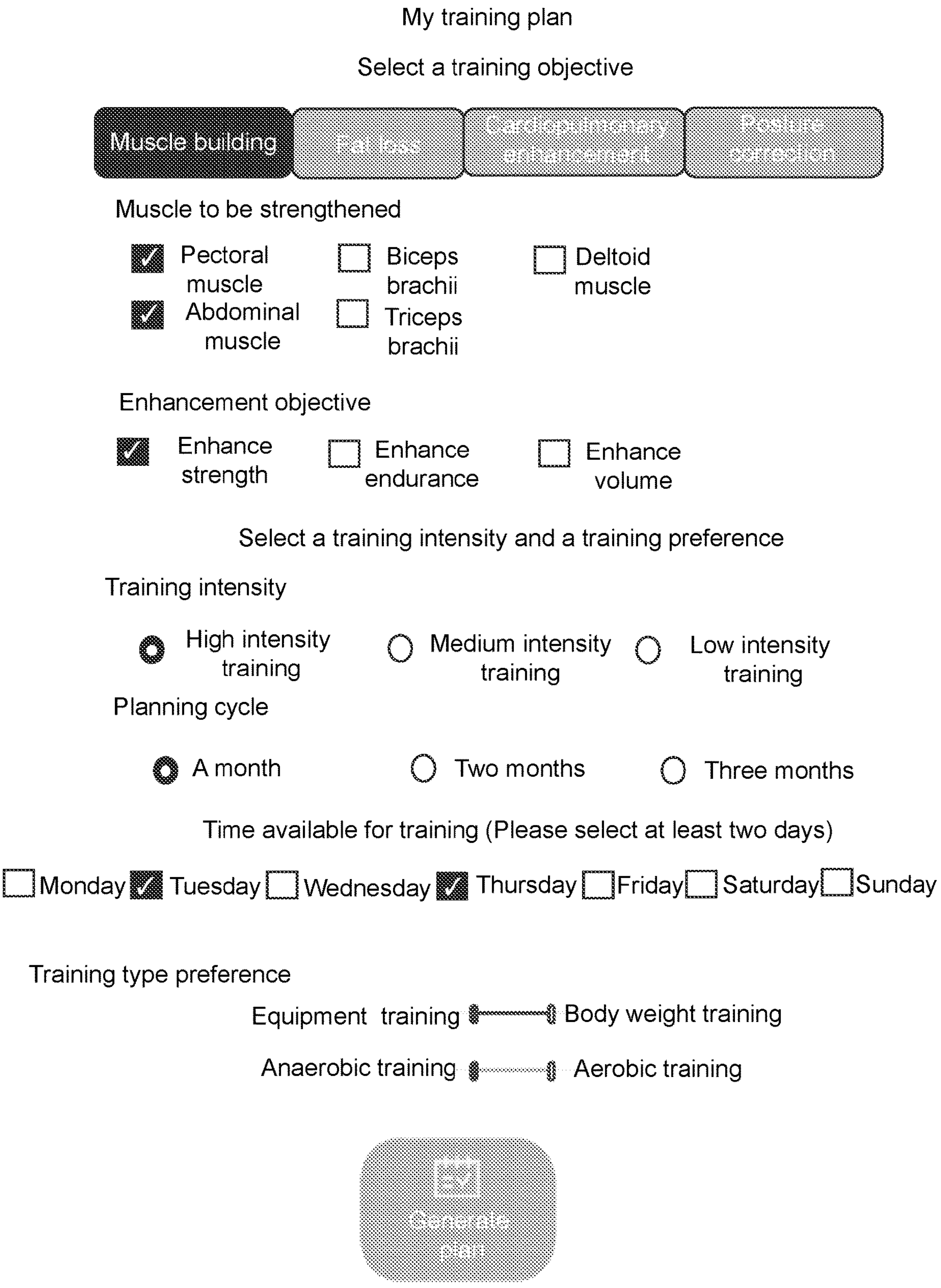
FIG. 38 is a schematic diagram of a motion monitoring interface according to some embodiments of the present disclosure.

In some embodiments, the motion monitoring system 100 may formulate a motion plan of the user based on information related to the user. The information related to the user may include feature information (e.g., the gender, the body shape information, the body composition information), an exercise history, an injury history, a health status, an expected training objective (e.g., a muscle building training, a fat loss training, a cardio pulmonary enhancement training, a posture correction training), an expected training intensity (e.g., a high-intensity training, a medium intensity training, a low-intensity training), a training type preference (e.g., an equipment training, a body weight training, an anaerobic training, an aerobic training), etc. of the user. In some embodiments, a professional (e.g., a fitness instructor) may formulate a motion plan according to the information related to the user, and upload the motion plan to the motion monitoring system 100. The user may modify and adjust the motion plan according to an actual situation. FIG. 38 is a schematic diagram illustrating a motion monitoring interface according to some embodiments of the present disclosure. As shown in FIG. 38, a user may enter or select a training objective (e.g., a muscle to be strengthened, an enhancement objective), a training intensity (e.g., the high-intensity training, the medium intensity training, the low-intensity training), a training type preference (e.g., the equipment training, the body weight training, the anaerobic training, the aerobic training), a training time, a planning cycle, etc. in an interface 3800. The motion monitoring system 100 may specify an appropriate motion plan for the user according to the input and the selection of the user.

In some embodiments, the motion monitoring system 100 may estimate a service life of the wearable device (e.g., a remaining usable time, a remaining count of cleanable times, a remaining count of usable times). For example, the wearable device may include a clothing life analysis module. The clothing life analysis module may determine a wear degree of the wearable device according to the contact impedance between the and the user, the quality of the movement signal (e.g., an electromyography sensor signal, an inertial sensor signal, a stress sensor signal) collected by the sensor, and the status of the wearable device (e.g., a count of times cleaned, a used time, a count of times used), and estimate the service life according to the wear degree of the wearable device. In some embodiments, when the service life of the wearable device is less than a certain usable time (e.g., one week) or less than a certain count of usable times (e.g., five times), a prompt may be sent to the user to remind the user to replace with a new wearable device in time.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "data block," "module," "engine," "unit," "component," or "system." Furthermore, aspects of the present disclosure may take the form of a computer program product embodied in one or more computer-readable media having computer-readable program code embodied thereon.

A computer storage medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer storage medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for displaying a motion monitoring interface, comprising:

- obtaining a movement signal during a motion of a user from at least one sensor, wherein the movement signal at least includes an electromyographic signal or an attitude signal;
- determining, by a processor, information related to the motion of the user by processing the movement signal, comprising:
  - segmenting, by the processor, the movement signal based on the electromyographic signal or the attitude signal; and
  - determining, by the processor, a monitoring result by monitoring the motion of the user based on at least one segment of the movement signal;
- displaying, by a display device, the information related to the motion of the user;
- determining, by the processor, a movement feedback mode based on the monitoring result, including:
  - determining whether an error occurs during the motion of the user based on the monitoring result; and
  - determining a feedback priority of the motion according to a type of error, wherein
    - the type of the error reflects a degree of damage to a user's body when the error occurs; and
    - the type of the error includes a type of primary movement error, a type of secondary movement error, and a type of tertiary movement error; and
- performing, by an input/output module, a movement feedback to the user according to the movement feedback mode, wherein
  - the movement feedback mode includes the feedback priority, the feedback priority includes immediate feedback, feedback after a movement is completed, or feedback after a training is completed;
  - when the type of the error is the type of primary movement error, the feedback priority is the immediate feedback;

when the type of the error is the type of secondary movement error, the feedback priority is the feedback after a movement is completed;

when the type of the error is the tertiary movement error, the feedback priority is the feedback after a training is completed; and the performing the movement feedback to the user comprises:

in response to determining that the motion of the user is an incorrect movement, controlling, by the processor, a component of a wearable device to stimulate a corresponding part of the motion of the user through a vibration feedback, an electrical stimulation feedback, or a pressure feedback.

2. The method of claim 1, wherein the determining information related to the motion of the user by processing the movement signal comprises:

determining an exertion strength of at least one muscle of the user based on the electromyographic signal.

3. The method of claim 2, wherein the displaying the information related to the motion of the user comprises:

obtaining a user input regarding a target muscle; and displaying a status bar, wherein a color of the status bar is related to an exertion strength of the target muscle, or making a sound, wherein a volume of the sound is related to the exertion strength of the target muscle.

4. The method of claim 1, wherein the determining information related to the motion of the user by processing the movement signal comprises:

generating a user movement model representing the motion of the user based on the attitude signal;

the displaying the information related to the motion of the user comprises:

obtaining a standard movement model; and displaying the user movement model and the standard movement model, wherein the user movement model includes a virtual character that displays a posture of the motion of the user.

5. The method of claim 4, wherein the displaying the information related to the motion of the user comprises:

determining an exertion strength of at least one muscle of the user based on the electromyographic signal; and displaying the exertion strength of the at least one muscle on the user movement model.

6. The method of claim 1, wherein the at least one segment of the movement signal is a movement signal of the user in at least one training process, and the monitoring result includes at least one of a movement type, a movement quantity, a movement quality, a movement time, physiological parameter information of the user, or a core stability of the user during the at least one training process.

7. The method of claim 1, wherein the monitoring result includes muscle information of the user corresponding to at least one time point, the muscle information of the user includes at least one of an energy consumption of at least one muscle, a fatigue degree of the at least one muscle, a balance of at least two muscles, or an ability of the at least one muscle, and the displaying the information related to the motion of the user comprises:

displaying at least one of the energy consumption of the at least one muscle, the fatigue degree of the at least one muscle, the balance of the at least two muscles, or the ability of the at least one muscle on at least one location in a user model, wherein the at least one location in the user model corresponds to a location of the at least one muscle in the user.

8. The method of claim 7, wherein energy consumptions of different muscles, fatigue degrees of different muscles, training balances of different muscles, and/or abilities of different muscles correspond to different display colors.

9. The method of claim 7, wherein the displaying the information related to the motion of the user comprises:

obtaining a user input regarding a target muscle; and displaying information of the target muscle.

10. The method of claim 1, wherein the displaying the information related to the motion of the user comprises:

displaying the monitoring result in at least one form of a text, a chart, a sound, an image, or a video.

11. The method of claim 1, further comprising:

calibrating the movement signal.

12. The method of claim 11, wherein the calibrating the movement signal includes:

before the motion starts, displaying a calibration movement by the display device of the wearable device to make the user follow an instruction to perform the calibration movement; and determining an electromyographic signal collected by an electromyography sensor when the user performs the calibration movement; and determining a specific multiple of an electromyography amplitude of the electromyographic signal collected by the electromyography sensor as a reference value, and calibrating the electromyographic signal collected by the user in the movement based on the reference value, wherein different muscles correspond to different multiples.

13. The method of claim 1, further comprising:

determining whether a working state of the at least one sensor is normal based on the movement signal; and in response to determining that the working state of the at least one sensor is abnormal, displaying prompt information.

14. The method of claim 1, wherein the movement signal includes a signal related to a feature of the user, and the method further comprises:

determining body shape information and/or body composition information of the user based on the signal related to the feature of the user; and displaying the body shape information and/or the body composition information of the user.

15. The method of claim 1, wherein the monitoring result includes a movement type; and the determining the movement feedback mode based on the monitoring result comprises:

determining the feedback priority based on the movement type.

16. The method of claim 1, wherein the movement feedback mode includes a feedback content; and the determining the movement feedback mode based on the monitoring result comprises:

determining the feedback content at least based on the type of the movement error.

17. An electronic device, wherein the electronic device comprises:

a display device, configured to display content;

an input device, configured to receive a user input;

at least one sensor, configured to detect a movement signal during a motion of a user, wherein the movement signal at least includes an electromyographic signal or an attitude signal; and a processor, connected to the display device, the input device, and the at least one sensor, wherein the processor is configured to:

obtain the movement signal during the motion of the user from the at least one sensor;

determine information related to the motion of the user by processing the movement signal, wherein to determine information related to the motion of the user by processing the movement signal, the processor is further configured to:

segment the movement signal based on the electromyographic signal or the attitude signal; and determine a monitoring result by monitoring a the motion of the user based on at least one segment of the movement signal;

control the display device to display the information related to the motion of the user;

determine a movement feedback mode based on the monitoring result, to perform the movement feedback to the user, the processor is further configured to:

determine whether an error occurs during the motion of the user based on the monitoring result; and determine a feedback priority of the motion according to a type of error, wherein the type of the error reflects a degree of damage to a user's body when the error occurs; and the type of the error includes a type of primary movement error, a type of secondary movement error, and a type of tertiary movement error; and perform, by an input/output module, a movement feedback to the user according to the movement feedback mode, wherein the movement feedback mode includes a feedback priority, the feedback priority includes immediate feedback, feedback after a movement is completed, or feedback after a training is completed;

when the type of the error is the type of primary movement error, the feedback priority is the immediate feedback;

when the type of the error is the type of secondary movement error, the feedback priority is the feedback after a movement is completed;

when the type of the error is the tertiary movement error, the feedback priority is the feedback after a training is completed; and to perform the movement feedback to the user, the processor is further configured to:

in response to determining that the motion of the user is an incorrect movement, control a component of a wearable device to stimulate a corresponding part of the motion of the user through a vibration feedback, an electrical stimulation feedback, or a pressure feedback.

18. The electronic device of claim 17, wherein the processor is configured to:

determine whether a working state of the at least one sensor is normal based on the movement signal; and in response to determining that the working state of the at least one sensor is abnormal, display prompt information.

19. The electronic device of claim 17, wherein the movement signal includes a signal related to a feature of the user, and the processor is configured to:

determine body shape information and/or body composition information of the user based on the signal related to the feature of the user; and display the body shape information and/or the body composition information of the user.

20. The electronic device of claim 17, wherein to control the display device to display the information related to the motion of the user, the processor is configured to:

obtain, form the input device, a user input regarding a target muscle; and control the display device to display the information related to information of the target muscle.

* * * * *